United States Patent
Anderson et al.

(10) Patent No.: US 11,198,887 B2
(45) Date of Patent: Dec. 14, 2021

(54) CORN TRANSGENIC EVENT MON 95379 AND METHODS FOR DETECTION AND USES THEREOF

(71) Applicant: Monsanto Technology LLC, St. Louis, MO (US)

(72) Inventors: Heather M. Anderson, Wildwood, MO (US); Sarah L. Brown, St. Louis, MO (US); Renato A. Carvalho, St. Louis, MO (US); Ancideriton A. Castro, St. Louis, MO (US); Katherine M. Dunkmann, St. Louis, MO (US); Adam J. Evans, St. Louis, MO (US); Stanislaw Flasinski, Ballwin, MO (US); Cara L. Griffith, Catawissa, MO (US); Tianxiang Shen, St. Louis, MO (US); Todd R. Smith, St. Louis, MO (US); Heidi M. Windler, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 16/525,278

(22) Filed: Jul. 29, 2019

(65) Prior Publication Data
US 2020/0032289 A1 Jan. 30, 2020

Related U.S. Application Data

(60) Provisional application No. 62/711,810, filed on Jul. 30, 2018.

(51) Int. Cl.
*C12N 15/82* (2006.01)
*C07K 14/325* (2006.01)
*C12N 15/10* (2006.01)

(52) U.S. Cl.
CPC ........ *C12N 15/8286* (2013.01); *C07K 14/325* (2013.01); *C12N 15/102* (2013.01); *C12N 15/8274* (2013.01); *Y02A 40/146* (2018.01)

(58) Field of Classification Search
None
See application file for complete search history.

(56) References Cited

U.S. PATENT DOCUMENTS

| 6,593,273 | B2 | 7/2003 | Asrar et al. |
| 9,469,880 | B2 | 10/2016 | Adams et al. |
| 2016/0108426 | A1* | 4/2016 | Baum .................... A01N 63/10 800/279 |
| 2016/0108428 | A1* | 4/2016 | Baum .................... A01N 63/10 800/302 |

OTHER PUBLICATIONS

Invitation to Pay Additional Fees regarding PCT Application No. PCT/US2019/043666, dated Oct. 11, 2019, 3 pages.
Genbank submission KG815221 [database online], Dec. 23, 2014, [retrieved on Nov. 12, 2019]. Retrieved from: <https://www.ncbi.nlm.nih.gov/nuccore/KG815221> full document.
Genbank submission CP015659 [database online], May 23, 2016, [retrieved on Nov. 5, 2019]. Retrieved from: <https://www.ncbi.nlm.nih.gov/nuccore/LR584442> full document.
Genbank submission F1982754 [database online], May 22, 2010, [retrieved on Nov. 12, 2019], Retrieved from: <https://www.ncbi.nlm.nih.gov/nuccore/F1982754> full document.
Genbank submission BZ318215 [database online], Nov. 6, 2002, [retrieved on Nov. 12, 2019]. Retrieved from: <https://www.ncbi.nlm.nih.gov/nuccore/BZ318215> full document.
Genbank submission LN503569 [database online], Sep. 15, 2014, [retrieved on Nov. 12, 2019]. Retrieved from: <https://www.ncbi.nlm.nih.gov/nuccore/LN503569> full document.
Genbank submission AC230033 [database online], Sep. 21, 2013, [retrieved on Nov. 12, 2019]. Retrieved from: <https://www.ncbi.nlm.nih.gov/nuccore/AC230033> full document.
International Search Report and Written Opinion regarding PCT Application No. PCT/US2019/043666, dated Jan. 7, 2020, 12 pages.

* cited by examiner

*Primary Examiner* — Anne Kubelik
(74) *Attorney, Agent, or Firm* — Dentons US LLP; Timothy K. Ball, Esq.

(57) ABSTRACT

The invention provides a transgenic corn event MON 95379, plants, plant cells, seeds, plant parts, progeny plants, and commodity products comprising event MON 95379. The invention also provides polynucleotides specific for event MON 95379 and methods for using and detecting event MON 95379 as well as plants, plant cells, seeds, plant parts, progeny plants, and commodity products comprising event MON 95379.

17 Claims, 3 Drawing Sheets

Specification includes a Sequence Listing.

US 11,198,887 B2

CORN TRANSGENIC EVENT MON 95379 AND METHODS FOR DETECTION AND USES THEREOF

REFERENCE TO RELATED APPLICATION

This application claims the benefit of U.S. provisional application No. 62/711,810, filed Jul. 30, 2018, which is herein incorporated by reference in its entirety.

INCORPORATION OF SEQUENCE LISTING

The sequence listing contained in the file named MONS463US_ST25 is 74.7 kilobytes (measured in Microsoft Windows®), was created on Jul. 25, 2019, is filed herewith by electronic submission, and is incorporated by reference.

FIELD OF THE INVENTION

The invention relates to recombinant DNA molecules present in and/or isolated from corn event MON 95379. The invention also relates to transgenic corn plants, plant parts, and seeds, cells, and agricultural products containing corn event MON 95379, as well as methods of using the same and detecting the presence of corn event MON 95379. Transgenic corn plants, parts, seeds and cells containing corn event MON 95379 DNA exhibit resistance to insect infestations in the family Lepidoptera.

BACKGROUND OF THE INVENTION

Corn (*Zea mays*) is an important crop and is a primary food source in many areas of the world. The methods of biotechnology have been applied to corn for improvement of the agronomic traits and quality of the product. One such agronomic trait is insect resistance, which is accomplished through the expression of heterologous insect toxins, also known as transgenes, inserted into the genome of the corn plant.

The expression of such transgenes in a transgenic plant, plant part, seed or cell may be influenced by many different factors, including the elements used in the cassettes driving transgene expression and the interaction of those elements within a cassette. This is complicated further for a transgenic insertion containing two or more expression cassettes, with each expression cassette having a transgene conferring a separate trait, also known as a multi-gene transgenic event. A commercially useful multi-gene transgenic event requires that each of the transgenes in the transgenic insertion express in the manner necessary for each trait. To achieve this, individual expression cassettes first are designed and tested in plants, and the expression cassettes that show the best insect activity, while not resulting in negative phenotypes due to expression, are selected for each trait. Next, the selected expression cassettes for one trait are combined with the selected expression cassettes for the other trait into a single construct. Multiple constructs are designed using different orientations to provide the best resistance and prevent the occurrence of negative phenotypes or negative agronomics, such as lower yield. The constructs are tested to ensure all the expression cassettes function well together and each transgene is properly expressed. Then, the selected combination and orientation of expression cassettes is used as a single transgenic insert to produce hundreds transgenic events, each event being the result of the random insertion of the construct in a different genomic location.

Each transgenic event is unique in its molecular profile and chromosomal insertion point. Because of the variability involved in event creation, each unique event must be analyzed through multiple generations of plants—in each step assessing the molecular characterization, protein expression efficacy, and agronomics—to select a superior event for commercial use. The performance of an event in a transgenic plant, plant part, seed or cell, and therefore its effectiveness, may be influenced by the genomic location of the transgene insertion. Specifically, the effectiveness of the event can be impacted by cis and/or trans factors relative to the integration site or chromatin structure. Events can have the same transgenic insertion and nonetheless have different transgene expression levels and performance across tissues and developmental stages, in various germplasm, or under specific growth conditions. There may also be undesirable phenotypic or agronomic differences between some events. Therefore, it is necessary to produce and analyze a large number of individual plant transformation events in order to select an event having superior properties relative to the desirable trait, and the optimal phenotypic and agricultural characteristics necessary to make it suitable for commercial purposes. Further, the creation of a multi-gene event for commercial use requires rigorous molecular characterization, greenhouse testing, and field trials over multiple years, in multiple locations, and under a variety of conditions so extensive agronomic, phenotypic, and molecular data may be collected. The resulting data must then be analyzed by scientists and agronomists to select an event that is useful for commercial purposes. Once selected, such an event may then be introgressed using plant breeding methods as a single locus having multiple insect resistance traits into new germplasm suitably adapted to specific local growing conditions, and stacked/combined by breeding with other different events conferring traits different from the traits conferred by the event of the present invention.

SUMMARY OF THE INVENTION

The invention provides a novel transgenic corn event—MON 95379—that provides insecticidal control over Lepidopteran pests of corn. The invention also provides transgenic plants, plant cells, seeds, plant parts, and commodity products comprising event MON 95379. In another embodiment, the invention provides polynucleotides specific for event MON 95379 and plants, plant cells, seeds, plant parts, progeny plants, and commodity products comprising event MON 95379. In yet another embodiment, methods related to event MON 95379 are provided.

Thus, in one aspect the invention provides a recombinant DNA molecule comprising a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, and a complete complement thereof.

In one embodiment, the recombinant DNA molecule is derived from corn event MON 95379 in a sample of seed containing said event having been deposited as ATCC Accession No. PTA-125027.

Another aspect of the invention provides a DNA molecule comprising a polynucleotide segment of sufficient length to function as a DNA probe that hybridizes specifically under stringent hybridization conditions with corn event MON 95379 DNA in a sample, wherein detecting hybridization of said DNA molecule under said stringent hybridization conditions is diagnostic for the presence of corn event MON 95379 DNA in said sample. In certain embodiments, the sample comprises a corn plant, corn plant cell, corn seed, corn plant part, corn progeny plant, processed corn seed, animal feed comprising corn, corn oil, corn meal, corn flour, corn flakes, corn bran, pasta made with corn, corn biomass, and fuel products produced using corn and corn parts.

Yet another aspect of the invention provides a pair of DNA molecules, comprising a first DNA molecule and a second DNA molecule different from the first DNA molecule, that function as DNA primers when used together in an amplification reaction with a sample containing corn event MON 95379 template DNA to produce an amplicon diagnostic for the presence of said corn event MON 95379 DNA in said sample, wherein said amplicon comprises the nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

Another embodiment of the invention is a method of detecting the presence of a DNA segment diagnostic for corn event MON 95379 DNA in a sample, said method comprising: a) contacting the sample with a DNA molecule that functions as a probe and hybridizes specifically under stringent conditions with corn event MON 95379; b) subjecting said sample and said DNA molecule to stringent hybridization conditions; and c) detecting hybridization of said DNA molecule to said DNA in said sample, wherein said detection is diagnostic for the presence of said corn event MON 95379 DNA in said sample.

Yet another embodiment of the invention is a method of detecting the presence of a DNA segment diagnostic for corn event MON 95379 DNA in a sample, the method comprising: a) contacting said sample with the pair of DNA molecules of the invention; b) performing an amplification reaction sufficient to produce a DNA amplicon; and c) detecting the presence of said DNA amplicon in said reaction, wherein said DNA amplicon comprises the nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10.

Another embodiment of the invention is a corn plant, corn plant part, corn cell, or part thereof comprising a recombinant polynucleotide molecule comprising the nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. This corn plant, corn plant part, corn cell, or part thereof is insecticidal when provided in the diet of a Lepidopteran insect pest. Lepidopteran pests can include Fall Armyworm (*Spodoptera frugiperda*), Corn Earworm (*Helicoverpa zea*), Southwestern Corn Borer (*Diatraea grandiosella*), Surgarcane Borer (*Diatraea saccharalis*), and Lesser Cornstalk Borer (*Elasmopalpus lignosellus*). In addition, the corn plant can be further defined as progeny of any generation of a corn plant comprising the corn event MON 95379.

Yet another embodiment of the invention is a method for protecting a corn plant from insect infestation, wherein said method comprises providing in the diet of a Lepidopteran insect pest an insecticidally effective amount of cells or tissue of a corn plant comprising corn event MON 95379. Again, contemplated Lepidopteran insect pests include Fall Armyworm (*Spodoptera frugiperda*), Corn Earworm (*Helicoverpa zea*), Southwestern Corn Borer (*Diatraea grandiosella*), Surgarcane Borer (*Diatraea saccharalis*), and Lesser Cornstalk Borer (*Elasmopalpus lignosellus*).

Another embodiment of the invention is a method of producing an insect resistant corn plant comprising: a) sexually crossing two different corn plants with at least one of the two different corn plants comprising transgenic corn event MON 95379 DNA; b) sampling seed or tissue from the progeny of step (a); c) detecting in said sample from step (b) progeny comprising corn event MON 95379 DNA; and d) selecting said progeny comprising corn event MON 95379 DNA.

A further embodiment of the invention is a corn seed, nonliving corn plant material, or a microorganism comprising a detectable amount of the nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, or complete complements thereof.

Yet another embodiment of the invention is a commodity product comprising a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, or complete complements thereof. Contemplated commodity products include whole or processed corn seed, animal feed comprising corn, corn oil, corn meal, corn flour, corn flakes, corn bran, corn biomass, and fuel products produced using corn and corn parts.

Another embodiment of the invention is a corn plant, corn plant part, or corn seed thereof comprising DNA functional as a template when tested in DNA amplification method producing an amplicon diagnostic for the presence of event MON 95379 DNA.

Yet another embodiment of the invention is a method of determining the zygosity of a corn plant or corn seed comprising event MON 95379 comprising: a) contacting a sample comprising corn DNA with a primer pair that is capable of producing an amplicon of one of the toxin coding sequences encoding Cry1B.868 or Cry1Da_7; b) contacting said sample comprising corn DNA with a primer pair that is capable of producing an amplicon of an internal standard known to be single-copy and homozygous in the corn plant; c) contacting the DNA sample with a probe set which contains at least a first probe that specifically hybridizes to one of the toxin coding sequences encoding Cry1B.868 or Cry1Da_7, and a second probe that specifically hybridizes to the internal standard genomic DNA known to be single-copy and homozygous in the corn plant; d) performing a DNA amplification reaction using real-time PCR and determining the cycle thresholds (Ct values) of the amplicon corresponding to the toxin coding sequence and the single-copy, homozygous internal standard; e) calculating the difference (ΔCt) between the Ct value of the single-copy, homozygous internal standard amplicon and the Ct value of the toxin coding sequence amplicon; and f) determining zygosity, wherein a ΔCt of about zero (0) indicates homozygosity of the inserted T-DNA of event MON 95739 and a ΔCt of about one (1) indicates heterozygosity of the inserted T-DNA of event MON 95379. In certain embodiments of this method, the primer pairs are selected from the group consisting of SEQ ID NO:18 combined with SEQ ID NO:19, and SEQ ID NO:21 combined with SEQ ID NO:22; and the probes are SEQ ID NO:20 and SEQ ID NO:23. In another embodiment, the primer pairs are selected from the group consisting of SEQ ID NO:18 combined with SEQ ID NO:19, and SEQ ID NO:24 combined with SEQ ID NO:25; and the probes are SEQ ID NO:20 and SEQ ID NO:26. In yet another embodiment of this invention the ΔCt of about one (1) indicating heterozygosity of the inserted T-DNA of event MON 95379 is in the range of 0.75 to 1.25.

A further embodiment of the invention is a method of determining the zygosity of a corn plant or corn seed comprising event MON 95379 comprising: a) contacting a sample comprising corn DNA with a set of primer pairs comprising at least two different primer pairs capable of producing a first amplicon diagnostic for event MON 95379 and a second amplicon diagnostic for native corn genomic DNA not comprising event MON 95379; i) performing a nucleic acid amplification reaction with the sample and the set of primer pairs; ii) detecting in the nucleic acid amplification reaction the first amplicon diagnostic for event MON 95379, or the second amplicon diagnostic for native corn genomic DNA not comprising event MON 95379, wherein the presence of only the first amplicon is diagnostic of a corn plant or corn seed homozygous for event MON 95379, and the presence of both the first amplicon and the second amplicon is diagnostic of a corn plant or corn seed heterozygous for event MON 95379; orb) contacting a sample comprising corn DNA with a probe set which contains at least a first probe that specifically hybridizes to event MON 95379 DNA and at least a second probe that specifically hybridizes to corn genomic DNA that was disrupted by insertion of the heterologous DNA of event MON 95379 and does not hybridize to event MON 95379 DNA; i) hybridizing the probe set with the sample under stringent hybridization conditions, wherein detecting hybridization of only the first probe under the hybridization conditions is diagnostic for a corn plant or corn seed homozygous for event MON 95379, and wherein detecting hybridization of both the first probe and the second probe under the hybridization conditions is diagnostic for a corn plant or a corn seed heterozygous for event MON 95379. In one embodiment of this method, the set of primer pairs comprises SEQ ID NO:15 combined with SEQ ID NO:16, and SEQ ID NO:15 combined with SEQ ID NO:27. In another embodiment of this method, the probe set comprises SEQ ID NO:17 and SEQ ID NO:28.

The forgoing and other aspects of the invention will become more apparent from the following detailed description.

BRIEF DESCRIPTION OF THE SEQUENCES

Figure 1:
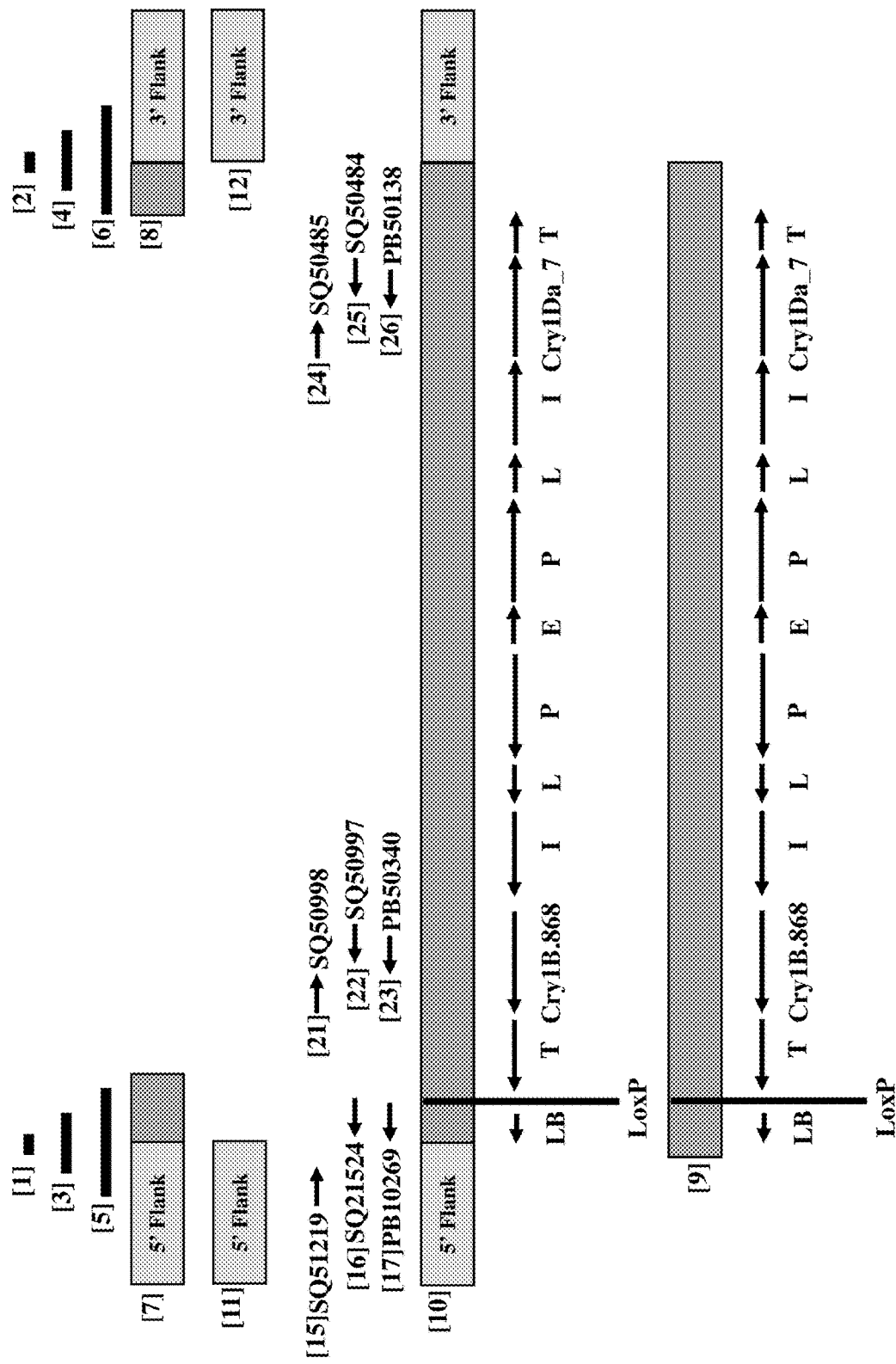
FIG. 1 represents the sequence of corn event MON 95379. Horizontal lines and boxes correspond to the positions of SEQ ID NO:1 ([1]), SEQ ID NO:2 ([2]), SEQ ID NO:3 ([3]), SEQ ID NO:4 ([4]), SEQ ID NO:5 ([5]), SEQ ID NO:6 ([6]), SEQ ID NO:7 ([7]), SEQ ID NO:8 ([8]), SEQ ID NO:9 ([9]), SEQ ID NO:11 ([11]), and SEQ ID NO:12 ([12]) relative to SEQ ID NO:10 ([10]). The horizontal arrows labeled SQ51219 (SEQ ID NO:15) ([15]), SQ21524 (SEQ ID NO:16) ([16]), SQ50998 (SEQ ID NO:21) ([21]), SQ50997 (SEQ ID NO:22) ([22]), SQ50485 (SEQ ID NO:24) ([24]) and SQ50484 (SEQ ID NO:25) ([25]) represent the approximate position of subsets of primers that can be used to detect corn event MON 95379. The horizontal arrows labeled PB10269 (SEQ ID NO:17) ([17]), PB50340 (SEQ ID NO:23) ([23]), PB50138 (SEQ ID NO:26) ([26]) represent the approximate position of a DNA probe that can be used to detect corn event MON 95379. "E" represents an enhancer element, "P" represents a promoter element, "L" represents a leader (5' UTR) element, "I" represents an intron element, "T" represents a 3' UTR, "Cry1B.868" represents the Cry1B.868 coding sequence element, "Cry1Da_7" represents the Cry1Da_7 coding sequence element, "LoxP" represents the site at which Cre-recombinase marker excision occurred, leaving behind one of the two LoxP sites after marker excision, and "LB" represents the left T-DNA border.

SEQ ID NO:1 is a 50 nucleotide sequence representing the 5' junction region of corn genomic DNA and the integrated transgenic expression cassette. SEQ ID NO:1 is found within SEQ ID NO:10 at nucleotide positions 838-887.

SEQ ID NO:2 is a 50 nucleotide sequence representing the 3' junction region of the integrated transgenic expression cassette and the corn genomic DNA. SEQ ID NO:2 is found within SEQ ID NO:10 at nucleotide positions 14,156-14,205.

SEQ ID NO:3 is a 100 nucleotide sequence representing the 5' junction region of corn genomic DNA and the integrated transgenic expression cassette. SEQ ID NO:3 is found within SEQ ID NO:10 at nucleotide positions 813-912.

SEQ ID NO:4 is a 100 nucleotide sequence representing the 3' junction region of the integrated transgenic expression cassette and the corn genomic DNA. SEQ ID NO:4 is found within SEQ ID NO:10 at nucleotide positions 14,131-14,230.

SEQ ID NO:5 is a 200 nucleotide sequence representing the 5' junction region of corn genomic DNA and the integrated transgenic expression cassette. SEQ ID NO:5 is found within SEQ ID NO:10 at nucleotide positions 763-962.

SEQ ID NO:6 is a 200 nucleotide sequence representing the 3' junction region of the integrated transgenic expression cassette and the corn genomic DNA. SEQ ID NO:6 is found within SEQ ID NO:10 at nucleotide positions 14,081-14,280.

SEQ ID NO:7 is a 1,160 nucleotide sequence representing the 5' junction region of corn genomic DNA and the integrated transgenic expression cassette. SEQ ID NO:7 is found within SEQ ID NO:10 at nucleotide positions 1-1,160.

SEQ ID NO:8 is a 1,178 nucleotide sequence representing the 3' junction region of the integrated transgenic expression cassette and the corn genomic DNA. SEQ ID NO:8 is found within SEQ ID NO:10 at nucleotide positions 14,039-15,216.

SEQ ID NO:9 is a 13,318 nucleotide sequence corresponding to the transgenic inserted T-DNA of corn event MON 95379.

SEQ ID NO:10 is a 15,216 nucleotide sequence corresponding to the contig nucleotide sequence of the 5' genomic flanking DNA nucleotide sequence, the inserted T-DNA nucleotide sequence in event MON 95379, and the 3' genomic flanking DNA nucleotide sequence; and includes SEQ ID NO:11 (nucleotides 1-862), SEQ ID NO:9 (nucleotides 863-14,180), and SEQ ID NO:12 (nucleotides 14,181-15,216).

SEQ ID NO:11 is an 862 nucleotide sequence representing the 5' flanking corn genomic DNA up to the inserted T-DNA. SEQ ID NO:11 is found within SEQ ID NO:10 at nucleotide positions 1-862.

SEQ ID NO:12 is a 1,036 nucleotide sequence representing the 3' flanking corn genomic DNA after the inserted T-DNA. SEQ ID NO:12 is found within SEQ ID NO:10 at nucleotide positions 14,181-15,216.

SEQ ID NO:13 is a 18,376 nucleotide sequence representing the transgene cassette comprised within the binary plasmid transformation vector used to transform corn to produce corn event MON 95379.

SEQ ID NO:14 is a 35 nucleotide sequence representing the LoxP sites used for Cre-mediated excision and recombination. A remaining LoxP site after marker excision can be found within SEQ ID NO:10 at nucleotide positions 1,080-1,114.

SEQ ID NO:15 is a 20 nucleotide sequence corresponding to a thermal amplification primer referred to as SQ51219 used to identify corn event MON 95379 DNA in a sample, and is identical to the nucleotide sequence corresponding to positions 833-852 of SEQ ID NO:10.

SEQ ID NO:16 is a 30 nucleotide sequence corresponding to a thermal amplification primer referred to as SQ21524 used to identify corn event MON 95379 DNA in a sample, and is identical to the reverse complement of the nucleotide sequence corresponding to positions 905-934 of SEQ ID NO:10.

SEQ ID NO:17 is a 16 nucleotide sequence corresponding to a probe referred to as PB10269 used to identify corn event MON 95379 DNA in a sample, and is identical to the reverse complement of the nucleotide sequence corresponding to positions 886-901 of SEQ ID NO:10.

SEQ ID NO:18 is a 24 nucleotide sequence corresponding to a thermal amplification primer referred to as SQ20222 used as an internal control for the event and zygosity assay for MON 95379 and hybridizes to a region of the corn genome.

SEQ ID NO:19 is a 28 nucleotide sequence corresponding to a thermal amplification primer referred to as SQ20221 used as an internal control for the event and zygosity assay for MON 95379 and hybridizes to a region of the corn genome.

SEQ ID NO:20 is a 29 nucleotide sequence corresponding to a probe referred to as PB50237 used as an internal control for the event and zygosity assay for MON 95379 and hybridizes to a region of the corn genome.

SEQ ID NO:21 is a 20 nucleotide sequence corresponding to a thermal amplification primer referred to as SQ50998 used in the zygosity assay for event MON 95379 and hybridizes to the coding sequence of Cry1B.868 within SEQ ID NO:10; and is identical to the nucleotide sequence corresponding to positions 2,809-2,828 of SEQ ID NO:10.

SEQ ID NO:22 is a 20 nucleotide sequence corresponding to a thermal amplification primer referred to as SQ50997 used in the zygosity assay for event MON 95379 and hybridizes to the coding sequence of Cry1B.868 within SEQ ID NO:10; and is identical to the reverse complement of the nucleotide sequence corresponding to positions 2,852-2,871 of SEQ ID NO:10.

SEQ ID NO:23 is an 18 nucleotide sequence corresponding to a probe referred to as PB50340 used in the zygosity assay for event MON 95379 and hybridizes to the coding sequence of Cry1B.868 within SEQ ID NO:10; and is identical to the reverse complement of the nucleotide sequence corresponding to positions 2,833-2,850 of SEQ ID NO:10.

SEQ ID NO:24 is a 19 nucleotide sequence corresponding to a thermal amplification primer referred to as SQ50485 used in the zygosity assay for event MON 95379 and hybridizes to the coding sequence of Cry1Da_7 within SEQ ID NO:10; and is identical to the nucleotide sequence corresponding to positions 12,820-12,838 of SEQ ID NO:10.

SEQ ID NO:25 is an 18 nucleotide sequence corresponding to a thermal amplification primer referred to as SQ50484 used in the zygosity assay for event MON 95379 and hybridizes to the coding sequence of Cry1Da_7 within SEQ ID NO:10; and is identical to the reverse complement of the nucleotide sequence corresponding to positions 12,855-12,872 of SEQ ID NO:10.

SEQ ID NO:26 is a 14 nucleotide sequence corresponding to a probe referred to as PB50138 used in the zygosity assay for event MON 95379 and hybridizes to the coding sequence of Cry1Da_7 within SEQ ID NO:10; and is identical to the reverse complement of the nucleotide sequence corresponding to positions 12,840-12,853 of SEQ ID NO:10.

SEQ ID NO:27 is a 21 nucleotide sequence corresponding to a thermal amplification primer referred to as PNEGDNA used in the zygosity assay for event MON 95379 and hybridizes to a region of corn genomic DNA which was deleted when the T-DNA used to produce event MON 95379 inserted into the corn genome. An amplicon derived from the combination of primers SQ51219 and PNEGDNA is diagnostic for the wild-type allele lacking the event MON 95379 inserted T-DNA.

SEQ ID NO:28 is a 14 nucleotide sequence corresponding to a probe referred to as PRBNEGDNA used in the zygosity assay for event MON 95379 and hybridizes to a region of corn genomic DNA which was deleted when the T-DNA used to produce event MON 95379 inserted into the corn genome.

DETAILED DESCRIPTION

The present invention provides a transgenic corn event—MON 95379—that achieves insecticidal control over Lepidopteran pests of corn by expression of Cry1B.868 and Cry1Da_7. Specifically, expression of the Cry1B.868 and Cry1Da_7 insect inhibitory proteins in corn event MON 95379 provides resistance to the Lepidopteran insect pests Fall Armyworm (*Spodoptera frugiperda*), Corn Earworm (*Helicoverpa zea*), Southwestern Corn Borer (*Diatraea grandiosella*), Surgarcane Borer (*Diatraea saccharalis*), and Lesser Cornstalk Borer (*Elasmopalpus lignosellus*). Event MON 95379 will meet a great need for control of these insects in the corn market, as chemical insecticides often do not provide adequate control of these insects, or require multiple applications over the growing season, increasing the input of chemical pesticides in the environment and adding cost to the production of corn.

It should be understood that reference to event MON 95379 is equivalent to reference to event MON95379; they are interchangeable and represent the same transgenic corn event.

Plant transformation techniques are used to insert foreign DNA (also known as transgenic DNA) randomly into a chromosome of the genome of a cell to produce a genetically engineered cell, also referred to as a "transgenic" or "recombinant" cell. Using this technique, many individual cells are transformed, each resulting in a unique "transgenic event" or "event" due to the random insertion of the foreign DNA into the genome. A transgenic plant is then regenerated from each individual transgenic cell. This results in every cell of the transgenic plant containing the uniquely inserted transgenic event as a stable part of its genome. This transgenic plant can then be used to produce progeny plants, each containing the unique transgenic event.

Figure 2:
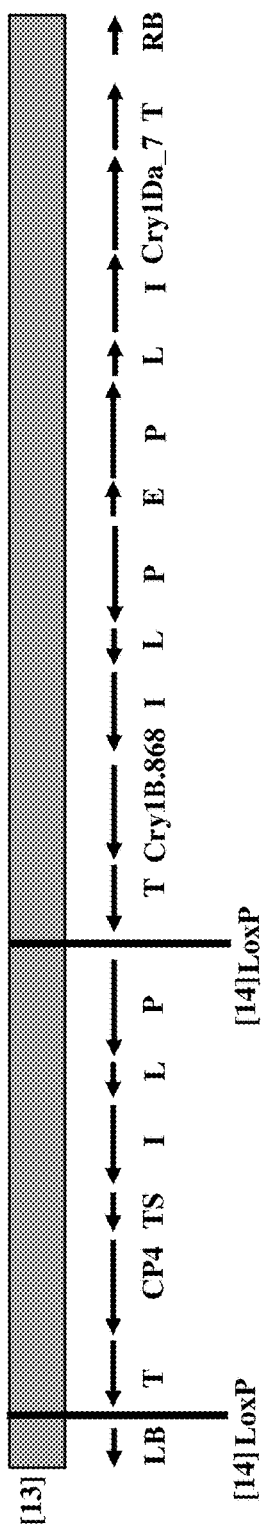
FIG. 2 is a diagrammatic representation of the T-DNA cassettes before integration to form event MON 95379, after integration, and after Cre-excision. The top horizontal box represents the T-DNA cassette in the plasmid vector used to transform event MON 95379, presented as SEQ ID NO:13 ([13]) ("T-DNA Before Integration"). The horizontal arrows below [13] represent the individual genetic elements comprised within the two transgene cassettes. "LB" represents a T-DNA left border element, "E" represents an enhancer element, "P" represents a promoter element, "L" represents a leader (5' UTR) element, "I" represents an intron element, "T" represents a 3' UTR, "Cry1B.868" represents the Cry1B.868 coding sequence element, "Cry1Da_7" represents the Cry1Da_7 coding sequence element, "CP4" represents the CP4 selectable marker, "TS" represented a targeting sequence, "LoxP" represents the site at which Cre-recombinase marker excision occurs, and "RB" represents a T-DNA right border element. The middle horizontal box, "Inserted T-DNA After Integration," represents the T-DNA cassette integrated into the corn genome after transformation wherein the right T-DNA border (RB) was lost during integration. The bottom horizontal box, "Inserted T-DNA After Cre-Excision," represents the integrated T-DNA cassette after the CP4 selectable marker cassette was excised, leaving behind one of the two LoxP sites and the LB region.
Figure 2:
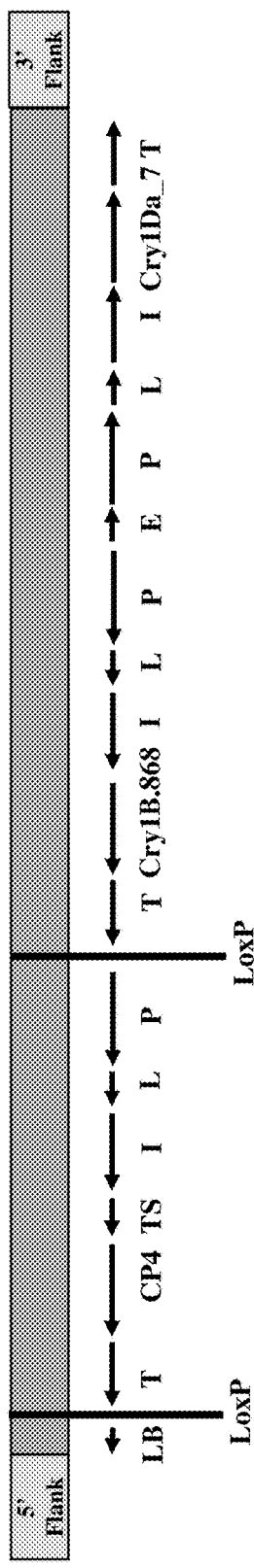
Figure 2:
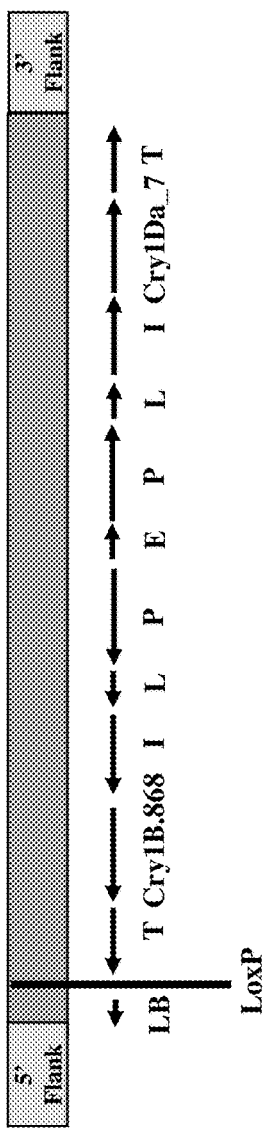

Corn event MON 95379 was produced by an *Agrobacterium*-mediated transformation process of corn immature embryos with a single T-DNA binary system. In this system, an *Agrobacterium* strain employing one binary plasmid vector with a single T-DNA was utilized. The T-DNA construct comprised two transgene cassettes for the expression of the insect toxin coding sequences encoding Cry1B 0.868 and Cry1Da_7, and a transgene cassette used for the selection of transformed corn cells using glyphosate selection (CP4). The T-DNA construct is SEQ ID NO:13, and illustrated in FIG. 2 ("T-DNA Before Integration"). During integration, the right T-DNA border was lost as shown in FIG. 2 ("Inserted T-DNA After Integration"). The glyphosate selection cassette was flanked on both sides with LoxP recognition sites which are recognized by Cre-recombinase, derived from Enterobacteria phage P1 (Larry Gilbertson (2003) *Cre-lox recombination: Cre-active tools for plant biotechnology. TRENDS in Biotechnology*, 21:12, 550-555).

As specifically described herein, corn event MON 95379 was produced by a complex research and development process in which: (1) hundreds of plasmid vector constructs—which varied with respect to the coding sequences for the insecticidal proteins, the coding sequences for the transcriptional regulatory elements, and number and orientation of the cassettes within the constructs—were developed and transformed into corn cells to create thousands of events that were tested and analyzed, resulting in the selection of the construct used to generate event MON 95379; (2) hundreds of corn cells were transformed with the construct used to generate event MON 95379, creating a population of transgenic plants in which each plant contained a unique transgenic event that was regenerated and tested; (3) the final event MON 95379 was selected after a rigorous multi-year event selection process involving the testing and analysis of molecular characteristics, efficacy, protein expression, and agronomic properties in a variety of genetic backgrounds; and (4) the glyphosate selection cassette in corn event MON 95379 was removed through in vivo Cre-excision to create a "marker-free" final event MON 95379. Corn event MON 95379 was thus produced and selected as a uniquely superior event useful for broad-scale agronomic purposes.

The plasmid DNA inserted into the genome of corn event MON 95379 was characterized by detailed molecular analysis. This analysis included: the insert number (number of integration sites within the corn genome), the genomic insert location (the specific site in the corn genome where the insertion occurred), the copy number (the number of copies of the T-DNA within one locus), and the integrity of the transgenic inserted DNA. The detailed molecular analysis demonstrated that the integrated T-DNA containing the Cry1B.868 and Cry1Da_7 expression cassettes remained intact after integration and Cre-excision of the glyphosate (CP4) selection cassette. As used herein, an "expression cassette" or "cassette" is a recombinant DNA molecule comprising a combination of distinct elements that are to be expressed by a transformed cell. Table 1 provides a list of the elements contained in SEQ ID NO:10, the DNA sequence that corresponds to corn event MON 95379.

TABLE 1

Description of corn event MON 95379

| Element | Position in SEQ ID NO: 10 | Description |
| --- | --- | --- |
| 5' Flanking DNA | 1-862 | DNA sequence flanking the 5' end of the transgenic insert. |
| Left Border Region | 863-1044 | DNA region from *Agrobacterium tumefaciens* containing the left border sequence. |
| LoxP | 1080-1114 | A recognition sequence for a site-specific recombinase from *Enterobacteria phage* P1. |
| T-Os.LTP:1 | 1225-1524 | The 3' untranslated region for a Lipid Transfer Protein-like gene (LTP) from *Oryza sativa* (rice). |
| Cry1B.868 | 1534-5133 | Coding sequence of a chimeric insect toxin comprised of domains 1 and 2 of Cry1Be2, domain 3 of Cry1Ca, and the protoxin domain of Cry1Ab3. |
| I-Zm.UbqM1-1:1:16 | 5160-6212 | An intron derived from an Ubiquitin 1 gene of *Zea mays Mexicana*. |
| L-Zm.UbqM1-1:1:4 | 6213-6290 | A 5' UTR derived from an Ubiquitin 1 gene of *Zea mays Mexicana*. |
| P-Zm.UbqM1-1:1:5 | 6291-7167 | A promoter derived from an Ubiquitin 1 gene of *Zea mays Mexicana*. |
| E-FMV.35S-1:1:2 | 7195-7731 | The enhancer of the 35S gene from Figwort Mosaic Virus (FMV). |
| P-SETit.Tip-1:1:1 | 7743-8659 | A promoter of a tonoplast membrane integral protein gene from *Setaria italica* (foxtail millet). |

TABLE 1-continued

Description of corn event MON 95379

| Element | Position in SEQ ID NO: 10 | Description |
|---|---|---|
| L-SETit.Tip-1:1:1 | 8660-8723 | A 5' UTR of a tonoplast membrane integral protein gene from *Setaria italica* (foxtail millet). |
| I-Os.Act15-1:1:1 | 8732-10024 | The first intron from the Actin 15 (Act 15) gene from *Oryza sativa* (rice). |
| Cry1Da_7 | 10043-13543 | Coding sequence of a Cry1Da insect toxin with amino acid modifications to improve efficacy. |
| T-Os.GOS2-1:1:1 | 13560-14027 | The 3' untranslated region from the GOS2 gene encoding a translation initiation factor from *Oryza sativa* (rice). |
| 3' Flanking Sequence | 14181-15216 | DNA sequence flanking the 3' end of the transgenic insert. |

Corn event MON 95379 is characterized as an insertion into a single locus in the corn genome, resulting in two new loci or junction sequences (e.g., sequences set forth in SEQ ID NO:1, SEQ ID NO:2, SEQ ID NO:3, SEQ ID NO:4, SEQ ID NO:5, SEQ ID NO:6, SEQ ID NO:7, and SEQ ID NO:8) spanning a portion of the inserted DNA and the corn genomic DNA that are not known to appear naturally in the corn genome or other transgenic corn events—they are unique to event MON 95379. These junction sequences are useful in detecting the presence of the event MON 95379 in corn cells, corn tissue, corn seed, and corn plants or corn plant products, such as corn commodity products. DNA molecular probes and primer pairs are described herein that have been developed for use in identifying the presence of these various junction segments in biological samples containing or suspected of containing corn cells, corn seed, corn plant parts, or corn plant tissue that contain the event MON 95379.

A sample is intended to refer to a composition that is either substantially pure corn DNA or a composition that contains corn DNA. In either case, the sample is a biological sample, i.e., it contains biological materials, including but not limited to DNA obtained or derived from, either directly or indirectly, the genome of corn event MON 95379. "Directly" refers to the ability of the skilled artisan to directly obtain DNA from the corn genome by fracturing corn cells (or by obtaining samples of corn that contain fractured corn cells) and exposing the genomic DNA for the purposes of detection. "Indirectly" refers to the ability of the skilled artisan to obtain the target or specific reference DNA, i.e., a novel and unique junction segment described herein as being diagnostic for the presence of the event MON 95379 in a particular sample, by means other than by obtaining directly via fracturing of corn cells or obtaining a sample of corn that contains fractured corn cells. Such indirect means include, but are not limited to, amplification of a DNA segment that contains the DNA sequence targeted by a particular probe designed to bind with specificity to the target sequence, or amplification of a DNA segment that can be measured and characterized, i.e., measured by separation from other segments of DNA through some efficient matrix such as an agarose or acrylamide gel or the like, or characterized by direct sequence analysis of the amplicons, or cloning of the amplicon into a vector and direct sequencing of the inserted amplicon present within such vector.

Detailed molecular analysis demonstrated that event MON 95379 contains a single T-DNA insertion with one copy of each of the Cry1B.868 and Cry1Da_7 expression cassettes. No additional elements from the transformation construct other than portions of the *Agrobacterium tumefaciens* left border region used for transgenic DNA transfer from the plant transformation plasmid to the corn genome were identified in event MON 95379. Finally, thermal amplification producing specific amplicons diagnostic for the presence of event MON 95379 in a sample and DNA sequence analyses were performed to determine the arbitrarily assigned 5' and 3' insert-to-plant genome junctions, confirm the organization of the elements within the insert, and determine the complete DNA sequence of the inserted transgenic DNA (SEQ ID NO:9). SEQ ID NO:11 is a sequence representing the eight hundred sixty-two (862) base-pair (bp) 5' LH244 corn genomic DNA sequence flanking the inserted T-DNA sequence presented as SEQ ID NO:9. SEQ ID NO:12 is a sequence representing the one thousand thirty-six (1,036) bp 3' LH244 corn genomic DNA sequence flanking the inserted T-DNA sequence presented as SEQ ID NO:9. SEQ ID NO:7 is a sequence representing the eight hundred sixty-two (862) base-pair (bp) 5' LH244 corn genomic DNA sequence flanking the inserted T-DNA sequence combined with two hundred ninety-eight (298) bp of inserted T-DNA sequence presented as SEQ ID NO:9. SEQ ID NO:8 is a sequence representing one hundred forty-two (142) bp of inserted T-DNA sequence with the one thousand thirty-six (1,036) bp 3' LH244 corn genomic DNA sequence flanking the inserted T-DNA sequence presented as SEQ ID NO:9. SEQ ID NO:10 corresponds to corn event MON 95379 and contains a contiguous sequence (contig) comprising the 5' LH244 flanking sequence, the transgene insert of event MON 95379, and the 3' LH244 flanking sequence, and thus contains the insert-to-plant genome junction sequences.

Unless otherwise noted herein, terms are to be understood according to conventional usage by those of ordinary skill in the relevant art. Definitions of common terms in molecular biology may be found in Rieger et al., Glossary of Genetics: Classical and Molecular, 5$^{th}$ edition, Springer-Verlag: New York, 1991; and Lewin, Genes V, Oxford University Press: New York, 1994, along with other sources known to those of ordinary skill in the art. As used herein, the term "corn" means species belong to the genus *Zea*, preferably *Zea mays* and includes all plant varieties that can be bred with corn plants containing event MON 95379, including wild corn species as well as those plants belonging to the genus *Zea* that permit breeding between species.

The present invention provides for transgenic plants which have been transformed with a DNA construct that contains expression cassettes expressing toxic amounts of the insecticidal proteins Cry1B.868 and Cry1Da_7. What is meant by toxic amount is an efficacious amount, an insecticidal amount, an insecticidally-effective amount, a target insect suppressive amount, an efficacious pesticidal amount, an amount in the diet of insects in the order of Lepidoptera that is insecticidal, and other similar terms to be understood according to conventional usage by those of ordinary skill in the relevant art. Corn plants transformed according to the methods and with the DNA construct disclosed herein are resistant to Lepidopteran insect pests.

A transgenic "plant" is produced by transformation of a plant cell with heterologous DNA, i.e., a polynucleic acid construct that includes a number of efficacious features of interest, regeneration of a plant resulting from the insertion of the transgene into the genome of the plant cell, and selection of a particular plant characterized by insertion into a particular genome location and the number of efficacious features of the regenerated transgenic plant. The term "event" refers to DNA from the original transformant comprising the inserted DNA, and flanking genomic sequences immediately adjacent to the inserted DNA. Such DNA is unique and would be expected to be transferred to a progeny that receives the inserted DNA, including the transgene of interest, as the result of a sexual cross of a parental line that includes the inserted DNA (e.g., the original transformant and progeny resulting from selfing) and a parental line that does not contain the inserted DNA. The present invention also provides the original transformant plant and progeny of the transformant that include the heterologous DNA. Such progeny may be produced by a sexual outcross between plants comprising the event and another plant wherein the progeny includes the heterologous DNA. Even after repeated back-crossing to a recurrent parent, the event is present in the progeny of the cross at the same chromosomal location.

As used herein, the term "recombinant" refers to a non-natural DNA, protein, or organism that would not normally be found in nature and was created by human intervention. A "recombinant DNA molecule" is a DNA molecule comprising a combination of DNA molecules that would not naturally occur together and is the result of human intervention. For example, a DNA molecule that is comprised of a combination of at least two DNA molecules heterologous to each other, such as a DNA molecule that comprises a transgene and the plant genomic DNA adjacent to the transgene, is a recombinant DNA molecule.

The terms "DNA" and "DNA molecule" referred to herein refer to a deoxyribonucleic acid (DNA) molecule. A DNA molecule may be of genomic or synthetic origin, and is by convention from the 5' (upstream) end to the 3' (downstream) end. As used herein, the term "DNA sequence" refers to the nucleotide sequence of the DNA molecule. By convention, the DNA sequences of the invention and fragments thereof are disclosed with reference to only one strand of the two strand complementary DNA sequence strands. By implication and intent, the complementary sequences of the sequences provided here (the sequences of the complementary strand), also referred to in the art as the reverse complementary sequences, are within the scope of the invention and are expressly intended to be within the scope of the subject matter claimed.

As used herein, the term "fragment" refers to a smaller piece of the whole. For example, fragments of SEQ ID NO:10 would include sequences that are at least about 12 consecutive nucleotides, at least about 13 consecutive nucleotides, at least about 14 consecutive nucleotides, at least about 15 consecutive nucleotides, at least about 16 consecutive nucleotides, at least about 17 consecutive nucleotides, at least about 18 consecutive nucleotides, at least about 19 consecutive nucleotides, at least about 20 consecutive nucleotides, at least about 25 consecutive nucleotides, at least about 30 consecutive nucleotides, at least about 35 consecutive nucleotides, at least about 40 consecutive nucleotides, at least about 45 consecutive nucleotides, at least about 50 consecutive nucleotides, at least about 60 consecutive nucleotides, at least about 70 consecutive nucleotides, at least about 80 consecutive nucleotides, at least about 90 consecutive nucleotides, or at least about 100 consecutive nucleotides of the complete sequence of SEQ ID NO:10.

Reference in this application to an "isolated DNA molecule" or an equivalent term or phrase is intended to mean that the DNA molecule is one that is present alone or in combination with other compositions, but not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" within the scope of this disclosure so long as the element is not within the genome of the organism and at the location within the genome in which it is naturally found. Similarly, a nucleotide sequence encoding an insecticidal protein or any naturally occurring insecticidal variant of that protein would be an isolated nucleotide sequence so long as the nucleotide sequence was not within the DNA of the bacterium from which the sequence encoding the protein is naturally found. A synthetic nucleotide sequence encoding the amino acid sequence of the naturally occurring insecticidal protein would be considered to be isolated for the purposes of this disclosure. For the purposes of this disclosure, any transgenic nucleotide sequence, i.e., the nucleotide sequence of the DNA inserted into the genome of the cells of a plant or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium. In any circumstance, the isolated DNA molecule is a chemical molecule, regardless of whether it is referred to as a nucleic acid, a nucleic acid sequence, a polynucleotide sequence, and the like. It is a novel, inventive molecule that exhibits industrial applicability both when present in a plant cell or in a plant genome, and when present outside of a plant cell, and therefore, exhibits and is intended to exhibit such utility regardless of where the molecule is located.

The DNA sequence of the region spanning the connection by phosphodiester bond linkage of one end of the transgenic insert to the flanking corn genomic DNA is referred to as a "junction." A junction is the connection point of the transgenic insert and flanking DNA as one contiguous molecule. One junction is found at the 5' end of the transgenic insert and the other is found at the 3' end of the transgenic insert, referred to herein as the 5' and 3' junction, respectively. A "junction sequence" refers to a DNA sequence of any length that spans the 5' or 3' junction of an event. Junction sequences of corn event MON 95379 are apparent to one of skill in the art using SEQ ID NO:10. Examples of junction sequences of event MON 95379 are provided as SEQ ID NOs:1-8. FIG. 1 illustrates the physical arrangement of the junction sequences, arranged from 5' to 3', relative to SEQ ID NO:10. The junction sequences of event MON 95379 may be present as part of the genome of a plant, seed, or cell containing event MON 95379. The identification of any one or more of the junction sequences in a sample from a plant, plant part, seed, or cell indicates that the DNA was obtained from corn containing event MON 95379, and is diagnostic for the presence of event MON 95379.

The junction sequences for event MON 95379 may be represented by a sequence from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:10. For example, the junction sequences may be arbitrarily represented by the nucleotide sequences provided as SEQ ID NO:1 and SEQ ID NO:2. Alternatively, the junction sequences may be arbitrarily represented by the nucleotide sequences provided as SEQ ID NO:3 and SEQ ID NO:4. Alternatively, the junction sequences may be arbitrarily represented by the nucleotide sequences provided as SEQ ID NO:5 and SEQ ID NO:6. Alternatively, the junction sequences may be arbitrarily represented by the nucleotide sequences provided as SEQ ID NO:7 and SEQ ID NO:8. These nucleotides are connected by phosphodiester linkage, and in corn event MON 95379 are present as part of the recombinant plant cell genome.

The identification of one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:10 in a sample derived from a corn plant, corn seed, or corn plant part is diagnostic that the DNA was obtained from corn event MON 95379. The invention thus provides a DNA molecule that contains at least one of the nucleotide sequences provided as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. Any segment of DNA derived from transgenic corn event MON 95379 that is sufficient to include at least one of the sequences provided as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10 is within the scope of the invention. In addition, any polynucleotide comprising a sequence complementary to any of the sequences described within this paragraph is within the scope of the invention.

The invention provides exemplary DNA molecules that can be used either as primers or probes for detecting the presence of DNA derived from a corn plant comprising event MON 95379 DNA in a sample. Such primers or probes are specific for a target nucleic acid sequence and, as such, are useful for the identification of corn event MON 95379 nucleic acid sequence by the methods of the invention described herein.

A "probe" is a nucleic acid molecule that is complementary to a strand of target nucleic acid and is useful in hybridization methods. A probe may be attached a conventional detectable label or reporter molecule, e.g., a radioactive isotope, ligand, chemiluminescent agent, or enzyme. Such a probe is complementary to a strand of a target nucleic acid and, in the case of the present invention, to a strand of DNA from event MON 95379 whether from an event MON 95379 containing plant or from a sample that includes event MON 95379 DNA. Probes according to the present invention include not only deoxyribonucleic or ribonucleic acids, but also polyamides and other probe materials that bind specifically to a target DNA sequence and can be used to detect the presence of that target DNA sequence. Exemplary DNA sequences useful as a probe for detecting corn event MON 95379 are provided as: SEQ ID NO:17 (PB10269), SEQ ID NO:23 (PB50340); SEQ ID NO:26 (PB50138).

A "primer" is typically a DNA molecule that is designed for use in specific annealing or hybridization methods that involve thermal amplification. A pair of primers may be used with template DNA (such as a sample of corn genomic DNA) in a thermal amplification (such as polymerase chain reaction (PCR)) to produce an amplicon, where the amplicon produced from such reaction would have a DNA sequence corresponding to sequence of the template DNA located between the two sites where the primers hybridized to the template.

A primer is typically designed to hybridize to a complementary target DNA strand to form a hybrid between the primer and target DNA strand, and the presence of the primer is a point of recognition by a polymerase to begin extension of the primer (i.e., polymerization of additional nucleotides into a lengthening nucleotide molecule) using as a template the target DNA strand. Primer pairs refer to use of two primers binding opposite strands of a double stranded nucleotide segment for the purpose of amplifying linearly the polynucleotide segment between the positions targeted for binding by the individual members of the primer pair, typically in a thermal amplification reaction or other conventional nucleic-acid amplification methods. Exemplary DNA molecules useful as primers are provided as SEQ ID NO:15, SEQ ID NO:16, SEQ ID NO:18, SEQ ID NO:19, SEQ ID NO:21, SEQ ID NO:22, SEQ ID NO:24, SEQ ID NO:25 and SEQ ID NO:27.

The primer pair SEQ ID NO:15 and SEQ ID NO:16 are useful as a first DNA molecule and a second DNA molecule that is different from the first DNA molecule, and both are each of sufficient length of contiguous nucleotides of SEQ ID NO:10 to function as DNA primers that, when used together in a thermal amplification reaction with template DNA derived from corn event MON 95379, to produce an amplicon diagnostic for corn event MON 95379 DNA in a sample. The primer pair SEQ ID NO:21 and SEQ ID NO:22 are useful as a first DNA molecule and a second DNA molecule that is different from the first DNA molecule, and both are each of sufficient length of contiguous nucleotides of SEQ ID NO:10 to function as DNA primers that, when used together in a thermal amplification reaction with template DNA derived from corn event MON 95379, to produce an amplicon diagnostic for the zygosity of corn event MON 95379 DNA in a sample. The primer pair SEQ ID NO:24 and SEQ ID NO:25 are useful as a first DNA molecule and a second DNA molecule that is different from the first DNA molecule, and both are each of sufficient length of contiguous nucleotides of SEQ ID NO:10 to function as DNA primers that, when used together in a thermal amplification reaction with template DNA derived from corn event MON 95379, to produce an amplicon diagnostic for the zygosity of corn event MON 95379 DNA in a sample. The primer pair SEQ ID NO:18 and SEQ ID NO:19 are useful as a first DNA molecule and a second DNA molecule that is different from the first DNA molecule, and both are each of sufficient length of contiguous nucleotides of a locus within the corn genome to function as DNA primers that, when used together in a thermal amplification reaction with template DNA derived from corn event MON 95379, to produce an amplicon that serves as an internal control for both the diagnosis of corn event MON 95379, as well as the zygosity of corn event MON 95379 DNA in a sample.

DNA probes and DNA primers are generally eleven (11) polynucleotides or more in length, often eighteen (18) polynucleotides or more, twenty-four (24) polynucleotides or more, or thirty (30) polynucleotides or more. Such probes and primers are selected to be of sufficient length to hybridize specifically to a target sequence under high stringency hybridization conditions. Preferably, probes and primers according to the present invention have complete sequence similarity with the target sequence, although probes differing from the target sequence that retain the ability to hybridize to target sequences may be designed by conventional methods.

The nucleic acid probes and primers of the present invention hybridize under stringent conditions to a target DNA molecule. Any conventional nucleic acid hybridization or amplification method can be used to identify the presence of DNA from a transgenic plant in a sample. Polynucleic acid molecules also referred to as nucleic acid segments or fragments thereof are capable of specifically hybridizing to other nucleic acid molecules under certain circumstances.

As used herein, two polynucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a polynucleic acid of the present invention will specifically hybridize to one or more of the nucleic acid molecules set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10, or complements thereof or fragments thereof under moderately stringent conditions, for example at about 2.0×SSC and about 65° C. In a particularly preferred embodiment, a nucleic acid of the present invention will specifically hybridize to one or more of the nucleic acid molecules set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, or SEQ ID NO:10, or complements or fragments thereof under high stringency conditions. In one aspect of the present invention, a preferred marker nucleic acid molecule of the present invention has the nucleic acid sequence set forth in SEQ ID NO:1, or SEQ ID NO:2, or SEQ ID NO:3, or SEQ ID NO:4, or SEQ ID NO:5, or SEQ ID NO:6, or SEQ ID NO:7, or SEQ ID NO:8, or SEQ ID NO:9, or SEQ ID NO:10, or complements thereof, or fragments thereof. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of polynucleic acid amplification method directed to a target polynucleic acid molecule that is part of a polynucleic acid template. For example, to determine whether a corn plant resulting from a sexual cross contains transgenic plant genomic DNA from a corn plant comprising event MON 95379 of the present invention, DNA that is extracted from a corn plant tissue sample may be subjected to a polynucleic acid amplification method using a primer pair that includes a first primer derived from a genomic DNA sequence in the region flanking the heterologous inserted DNA of event MON 95379 and is elongated by polymerase 5' to 3' in the direction of the inserted DNA. The second primer is derived from the heterologous inserted DNA molecule is elongated by the polymerase 5' to 3' in the direction of the flanking genomic DNA from which the first primer is derived. The amplicon may range in length from the combined length of the primer pair plus one nucleotide base pair, or plus about fifty nucleotide base pairs, or plus about two hundred-fifty nucleotide base pairs, or plus about four hundred-fifty nucleotide base pairs or more. Alternatively, a primer pair can be derived from genomic sequence on both sides of the inserted heterologous DNA so as to produce an amplicon that includes the entire insert polynucleotide sequence (e.g., a forward primer isolated from the genomic portion on the 5' end of SEQ ID NO:10 and a reverse primer isolated from the genomic portion on the 3' end of SEQ ID NO:10 that amplifies a DNA molecule comprising the inserted DNA sequence (SEQ ID NO:9) identified herein in the event MON 95379 genome). A member of a primer pair derived from the plant genomic sequence adjacent to the inserted transgenic DNA is located a distance from the inserted DNA sequence, this distance can range from one nucleotide base pair up to about twenty thousand nucleotide base pairs. The use of the term "amplicon" specifically excludes primer dimers that may be formed in the DNA thermal amplification reaction.

For practical purposes, one should design primers which produce amplicons of a limited size range, for example, between 100 to 1000 bases. Smaller (shorter polynucleotide length) sized amplicons in general are more reliably produced in thermal amplification reactions, allow for shorter cycle times, and can be easily separated and visualized on agarose gels or adapted for use in endpoint TAQMAN®-like assays. Smaller amplicons can be produced and detected by methods known in the art of DNA amplicon detection. In addition, amplicons produced using the primer pairs can be cloned into vectors, propagated, isolated, and sequenced or can be sequenced directly with methods well established in the art. Any primer pair derived from the combination of SEQ ID NO:11 and SEQ ID NO:9 or the combination of SEQ ID NO:12 and SEQ ID NO:9 that are useful in a DNA amplification method to produce an amplicon diagnostic for event MON 95379 or progeny thereof is an aspect of the invention. Any single isolated DNA polynucleotide primer molecule comprising at least 15 contiguous nucleotides of SEQ ID NO:11, or its complement that is useful in a DNA amplification method to produce an amplicon diagnostic for event MON 95379 or progeny thereof is an aspect of the invention. Any single isolated DNA polynucleotide primer molecule comprising at least 15 contiguous nucleotides of SEQ ID NO:12, or its complement that is useful in a DNA amplification method to produce an amplicon diagnostic for plants comprising event MON 95379 or progeny thereof is an aspect of the invention. Any single isolated DNA polynucleotide primer molecule comprising at least 15 contiguous nucleotides of SEQ ID NO:9, or its complement that is useful in a DNA amplification method to produce an amplicon diagnostic for event MON 95379 or progeny thereof is an aspect of the invention.

Polynucleic acid amplification can be accomplished by any of the various polynucleic acid amplification methods known in the art, including the polymerase chain reaction (PCR). Amplification methods are known in the art and are described, inter alia, in U.S. Pat. Nos. 4,683,195 and 4,683, 202 and in *PCR Protocols: A Guide to Methods and Applications*, ed. Innis et al., Academic Press, San Diego, 1990. PCR amplification methods have been developed to amplify up to 22 kb (kilobase) of genomic DNA and up to 42 kb of bacteriophage DNA (Cheng et al., *Proc. Natl. Acad. Sci. USA* 91:5695-5699, 1994). These methods as well as other methods known in the art of DNA amplification may be used in the practice of the present invention. The sequence of the heterologous DNA insert or flanking genomic DNA sequence from corn event MON 95379 can be verified (and corrected if necessary) by amplifying such DNA molecules from corn seed containing event MON 95379 DNA or corn plants grown from the corn seed containing event MON 95379 DNA deposited with the ATCC having accession No. PTA-125027, using primers derived from the sequences provided herein, followed by standard DNA sequencing of the PCR amplicon or cloned DNA fragments thereof.

The diagnostic amplicon produced by these methods may be detected by a plurality of techniques. One such method is Genetic Bit Analysis (Nikiforov, et al. Nucleic Acid Res. 22:4167-4175, 1994) where a DNA oligonucleotide is designed that overlaps both the adjacent flanking genomic DNA sequence and the inserted DNA sequence. The oligonucleotide is immobilized in wells of a microtiter plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labeled dideoxynucleotide triphosphates (ddNTPs) specific for the expected next base. Readout may be fluorescent or ELISA-based. A signal indicates presence of the transgene/genomic sequence due to successful amplification, hybridization, and single base extension.

Another method is the Pyrosequencing technique as described by Winge (Innov. Pharma. Tech. 00:18-24, 2000). In this method, an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene/genomic sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed that overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene/genomic sequence due to successful amplification, hybridization, and single base extension.

Real-time Polymerase Chain Reaction (PCR) is the ability to monitor the progress of the PCR as it occurs (i.e., in real time). Data is collected throughout the PCR process, rather than at the end of the PCR. In real-time PCR, reactions are characterized by the point in time during cycling when amplification of a target is first detected rather than the amount of target accumulated after a fixed number of cycles. In a real-time PCR assay, a positive reaction is detected by accumulation of a fluorescent signal. The higher the starting copy number of the nucleic acid target, the sooner a significant increase in fluorescence is observed. The cycle threshold (Ct value) is defined as the number of cycles required for the fluorescent signal to cross the threshold (i.e., exceeds background level). Ct levels are inversely proportional to the amount of target nucleic acid in the sample (i.e., the lower the Ct value, the greater the amount of target nucleic acid in the sample).

Taqman® (PE Applied Biosystems, Foster City, Calif.) is described as a method of detecting and quantifying the presence of a DNA sequence using real-time PCR and is fully understood in the instructions provided by the manufacturer. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermalstable polymerase and dNTPs. Hybridization of the FRET probe results in cleavage and release of the fluorescent moiety away from the quenching moiety on the FRET probe. A fluorescent signal indicates the presence of the transgene/genomic sequence due to successful amplification and hybridization.

Molecular Beacons have been described for use in sequence detection as described in Tyangi, et al. (Nature Biotech. 14:303-308, 1996). Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermalstable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

DNA detection kits that are based on DNA amplification methods contain DNA primer molecules that hybridize specifically to a target DNA and amplify a diagnostic amplicon under the appropriate reaction conditions. The kit may provide an agarose gel based detection method or any number of methods of detecting the diagnostic amplicon that are known in the art. DNA detection kits can be developed using the compositions disclosed herein and are useful for identification of corn event MON 95379 DNA in a sample and can be applied to methods for breeding corn plants containing event MON 95379 DNA. A kit that contains DNA primers that are homologous or complementary to any portion of the corn genomic region as set forth in SEQ ID NO:10 and to any portion of the inserted transgenic DNA as set forth in SEQ ID NO:10 is an object of the invention. The DNA molecules can be used in DNA amplification methods (PCR) or as probes in polynucleic acid hybridization methods, i.e., southern analysis, northern analysis. Kits of the invention may optionally also comprise reagents or instructions for performing the detection or diagnostic reactions described herein.

Probes and primers according to the invention may have complete sequence identity with the target sequence, although primers and probes differing from the target sequence that retain the ability to hybridize preferentially to target sequences may be designed by conventional methods. In order for a nucleic acid molecule to serve as a primer or probe it need only be sufficiently complementary in sequence to be able to form a stable double-stranded structure under the particular solvent and salt concentrations employed. Any conventional nucleic acid hybridization or amplification method can be used to identify the presence of transgenic DNA from corn event MON 95379 in a sample. Probes and primers are generally at least about 11 nucleotides, at least about 18 nucleotides, at least about 24 nucleotides, or at least about 30 nucleotides or more in length. Such probes and primers hybridize specifically to a target DNA sequence under stringent hybridization conditions. Conventional stringency conditions are described by Sambrook et al., 1989, and by Haymes et al., In: *Nucleic Acid Hybridization, A Practical Approach*, IRL Press, Washington, D.C. (1985).

Any number of methods well known to those skilled in the art can be used to isolate and manipulate a DNA molecule, or fragment thereof, disclosed in the invention, including thermal amplification methods. DNA molecules, or fragments thereof, can also be obtained by other techniques such as by directly synthesizing the fragment by chemical means, as is commonly practiced by using an automated oligonucleotide synthesizer.

The DNA molecules and corresponding nucleotide sequences provided herein are therefore useful for, among other things, identifying corn event MON 95379, detecting the presence of DNA derived from the transgenic corn event MON 95379 in a sample, and monitoring samples for the presence and/or absence of corn event MON 95379 or plant parts derived from corn plants comprising event MON 95379.

The invention provides corn plants, corn plant cells, corn seeds, corn plant parts (such as pollen, ovule, silk, spike, anther, cob, root tissue, stalk tissue, leaf tissue), corn progeny plants, and corn commodity products. These corn plants, corn plant cells, corn seeds, corn plant parts, corn progeny plants, and corn commodity products contain a detectable amount of a polynucleotide of the invention, e.g., such as a polynucleotide having at least one of the sequences provided as SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. Corn plants, plant cells, seeds, plant parts, and progeny plants of the invention may also contain one or more additional transgenes. Such additional transgene may be any nucleotide sequence encoding a protein or RNA molecule conferring a desirable trait including but not limited to increased insect resistance, increased water use efficiency, increased yield performance, increased drought resistance, increased seed quality, and/or increased herbicide tolerance.

The invention provides corn plants, corn plant cells, corn seeds, corn plant parts (such as pollen, ovule, silk, spike, anther, cob, root tissue, stalk tissue, leaf tissue), corn progeny plants derived from a transgenic corn plant containing event MON 95379 DNA. A representative sample of corn seed containing event MON 95379 DNA has been deposited according to the Budapest Treaty with the American Type Culture Collection (ATCC®). The ATCC repository has assigned the Patent Deposit Designation PTA-125027 to the seed containing event MON 95379 DNA.

The invention provides a microorganism comprising a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10 present in its genome. An example of such a microorganism is a transgenic plant cell. Microorganisms, such as a plant cell of the invention, are useful in many industrial applications, including but not limited to: (i) use as research tool for scientific inquiry or industrial research; (ii) use in culture for producing endogenous or recombinant carbohydrate, lipid, nucleic acid, or protein products or small molecules that may be used for subsequent scientific research or as industrial products; and (iii) use with modern plant tissue culture techniques to produce transgenic plants or plant tissue cultures that may then be used for agricultural research or production. The production and use of microorganisms such as transgenic plant cells utilizes modern microbiological techniques and human intervention to produce a man-made, unique microorganism. In this process, recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state. The transgenic plant cell's new genetic composition and phenotype is a technical effect created by the integration of the heterologous DNA into the genome of the cell. Another aspect of the invention is a method of using a microorganism of the invention. Methods of using microorganisms of the invention, such as transgenic plant cells, include (i) methods of producing transgenic cells by integrating recombinant DNA into the genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, or protein products from cultured cells; and (iv) methods of using modern plant tissue culture techniques with transgenic plant cells to produce transgenic plants or transgenic plant tissue cultures.

Plants of the invention may pass along the event MON 95379 DNA, including transgene inserted in corn event MON 95379, to progeny. As used herein, "progeny"

includes any plant, plant cell, seed, and/or regenerable plant part containing the event MON 95379 DNA derived from an ancestor plant and/or comprising a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. Plants, progeny, and seeds may be homozygous or heterozygous for the transgene of event MON 95379. Progeny may be grown from seeds produced by a corn event MON 95379 containing plant and/or from seeds produced by a plant fertilized with pollen from a corn event MON 95379 containing plant.

Progeny plants may be self-pollinated (also known as "selfing") to generate a true breeding line of plants, i.e., plants homozygous for the transgene. Selfing of appropriate progeny can produce plants that are homozygous for both added exogenous genes.

Alternatively, progeny plants may be out-crossed, e.g., bred with another unrelated plant, to produce a varietal or a hybrid seed or plant. The other unrelated plant may be transgenic or non-transgenic. A varietal or hybrid seed or plant of the invention may thus be derived by sexually crossing a first parent that lacks the specific and unique DNA of the corn event MON 95379 with a second parent comprising corn event MON 95379, resulting in a hybrid comprising the specific and unique DNA of the corn event MON 95379. Each parent can be a hybrid or an inbred/varietal, so long as the cross or breeding results in a plant or seed of the invention, i.e., a seed having at least one allele containing the DNA of corn event MON 95379 and/or a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. Two different transgenic plants may thus be crossed to produce hybrid offspring that contain two independently segregating, added, exogenous genes. For example, event MON 95379 containing Cry1B.868 and Cry1Da_7 conferring insect resistance to corn can be crossed with other transgenic corn plants to produce a plant having the characteristics of both transgenic parents. One example of this would be a cross of event MON 95379 containing Cry1B.868 and Cry1Da_7 conferring Lepidopteran resistance to corn with a plant having one or more additional traits such as herbicide tolerance, insect resistance, or drought tolerance, resulting in a progeny plant or seed that has resistance to Lepidopteran insect pests and has at least one or more additional traits. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987).

Plants, progeny, seeds, cells and plant parts of the invention may also contain one or more additional corn trait(s) or transgenic events, particularly those introduced by crossing a corn plant containing corn event MON 95379 with another corn plant containing the additional trait(s) or transgenic events. Such trait(s) or transgenic events include, but are not limited to, increased insect resistance, herbicide tolerance, increased water use efficiency, increased yield performance, increased drought resistance, increased seed quality, improved nutritional quality, hybrid seed production, or disease or fungal resistance. Corn transgenic events are known to those of skill in the art. For example, a list of such traits is provided by the United States Department of Agriculture's (USDA) Animal and Plant Health Inspection Service (APHIS) and can be found on their website: www.aphis.usda.gov. Two or more transgenic events may thus be combined in a progeny seed or plant by crossing two parent plants each comprising one or more transgenic events, collecting the progeny seed, and selecting for progeny seed or plants that contain the two or more transgenic events. These steps may be repeated until the desired combination of transgenic events in a progeny is achieved. Back-crossing to a parental plant and out-crossing with a non-transgenic plant are also contemplated, and is vegetative propagation.

The invention provides a plant part that is derived from corn plants comprising event MON 95379. As used herein, a "plant part" refers to any part of a plant which is comprised of material derived from a corn plant comprising event MON 95379. Plant parts include but are not limited to pollen, ovule, silk, spike, anther, cob, root tissue, stalk tissue, and leaf tissue. Plant parts may be viable, nonviable, regenerable, and/or nonregenerable.

The invention provides a commodity product that is derived from corn plants comprising event MON 95379 and that contains a detectable amount of a nucleic acid specific for event MON 95379. As used herein, a "commodity product" refers to any composition or product which is comprised of material derived from a corn plant, whole or processed corn seed, or one or more plant cells and/or plant parts containing the corn event MON 95379 DNA. Nonviable commodity products include but are not limited to nonviable seeds, whole or processed seeds, seed parts, and plant parts; animal feed comprising corn, corn oil, corn meal, corn flour, corn flakes, corn bran, pasta made with corn, corn biomass, and fuel products produced using corn and corn parts. Viable commodity products include but are not limited to seeds, plants, and plant cells. The corn plants comprising event MON 95379 can thus be used to manufacture any commodity product typically acquired from corn. Any such commodity product that is derived from corn plants comprising event MON 95379 may contain at least a detectable amount of the specific and unique DNA corresponding to corn event MON 95379, and specifically may contain a detectable amount of a polynucleotide comprising a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. Any standard method of detection for nucleotide molecules may be used, including methods of detection disclosed herein. A commodity product is with the scope of the invention if there is any detectable amount of a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10 in the commodity product.

The corn plants, corn plant cells, corn seeds, corn plant parts (such as pollen, ovule, silk, spike, anther, cob, root tissue, stalk tissue, leaf tissue), corn progeny plants, and commodity products of the invention are therefore, useful for, among other things, growing plants for the purpose of producing seed and/or plant parts comprising corn event MON 95379 for agricultural purposes, producing progeny comprising corn event MON 95379 for plant breeding and research purposes, use with microbiological techniques for industrial and research applications, and sale to consumers.

Methods for producing an insect resistant corn plant comprising the DNA sequences specific and unique to event MON 95379 of the invention are provided. Transgenic plants used in these methods may be homozygous or heterozygous for the transgene. Progeny plants produced by these methods may be varietal or hybrid plants; may be grown from seeds produced by corn event MON 95379 containing plant and/or from seeds produced by a plant fertilized with pollen from a corn event MON 95379 containing plant; and may be homozygous or heterozygous for the transgene. Progeny plants may be subsequently self-pollinated to generate a true breeding line of plants, i.e., plants homozygous for the transgene, or alternatively may be out-crossed, e.g., bred with another unrelated plant, to produce a varietal or a hybrid seed or plant.

Methods of detecting the presence of DNA derived from a corn cell, corn tissue, corn seed, or corn plant comprising corn event MON 95379 in a sample are provided. One method consists of (i) extracting a DNA sample from at least one corn cell, corn tissue, corn seed, or corn plant; (ii) contacting the DNA sample with at least one primer that is capable of producing DNA sequence specific to event MON 95379 DNA under conditions appropriate for DNA sequencing; (iii) performing a DNA sequencing reaction; and then (iv) confirming that the nucleotide sequence comprises a nucleotide sequence specific for event MON 95379, of the construct comprised therein, such as one selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. Another method consists of (i) extracting a DNA sample from at least one corn cell, corn tissue, corn seed, or corn plant; (ii) contacting the DNA sample with a primer pair that is capable of producing an amplicon from event MON 95379 DNA under conditions appropriate for DNA amplification; (iii) performing a DNA amplification reaction; and then (iv) detecting the amplicon molecule and/or confirming that the nucleotide sequence of the amplicon comprises a nucleotide sequence specific for event MON 95379, such as one selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. The amplicon should be one that is specific for event MON 95379, such as an amplicon that comprises SEQ ID NO:1, or SEQ ID NO:2, or SEQ ID NO:3, or SEQ ID NO:4, or SEQ ID NO:5, or SEQ ID NO:6, or SEQ ID NO:7, or SEQ ID NO:8, or SEQ ID NO:9, or SEQ ID NO:10. The detection of a nucleotide sequence specific for event MON 95379 in the amplicon is determinative and/or diagnostic for the presence of the corn event MON 95379 specific DNA in the sample. An example of a primer pair that is capable of producing an amplicon from event MON 95379 DNA under conditions appropriate for DNA amplification is provided as SEQ ID NO:15 and SEQ ID NO:16. Other primer pairs may be readily designed by one of skill in the art and would produce an amplicon comprising SEQ ID NO:1, or SEQ ID NO:2, or SEQ ID NO:3, or SEQ ID NO:4, or SEQ ID NO:5, or SEQ ID NO:6, or SEQ ID NO:7, or SEQ ID NO:8 wherein such a primer pair comprises at least one primer within the genomic region flanking the insert and a second primer within the insert. Another method of detecting the presence of DNA derived from a corn cell, corn tissue, corn seed, or corn plant comprising corn event MON 95379 in a sample consists of (i) extracting a DNA sample from at least one corn cell, corn tissue, corn seed, or corn plant; (ii) contacting the DNA sample with a DNA probe specific for event MON 95379 DNA; (iii) allowing the probe and the DNA sample to hybridize under stringent hybridization conditions; and then (iv) detecting hybridization between the probe and the target DNA sample. An example of the sequence of a DNA probe that is specific for event MON 95379 is provided as SEQ ID NO:17. Other probes may be readily designed by one of skill in the art and would comprise at least one fragment of genomic DNA flanking the insert and at least one fragment of insert DNA such as the sequence provided in SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:10. Detection of probe hybridization to the DNA sample is diagnostic for the presence of corn event MON 95379 specific DNA in the sample. Absence of hybridization is alternatively diagnostic of the absence of corn event MON 95379 specific DNA in the sample.

DNA detection kits are provided that are useful for the identification of corn event MON 95379 DNA in a sample and can also be applied to methods for breeding corn plants containing the appropriate event DNA. Such kits contain DNA primers and/or probes comprising fragments of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. One example of such a kit comprises at least one DNA molecule of sufficient length of continuous nucleotides of SEQ ID NO:10 to function as a DNA probe useful for detecting the presence and/or absence of DNA derived from transgenic corn plants comprising event MON 95379 in a sample. The DNA derived from transgenic corn plants comprising event MON 95379 would comprise a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. A DNA molecule sufficient for use as a DNA probe is provided that is useful for determining, detecting, or diagnosing the presence and/or absence of corn event MON 95379 DNA in a sample is provided as SEQ ID NO: 17. Other probes may be readily designed by one of skill in the art and should comprise at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, or at least 40 contiguous nucleotides of SEQ ID NO:10 and be sufficiently unique to corn event MON 95379 DNA in order to identify DNA derived from the event.

Another type of kit comprises a primer pair useful for producing an amplicon useful for detecting the presence and/or absence of DNA derived from transgenic corn event MON 95379 in a sample. Such a kit would employ a method comprising contacting a target DNA sample with a primer pair as described herein, then performing a nucleic acid amplification reaction sufficient to produce an amplicon comprising a DNA molecule having at least one sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10 and then detecting the presence and/or absence of the amplicon. Such a method may also include sequencing the amplicon or a fragment thereof, which would be determinative of, i.e., diagnostic for, the presence of the corn event MON 95379 specific DNA in the target DNA sample. Other primer pairs may be readily designed by one of skill in the art and should comprise at least 15, at least 16, at least 17, at least 18, at least 19, at least 20, at least 21, at least 22, at least 23, at least 24, at least 25, at least 26, at least 27, at least 28, at least 29, or at least 30 contiguous nucleotides of sequences provided in, but not limited to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10, and be sufficiently unique to corn event MON 95379 DNA in order to identify DNA derived from the event.

The kits and detection methods of the invention are useful for, among other things, identifying corn event MON 95379, selecting plant varieties or hybrids comprising corn event MON 95379, detecting the presence of DNA derived from the transgenic corn plant comprising event MON 95379 in a sample, and monitoring samples for the presence and/or absence of corn plants comprising event MON 95379, or plant parts derived from corn plants comprising event MON 95379.

The sequences of the heterologous DNA insert, junction sequences, or flanking sequence from corn event MON 95379 can be verified (and corrected if necessary) by amplifying such sequences from the event using primers derived from the sequences provided herein followed by standard DNA sequencing of the amplicon or of the cloned DNA.

Methods of detecting the zygosity of the transgene allele of DNA derived from a corn cell, corn tissue, corn seed, or corn plant comprising corn event MON 95379 in a sample are provided. One method consists of (i) extracting a DNA sample from at least one corn cell, corn tissue, corn seed, or corn plant; (ii) contacting the DNA sample with a primer pair that is capable of producing a first amplicon diagnostic for event MON 95379; (iii) contacting the DNA sample with a primer pair that is capable of producing a second amplicon diagnostic for native corn genomic DNA not comprising event MON 95379; (iv) performing a DNA amplification reaction; and then (v) detecting the amplicons, wherein the presence of only the first amplicon is diagnostic of a homozygous event MON 95379 DNA in the sample, and the presence of both the first amplicon and the second amplicon is diagnostic of a corn plant heterozygous for event MON 95379 allele. An exemplary set of primers pairs are presented as SEQ ID NO:15 and SEQ ID NO:16 which produce an amplicon diagnostic for event MON 95379; and SEQ ID NO:15 and SEQ ID NO:27 which produces an amplicon diagnostic for non-inserted wild-type corn genomic DNA not comprising event MON 95379. A set of probes can also be incorporated into such an amplification method to be used in a real-time PCR format using the primer pair sets described above. An exemplary set of probes are presented as SEQ ID NO:17 (diagnostic for the amplicon for the event MON 95379) and SEQ ID NO:28 (diagnostic for the amplicon for wild-type corn genomic DNA not comprising event MON 95379).

Another method for determining zygosity consists of (i) extracting a DNA sample from at least one corn cell, corn tissue, corn seed, or corn plant; (ii) contacting the DNA sample with a probe set which contains at least a first probe that specifically hybridizes to event MON 95379 DNA and at least a second probe that specifically hybridizes to corn genomic DNA that was disrupted by insertion of the heterologous DNA of event MON 95379 and does not hybridize to event MON 95379 DNA; (iii) hybridizing the probe set with the sample under stringent hybridization conditions, wherein detecting hybridization of only the first probe under the hybridization conditions is diagnostic for a homozygous allele of event MON 95379 DNA in the sample; and wherein detecting hybridization of both the first probe and the second probe under the hybridization conditions is diagnostic for a heterozygous allele of event MON 95379 in a DNA sample.

Yet another method for determining zygosity consists of (i) extracting a DNA sample from at least one corn cell, corn tissue, corn seed, or corn plant; (ii) contacting the DNA sample with a primer pair that is capable of producing an amplicon of one of the toxin coding sequences encoding Cry1B.868 or Cry1Da_7; (iii) contacting the DNA sample with a primer pair that is capable of producing an amplicon of an internal standard known to be single-copy and homozygous in the corn plant; (iv) contacting the DNA sample with a probe set which contains at least a first probe that specifically hybridizes to one of the toxin coding sequences encoding Cry1B.868 or Cry1Da_7, and at least a second probe that specifically hybridizes to the internal standard genomic DNA known to be single-copy and homozygous in the corn plant; (v) performing a DNA amplification reaction using real-time PCR and determining the cycle thresholds (Ct values) of the amplicon corresponding to the toxin coding sequence and the single-copy, homozygous internal standard; (vi) calculating the difference ($\Delta$Ct) between the Ct value of the single-copy, homozygous internal standard amplicon and the Ct value of the toxin coding sequence amplicon; and (vii) determining zygosity, wherein a $\Delta$Ct of around zero (0) indicates homozygosity of the inserted T-DNA and a $\Delta$Ct of around one (1) indicates heterozygosity of the inserted T-DNA. Heterozygous and homozygous events are differentiated by a $\Delta$Ct value unit of approximately one (1). Given the normal variability observed in real-time PCR due to multiple factors such as amplification efficiency and ideal annealing temperatures, the range of "about one (1)" is defined as a $\Delta$Ct of 0.75 to 1.25. Primer pairs and probes for the above method for determining zygosity can either amplify and detect amplicons from the Cry1B.868 coding sequence and internal standard, or amplify and detect amplicons from the Cry1Da_7 coding sequence and internal standard. Exemplary primer pairs for the detection of the amplicons corresponding to the Cry1B.868 coding sequence and internal standard are presented as SEQ ID NO:18 combined with SEQ ID NO:19 (internal standard) and SEQ ID NO:21 combined with SEQ ID NO:22 (Cry1B.868). The accompanying exemplary probes are presented as SEQ ID NO:20 (internal standard) and SEQ ID NO:23 (Cry1B.868). Exemplary primer pairs for the detection of the amplicons corresponding to the Cry1Da_7 coding sequence and internal standard are presented as SEQ ID NO:18 combined with SEQ ID NO:19 (internal standard) and SEQ ID NO:24 combined with SEQ ID NO:25 (Cry1Da_7). The accompanying exemplary probes are presented as SEQ ID NO:20 (internal standard) and SEQ ID NO:26 (Cry1Da_7).

Deposit Information

A deposit of a representative sample of corn seed containing event MON 95379 was made on Apr. 20, 2018 according to the Budapest Treaty with the American Type Culture Collection (ATCC) having an address at 10801 University Boulevard, Manassas, Va. USA, Zip Code 20110, and assigned ATCC Accession No. PTA-125027. Access to the deposits will be available during the pendency of the application to the Commissioner of Patents and Trademarks and persons determined by the Commissioner to be entitled thereto upon request. Upon issuance of the patent, all restrictions upon availability to the public will be irrevocably removed. The deposit has been accepted under the Budapest Treaty and will be maintained in the depository for a period of thirty (30) years, or five (5) years after the last request, or for the effective life of the patent, whichever is longer, and will be replaced as necessary during that period.

EXAMPLES

The following Examples are included to more fully describe the invention. Summarized are the construction and testing of one hundred and twenty-five (125) constructs, the production of about ten thousand seven hundred and eighty-five (10,785) events (both proof of concept and commercial), and the analysis of hundreds of thousands of individual plants over six (6) years through the rigorous molecular, agronomic, and field testing required for the creation and selection of corn event MON 95379.

The Examples demonstrate certain preferred embodiments of the invention. It should be appreciated by those of skill in the art that the techniques disclosed in the Examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

Example 1

Expression Cassette Testing, Construct Design, Plant Testing and Construct Selection Transgene expression in plants is influenced by numerous different factors. The right combination of insecticidal proteins and different expression elements driving expression in plants, while not resulting in off-phenotypes, must be found. Further, beyond the expression elements themselves and their combination and orientation in a cassette, the expression of transgenes in plants is known to be influenced by chromosomal insertion position, perhaps due to chromatin structure (e.g., heterochromatin) or the proximity of transcriptional regulation elements (e.g., enhancers) close to the integration site (Kurt Weising et al., (1988) *Foreign genes in plants: transfer, structure, expression and applications. Annu. Rev. Genet.* 22: 421-77). For example, it has been observed in plants and in other organisms that there may be wide variation in the levels of expression of an introduced gene from the same construct among events with different chromosomal insertion positions. Different chromosomal insertion positions may also produce differences in spatial or temporal patterns of expression, that may not correspond to the patterns expected from transcriptional regulatory elements present in the introduced gene construct.

For these reasons, it is often necessary to create and screen a large number of constructs and transformation events in order to identify a construct, and then an event, which demonstrates optimal expression of the introduced genes of interest, while also not producing agronomic or phenotypic off-types.

For these reasons, the development of a transgenic corn plant comprising insecticidal proteins that were active against Lepidopterans without any negative effects on agronomics, yield, or stacking viability required extensive research, development, and analysis. Specifically, over a six (6) year period, approximately ten thousand, seven hundred eight-five (10,785) proof of concept and commercial transgenic events derived from one hundred twenty-five (125) different plasmid vector constructs were developed, tested, and analyzed.

This Example describes the design and testing in corn plants of one hundred and twenty five (125) different constructs to identify the preferred construct for event creation. Each construct varied with respect to the coding sequences for the insecticidal proteins and the transcriptional regulatory elements. Testing was done to select the best construct for use in expressing the insecticidal proteins in plants. Each construct had a unique configuration, varying by expression cassette composition (both insecticidal proteins and expression elements), orientation, and whether or not proteins were targeted to the chloroplast.

In an initial proof of concept and developmental stage, one hundred seventeen (117) constructs comprising different combinations of twenty-six (26) distinct promoters, twenty-six (26) distinct introns, and ten (10) distinct insect toxin coding sequences, were used to generate approximately six thousand (6,000) transformed events. After initial molecular characterization for the presence of the transgene(s), five thousand fifty-two (5,052) single and double-copy transformed corn events were selected for further characterization and efficacy testing. These events were evaluated for phenotypic or agronomic off-types, the level of expression of the insect toxin proteins, and efficacy against selected Lepidopteran insect pest species. The resulting efficacy and protein expression data, along with any information regarding phenotypic and agronomic off-types was used to eliminate inefficacious proteins, expression elements and combinations, and was used to design a smaller number of binary commercial transformation plasmid constructs to be used in the next phase of development.

In the next phase of development, eight (8) new constructs were created. These constructs comprised combinations of two (2) to four (4) insect toxin transgene expression cassettes in different orientations (convergent or divergent). These eight (8) constructs were used to generate a total of five thousand seven hundred thirty-three (5,733) transformed events (also referred to as "transformants"). After shoot formation in culture, a subset of the transformed events were selected based upon visual characteristics and early molecular analysis. A total of eight hundred twenty-three (823) transformed events were selected and transplanted to pots and grown for further study.

The resulting $R_0$ generation transformed events were analyzed for efficacy against selected Lepidopteran species, toxin protein expression, plant health, seed return, and phenotypic and agronomic off-types. The $R_0$ generation events were also characterized molecularly to ensure cassette intactness and proper insertion in the corn genome. Many of the events were dropped from testing due to failure to pass the agronomic analysis and molecular characterization testing. In addition, one (1) of the eight (8) constructs was dropped from further study at this $R_0$ stage because it produced events with off-phenotypes. In addition to these agronomic problems, later mode of action ("MOA") studies conducted demonstrated that an insect toxin protein contained in this construct demonstrated an overlapping MOA to a commercially-available protein.

Mode of Action studies were conducted on one of the insect proteins common to four (4) of the eight (8) constructs. These studies demonstrated that this insect protein had an overlapping MOA to a commercially-available protein. Proteins that demonstrate an analogous or overlapping MOA to a currently utilized commercial insecticidal protein are not desirable because of resistance development, which could render a protein with a similar MOA ineffective against insect populations. As such, these four (4) constructs, and the events arising therefrom, were dropped. As noted previously, one (1) of the four (4) dropped constructs also produced events with off-phenotypes at the $R_0$ stage.

In the next stage of development, one hundred fifty (150) events derived from the remaining four (4) constructs were further evaluated at the $F_1$ (heterozygous hybrid)/$R_1$ (homozygous inbred) and $R_2$ generation for efficacy, seed return and segregation, phenotypic and agronomic off-types, and further molecular characterization. Two (2) constructs from the remaining four (4) constructs were dropped from further study in this stage for failure to meet one or more of the criteria for advancement, leaving events derived from (2) constructs for further evaluation.

Seventy-seven (77) events, forty-one (41) derived from the construct used to generate event MON 95379 ("Construct MON95") and thirty-six (36) events derived from the other construct ("Construct 1"), were evaluated as $R_2$ inbreds and $F_1$ hybrids for efficacy, seed return and segregation, phenotypic and agronomic off-types and further molecular characterization. Based upon the results of these evaluations, events associated with Construct 1 were de-prioritized, shelved and stored.

Thus, numerous rounds of testing and comparison of various constructs revealed that the transgene cassette provided as SEQ ID NO:13, Construct MON95, was the best option for efficacy against the Lepidopteran pest species Fall Armyworm (FAW, Spodoptera frugiperda), Corn Earworm (CEW, Helicoverpa zea), Southwestern Corn Borer (SWCB, Diatraea grandiosella), Surgarcane Borer (SCB, Diatraea saccharalis), and Lesser Cornstalk Borer (LSCB, Elasmopalpus lignosellus), with the best molecular characterization and agronomic performance.

Table 2 illustrates the number of transformed events derived ("Plugged"), the number of transformed events selected for growth as R0 events ("Transplanted"), and the points at which each respective construct was dropped in the evaluation, research and development process that led to the selection of Construct MON95.

TABLE 2

Event construct selection.

| Construct | Plugged | Transplanted | Dropped |
|---|---|---|---|
| Construct MON 95 | 1202 | 210 | |
| Construct 1 | 799 | 173 | Shelved based on $R_2$ and $F_1$ data |
| Construct 2 | 679 | 113 | $R_2/F1/R_1$ |
| Construct 3 | 1344 | 20 | $MOA/R_0$ |
| Construct 4 | 232 | 41 | $R_2/F_1/R_1$ |
| Construct 5 | 544 | 88 | MOA |
| Construct 6 | 584 | 95 | MOA |
| Construct 7 | 349 | 83 | MOA |

Example 2

Field Trials, Molecular Testing and Event Selection

This Example describes the molecular characterization, analysis, and testing in field trials of events created with Construct MON95 in multiple locations over several years, which lead to the selection of the final event, MON 95379.

Table 3 illustrates the process used to select the final event, MON 95379. At the commercial transformation $R_0$ screen, two hundred ten (210) $R_0$ transformed events from Construct MON95 were derived and selected for growth. Of the initial two hundred ten (210) selected $R_0$ transformed events, one hundred forty-seven events (147) were dropped due to concerns regarding efficacy, protein expression, seed return and plant health, or molecular characterization. This left sixty-three (63) events for assay and testing in the next stage of development, the $F_1$ Screen and the $R_1$ Nursery stage. In this stage, eleven (11) events were dropped due to efficacy concerns in the greenhouse testing. Another three (3) events were dropped because of insufficient return of seed from the nursery and/or segregation analysis of the resulting seed. Finally, another five (5) events were removed due to issues discovered in molecular characterization and three (3) events were removed due to issues discovered in molecular southern analysis, leaving forty-one (41) events for assay in the next generation. At the $R_2/F_1$ stage of testing, two (2) of the remaining forty-one (41) events were dropped due to issues discovered in further molecular southern characterization, leaving thirty-nine (39) events.

The remaining thirty-nine (39) events were advanced in two different concurrent parallel testing stages: 1) further field trials; and 2) Cre-excision of the selection cassette and the production of gold standard seed. Events were dropped in each of these concurrent parallel testing stages.

During Cre-excision, eleven (11) events were dropped due to issues discovered in molecular characterization after cre-excision of the glyphosate selection cassette. Further, another six (6) events were dropped due to issues discovered in molecular characterization during gold standard seed production.

During the concurrent field testing, based on data collected from the 2016 U.S. Field Trails, another four (4) events were dropped due to efficacy concerns and another twelve (12) events were dropped due to agronomic concerns. Then, based on data collected from the Brazil Field Trials, another event was dropped due to efficacy concerns. Next, bioinformatic analysis conducted during the 2017 U.S. Field Trials resulted in the removal of another three (3) events from further testing, leaving two events: Event 1 and MON 95379. After further analysis of the agronomics of the events from multiple field trials in the U.S., Brazil, Argentina and Puerto Rico, event MON 95379 was selected as the event for commercialization because it ranked higher than Event 1 when all the characteristics of molecular characterization, protein expression, efficacy and agronomics of each event were compared.

TABLE 3

MON 95379 event selection.

| Stage | Assay | Events Removed | Events Remaining 210 |
|---|---|---|---|
| Comm. TFN $R_0$ Screen | Efficacy | 21 | 63 |
| | Expression | 6 | |
| | Seed Return/plant health | 51 | |
| | Molecular characterization | 69 | |
| $R_1/F_1$ | Greenhouse Efficacy | 11 | 41 |
| | Molecular characterization | 5 | |
| | Nursery return/segregation | 3 | |
| | Molecular southern | 3 | |
| $R_2/F_1$ | Molecular southern | 2 | 39 |
| Cre Excision | Molecular characterization after CP4 excision | 11 | 28 |
| Gold Standard Seed | Molecular characterization | 6 | 22 |
| U.S. Field 2016 | Efficacy | 4 | 6 |
| | Agronomics | 12 | |
| Brazil Field | Efficacy | 1 | 5 |
| U.S. Field 2017 | Bioinformatic molecular analysis | 3 | 2 |
| Commercial Selection | Further analysis of molecular characterization, protein expression, efficacy and agronomics from multiple field trials | 1 | MON 95379 |

Example 3

Cre-Excision of the Glyphosate Selection Cassette in Corn Event MON 95379

This Example describes the removal of the glyphosate selection cassette from corn event MON 95379 through in vivo Cre-excision. The glyphosate selection cassette was used to select transformed events. By removal of the selection cassette, a "marker-free" event was created wherein only the insecticidal protein expression cassettes remained in the final event.

Figure 3:
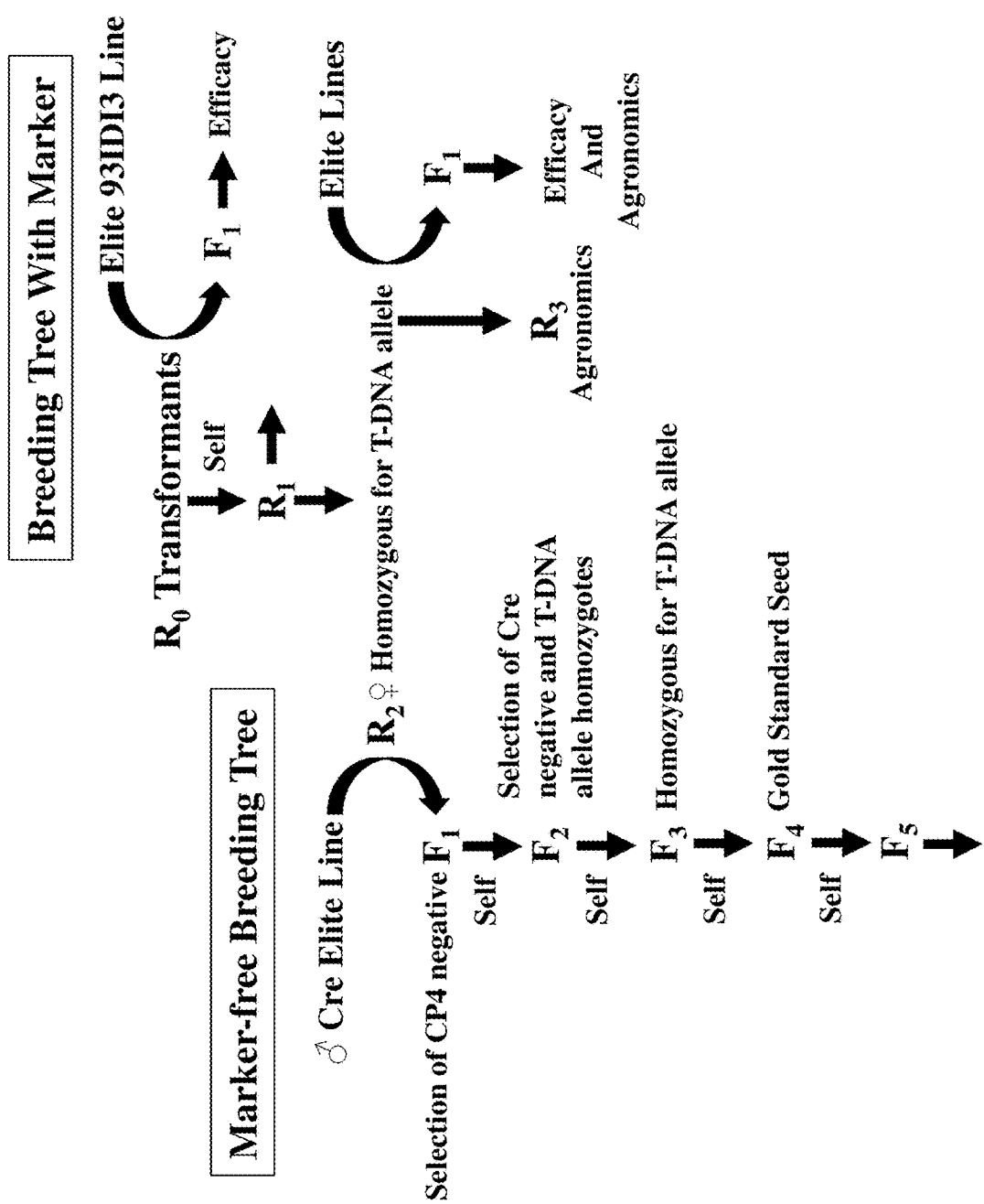
FIG. 3 is a diagrammatic representation of the breeding process to produce the marker-free corn event MON 95379. $R_0$ generation events ("transformants") are those that are derived from the initial transformation with the binary transformation vector used to generate corn event MON 95379. Subsequent "R" generations ($R_1$, and $R_2$) represent successive generations produced through self-pollination of plants derived from the initial $R_0$ transformant that resulted in the corn event MON 95379. The $R_2$ transformants which are homozygous for the T-DNA insertion are cross-pollinated with an elite transgenic corn line comprising a transgene cassette for the expression of Cre-recombinase, resulting in an F1 generation, wherein many of the progeny have lost the CP4 selectable marker cassette due to Cre-recombinase excision. Hemizygous T-DNA positive, CP4 negative plants are selected and self-pollinated, resulting in an $F_2$ generation. $F_2$ plants homozygous for the inserted T-DNA allele without the CP4 marker and lacking the Cre-recombinase transgene cassette are selected and self-pollinated giving rise to an $F_3$ generation. The $F_3$ generation plants are self-pollinated giving rise to a pure line of $F_4$ Gold Standard Seed.

FIG. 3 illustrates the breeding process used to generate the marker-free event MON 95379 corn event. Corn variety LH244 immature embryos were transformed using an *Agrobacterium*-mediated transformation process with Construct MON95 (presented as SEQ ID NO:13, and illustrated in FIG. 2). Construct MON95 comprises three (3) expression cassettes: two (2) expression cassettes for the expression of the insecticidal proteins Cry1B.868 and Cry1Da_7, and a single cassette used for the selection of transformed plant cells using glyphosate selection. The selection cassette was flanked on both sides with LoxP Cre-recombinase recognition sites.

After transformation, the $R_0$ transformants were self-pollinated for two (2) generations, during which time many events were removed based upon various assays such as efficacy, protein expression, seed return and plant health, and molecular characterization. By the $R_2$ generation, thirty-nine (39) events remained from the initial two hundred ten (210) events. The thirty-nine (39) homozygous $R_2$ generation events were bred with an elite line of transformed corn plants expressing Cre-recombinase enzyme, derived from Enterobacteria phage P1.

This stage in which $R_2$ generation events were bred with plants expressing Cre-recombinase is identified as "Cre Cross". Specifically in this stage, de-tasseled (female) $R_2$ generation plants homozygous for SEQ ID NO:13 were cross-pollinated with transgenic corn plants (male) homozygous for a transgene cassette used for expression of Cre-recombinase enzyme. The Cre-recombinase expressing male donor pollen germinates after landing on the silk tissue of the female plant comprising SEQ ID NO:13. Once the pollen tube enters the embryo sac, the pollen tube ruptures, setting free the two sperms of the Cre-recombinase expressing male donor. The nucleus of one sperm fuses with the egg nucleus, forming the zygote. The other sperm nucleus fuses with one of the two polar nuclei which in turn fuses with the other polar nucleus, thereby establishing the primary endosperm nucleus.

Thus, in using the Cre-recombinase expressing plant as the male pollen donor, both the embryo and endosperm of the resulting cross will express Cre-recombinase as the cells divide and develop and become a corn kernel (i.e., seed). The Cre-recombinase binds to inverted repeats in the LoxP site and catalyzes a crossover in an eight-base pair spacer region of the two LoxP sites that flank the expression cassette, resulting in the excision of the marker cassette with one LoxP site remaining in the integrated T-DNA due to recombination (see FIG. 2, "Inserted T-DNA After Cre-Excision").

The $F_1$ progeny resulting from the Cre Cross were selected for the absence of the CP4 selection cassette and allowed to self-pollinate. Through this process, the two alleles—the Cre-recombinase allele and the allele for the T-DNA used to generate event MON 95379—segregate in the resulting $F_2$ population, resulting in progeny homozygous or heterozygous for one or both alleles.

The $F_2$ progeny which demonstrated the absence of the Cre-recombinase allele and homozygosity for SEQ ID NO:9, the transgenic inserted T-DNA after Cre-excision, were selected. These selected $F_2$ progeny were self-pollinated, giving rise to an $F_3$ generation homozygous for SEQ ID NO:9.

A further self-pollination resulted in $F_3$ progeny seed ($F_4$ seed) which were assayed for purity, and were designated as "Gold Standard Seed." $F_4$ was the first generation of gold standard seed.

Excision of the glyphosate selection marker cassette did not affect the expression of Cry1B.868 and Cry1Da_7. Removing the glyphosate selection cassette from corn event MON 95379 through Cre-excision provided a transgenic corn event which is resistant to Lepidopteran pests without adding tolerance to glyphosate in the final event. This "marker-free" event assures flexibility when building corn breeding stacks with other corn transgenic events to provide a multiplicity of products incorporating event MON 95379 and allowing multiple options for providing additional traits in the final breeding stacks.

Example 4

Corn Event MON 95379 Demonstrates Resistance to the Lepidopteran Insect Pests Fall Armyworm, Corn Earworm, Southwestern Corn Borer, Sugarcane Borer This Example describes the activity of the MON 95379 event against Lepidopteran insect pests. The insect toxin proteins Cry1B.868 and Cry1Da_7, when expressed together in corn event MON 95379, provide resistant to Fall Armyworm (*Spodoptera frugiperda*), Corn Earworm (*Helicoverpa zea*), Southwestern Corn Borer (*Diatraea grandiosella*), and Surgarcane Borer (*Diatraea saccharalis*).

After transformation and insertion of Construct MON95, forty-one (41) $R_0$ events were selected for bioassay using leaf discs. Bioassays using plant leaf disks were performed analogous to those described in U.S. Pat. No. 8,344,207. A non-transformed LH244 corn plant was used to obtain tissue to be used as a negative control. Plates comprising wells with one insect per leaf disc in each well were incubated for three (3) days. After three (3) days, the plates were examined. If at least fifty percent (50%) of the leaf disc in the negative controls was consumed, measurements were taken of the transgenic event leaf discs. If less than fifty percent (50%) of the leaf discs in the negative controls had not yet been consumed, the insects were allowed to continue feeding until the fifty percent (50%) target was achieved. Measurements of leaf damage ("leaf damage ratings" or "LDR") and mortality were taken for each well. An average of each measure was determined. The leaf damage ratings ranged from one (1) to eleven (11) and reflect a percentage of the consumed leaf disc. Table 4 shows the leaf damage rating scale used for the $R_0$ leaf disc assays. On this rating scale, the negative controls will always have an LDR of at least 10.

TABLE 4

Leaf Damage Ratings (LDR) scale for $R_0$ leaf disc assays.

| Leaf Damage Rating (LDR) | Amount of feeding damage |
|---|---|
| 1 | ≤5% |
| 2 | ≤10% |
| 3 | ≤15% |
| 4 | ≤20% |
| 5 | ≤25% |
| 6 | ≤30% |
| 7 | ≤35% |
| 8 | ≤40% |
| 9 | ≤45% |
| 10 | ≤50% |
| 11 | >50% |

Table 5 shows the mean leaf damage ratings for the forty-one (41) events transformed with Construct MON95, including the MON 95379 event. As can be seen in Table 5, expression of the two insecticidal proteins, Cry1B.868 and Cry1Da_7, provided resistance to Fall Armyworm (FAW), Corn Earworm (CEW), and Southwestern Corn Borer (SWCB). The LDRs for the negative controls were between 10 and 11. The FAW and SWCB consumed only approximately five percent (5%) of the event MON 95379 leaf disc in comparison to the negative controls which consumed at least fifty percent (50%) of the leaf disc. With respect to CEW, only approximately 6.25% of the leaf discs were consumed in comparison to the negative controls which consumed at least fifty percent (50%) of the leaf disc. In addition, one hundred percent (100%) of the FAW and CEW were killed after consuming the event MON 95379 containing leaf discs.

TABLE 5

Mean Leaf Damage Rating (LDR) scores and Mean Mortality for $R_0$ plants expressing Cry1B.868 and Cry1Da_7.

| Event | FAW Mean LDR | CEW Mean LDR | SWCB Mean LDR |
|---|---|---|---|
| MON 95379 | 1.00 | 1.25 | 1.00 |
| Event 2 | 1.00 | 2.00 | 1.00 |
| Event 3 | 1.00 | 1.00 | 1.00 |
| Event 4 | 1.00 | 1.25 | 1.00 |
| Event 5 | 1.00 | 1.50 | 1.00 |
| Event 6 | 1.00 | 3.25 | 1.00 |
| Event 7 | 1.00 | 2.25 | 1.00 |
| Event 8 | 1.00 | 1.50 | 1.00 |
| Event 9 | 1.00 | 1.75 | 1.00 |
| Event 10 | 1.00 | 2.25 | 1.25 |
| Event 11 | 1.00 | 1.75 | 1.00 |
| Event 12 | 1.00 | 1.25 | 1.00 |
| Event 13 | 1.00 | 1.25 | 1.00 |
| Event 14 | 1.00 | 3.75 | 1.00 |
| Event 15 | 1.00 | 1.00 | 1.00 |
| Event 16 | 1.00 | 1.25 | 1.25 |
| Event 17 | 1.00 | 3.00 | 1.00 |
| Event 18 | 1.00 | 1.25 | 1.00 |
| Event 19 | 1.00 | 1.75 | 1.25 |
| Event 20 | 1.00 | 1.00 | 1.25 |
| Event 21 | 1.00 | 5.00 | 1.00 |
| Event 22 | 1.00 | 1.33 | 1.00 |
| Event 23 | 1.00 | 1.00 | 1.00 |
| Event 24 | 1.00 | 1.50 | 1.00 |
| Event 25 | 1.00 | 1.25 | 1.00 |
| Event 26 | 1.00 | 2.33 | 1.25 |
| Event 27 | 1.00 | 1.25 | 1.00 |
| Event 28 | 1.00 | 1.50 | 1.00 |
| Event 29 | 1.00 | 1.00 | 1.00 |
| Event 30 | 1.00 | 2.00 | 1.00 |
| Event 31 | 1.00 | 2.50 | 1.50 |
| Event 32 | 1.00 | 1.00 | 1.00 |
| Event 33 | 1.00 | 1.67 | 1.00 |
| Event 34 | 1.00 | 3.00 | 1.00 |
| Event 35 | 1.00 | 1.25 | 1.00 |
| Event 36 | 1.00 | 1.50 | 1.00 |
| Event 37 | 1.00 | 2.50 | 1.00 |
| Event 38 | 1.00 | 3.50 | 1.25 |
| Event 39 | 1.00 | 1.00 | 1.25 |
| Event 40 | 1.00 | 1.00 | 1.00 |
| Event 41 | 1.00 | 1.25 | 1.00 |

The forty-one (41) events were crossed with non-transgenic 93IDI3 variety plants. $F_1$ heterozygous progeny plants were selected that comprised Construct MON95. Around five (5) $F_1$ plants for each event were artificially infested in a greenhouse for each insect pest species. With respect to FAW, approximately forty (40) neonates were used to infest each $F_1$ plant in the V6 to V8 stage whorl. With respect to SWCB, approximately thirty (30) neonates were used to infest the $F_1$ plant in the V6 to V10 stage whorl. Measures of leaf damage for FAW and SWCB were taken approximately fourteen (14) days after infestation. Tables 6 and 7 show the damage rating scales used to assess the leaf damage.

TABLE 6

Leaf damage rating scale for corn plants infested with FAW.

| Leaf Damage Rating (LDR) | Description |
|---|---|
| 0 | No visible damage |
| 1 | Only pinhole lesions present on whorl leaves |
| 2 | Pinholes and small, circular lesions present on whorl leaves |
| 3 | Small, circular lesions and 1-3 small, elongated lesions present on whorl and furl leaves |
| 4 | 4-6 small to mid-sized, elongated lesions present on 1-3 whorl and furl leaves |
| 5 | 4-6 large, elongated lesions present on 1-3 whorl and furl leaves and/or 1-3 small or mid-sized, uniform to irregular lesions, or both eaten from whorl and/or furl leaves |
| 6 | 4-6 large, elongated lesions present on 4-6 whorl and furl leaves and/or 4-6 large uniform to irregular shaped holes eaten from whorl and furl leaves |
| 7 | 7+ elongated lesions of all sizes present on several whorl and furl leaves plus 4-6 large uniform to irregular shaped holes eaten from the whorl and furl leaves |
| 8 | 7+ elongated lesions of all sizes on most whorl and furl leaves plus 7+ mid- to large-sized uniform to irregular-shaped holes eaten from the whorl and furl leaves |
| 9 | Whorl and furl leaves almost totally destroyed as well as the plant showing signs of stunting |

TABLE 7

Leaf damage rating scale for corn plants infested with SWCB.

| Leaf Damage Rating (LDR) | Description |
|---|---|
| 0 | No lesions |
| 1 | Small amount of pin or fine holes on leaves |

TABLE 7-continued

Leaf damage rating scale for corn plants infested with SWCB.

| Leaf Damage Rating (LDR) | Description |
|---|---|
| 2 | Small amount of shot-hole injury on a few present |
| 3 | Shot-hole injury common on several leaves |
| 4 | Several leaves with shot-hole and elongated lesions |
| 5 | Several leaves with elongated lesions |
| 6 | Several leaves with elongated lesions-2.5 cm. Long |
| 7 | Long lesions common on ~50% of leaves |
| 8 | Long lesions common on ~70% of leaves |
| 9 | Most or all leaves with long lesions |

The SWCB infested $F_1$ plants were also assessed for the length of stalk boring caused by SWCB. To determine the length of stalk boring, corn stalks of the corn plants were broken at approximately eye level and the top portion was used to inspect for boring damage. The stalks were split using a double handled knife and the length of the tunnel bored out by SWCB was measured in centimeters (cm). In these experiments, the tunnel length was capped at ten centimeters (10 cm).

In addition, five (5) $F_1$ plants for each event were also infested with CEW to measure the amount of damage caused by CEW to the corn ear. Approximately forty (40) CEW nymphs were used to infest each plant and were placed on the green silks of $R_1$ stage plants. Twenty-one (21) days after infestation, the developing ears were examined, and the damage was recorded as $cm^2$ ear damage.

Table 8 shows the mean leaf damage ratings for the $F_1$ events infested with FAW and SWCB, the stalk boring lengths caused by SWCB, and the ear damage caused by CEW, wherein "NT" indicates not tested.

TABLE 8

Mean leaf damage ratings of $F_1$ transgenic corn plants infested with FAW and SWCB, stalk boring lengths caused by SWCB, and ear damage caused by CEW.

| Event | FAW LDR | SWCB LDR | SWCB tunnel length (cm) | CEW ear damage (cm² damage) |
|---|---|---|---|---|
| MON 95379 | 0.30 | 1.00 | 0.00 | 3.25 |
| Event 2 | 0.50 | 1.00 | 0.00 | 3.25 |
| Event 3 | 0.30 | 1.00 | 0.00 | 0.00 |
| Event 4 | 0.30 | 1.30 | 0.00 | 2.30 |
| Event 5 | 1.00 | 1.00 | 0.00 | 1.00 |
| Event 6 | 0.30 | 1.00 | 0.00 | 0.00 |
| Event 7 | 0.80 | 0.50 | 0.00 | 3.00 |
| Event 8 | 0.50 | 1.00 | 0.00 | 0.00 |
| Event 9 | 1.30 | 0.80 | 0.00 | 0.25 |
| Event 10 | NT | NT | NT | NT |
| Event 11 | NT | NT | NT | NT |
| Event 12 | 0.30 | 1.00 | 0.00 | 3.50 |
| Event 13 | NT | NT | NT | NT |
| Event 14 | NT | NT | NT | NT |
| Event 15 | NT | NT | NT | NT |
| Event 16 | NT | NT | NT | NT |
| Event 17 | 0.50 | NT | NT | NT |
| Event 18 | 0.00 | 1.30 | 0.00 | 2.50 |
| Event 19 | 0.80 | 1.30 | 0.00 | 0.00 |
| Event 20 | NT | NT | NT | NT |
| Event 21 | NT | NT | NT | NT |
| Event 22 | NT | NT | NT | NT |
| Event 23 | NT | NT | NT | NT |
| Event 24 | 0.50 | 0.50 | 2.50 | 2.75 |
| Event 25 | 0.00 | 1.50 | 2.25 | 0.00 |
| Event 26 | 0.30 | 1.30 | 0.00 | 3.00 |
| Event 27 | 0.50 | 1.50 | 2.50 | 1.25 |
| Event 28 | 0.30 | 1.00 | 1.00 | 1.75 |
| Event 29 | 0.30 | 1.00 | 1.00 | 0.25 |
| Event 30 | NT | NT | NT | NT |
| Event 31 | 0.30 | 1.00 | 0.00 | 2.50 |
| Event 32 | 0.50 | 1.00 | 0.00 | 0.25 |
| Event 33 | 0.50 | 1.00 | 0.00 | 2.25 |
| Event 34 | 0.30 | 1.00 | 0.00 | 1.50 |
| Event 35 | 0.30 | 1.30 | 1.25 | 0.00 |
| Event 36 | NT | NT | NT | NT |
| Event 37 | 0.50 | 1.00 | 0.00 | 1.50 |
| Event 38 | 1.30 | 1.00 | 0.00 | 0.50 |
| Event 39 | 0.00 | 1.00 | 1.75 | 2.00 |
| Event 40 | 0.30 | 0.50 | 1.25 | 1.75 |
| Event 41 | 0.00 | 0.80 | 0.00 | 2.25 |
| Negative Control | 7.80 | 9.00 | 10.00 | 13.25 |

As can be seen in Table 8, leaf damage to corn event MON 95379 was minimal for both FAW and SWCB when compared to the negative controls. Essentially, once the insects started to feed on the event MON 95379 $F_1$ leaf, expression of the Cry1B.868 and Cry1Da_7 insecticidal proteins in the corn leaves containing event MON 95379 caused the insect to cease consuming the leaf. SWCB tunneling was not observed in event MON 95379 while the negative controls showed extensive tunneling. With respect to CEW ear damage, the damage to the ear was much less compared to the negative control, and was comparable to the ear damage observed in several commercially-available transgenic corn events. Infestation of the magnitude used in the $F_1$ assays was much higher than what is usually seen in nature. The $F_1$ assays demonstrated that corn event MON 95379 provides superior control of FAW, SWCB, and CEW.

In the summer of 2016, the $F_1$ progeny from the remaining thirty-nine (39) events after $R_2/F_1$ described in Example 2/Table 3 were assayed for resistance to FAW, CEW, and SWCB in field experiments using artificial infestation. Multiple locations were used to assay resistance.

FAW resistance was assayed in three (3) locations: Jerseyville, Ill.; Thomasboro, Ill.; and Union City, Tenn. In each location, each event was assayed in three (3) field plots using one (1) row per plot and thirty (30) seeds per row. Forty (40) FAW neonates were used to infest each plant twice, at the early and mid-whorl stage (V4 and V7 vegetative stage). Leaf feeding damage ratings were assessed using the scale as provided in Table 6.

SWCB resistance was assayed in three (3) locations: one (1) in Jonesboro, Ark. and two (2) in Union City, Tenn. In each location, each event was assayed in three (3) field plots using one (1) row per plot and thirty (30) seeds per row. Thirty (30) SWCB neonates were used to infest each plant at the mid-whorl stage (V7-V8). At the time of fifty percent (50%) pollen shed, the plants were infested again with thirty (30) SWCB neonates per plant. Stalk tunneling damage was assessed as previously described.

CEW resistance was assayed in five (5) locations: Jerseyville, Ill., Jonesboro, Ark., Monmouth, Ill., Thomasboro, Ill., and Union City, Tenn. In each location, each event was assayed in three (3) field plots using one (1) row per plot and thirty (30) seeds per row. Plants were infested when the silks were fresh and green, and some ear formation had started (R1 through R3 stage). CEW egg strips were used for infestation. Each strip contained approximately forty (40) eggs. One (1) strip was placed between the ear and stalk of each plant, with the eggs facing ear and close to the silks. Evaluation of ear damage was determined twenty-one (21) to twenty-eight (28) days after infestations. By this time, the insect has progressed from larval to pupal stage. Damage to the ears was measured as previously described.

For FAW and SWCB, data from all three (3) locations was used. For CEW, due to various field conditions, only data from Jonesboro, Ark. could be used. Table 9 shows the mean FAW leaf damage ratings, the SWCB tunnel lengths, and the CEW ear damage measurements for each of the tested events and the negative control.

TABLE 9

Mean FAW leaf damage ratings, SWCB tunnel length, and CEW ear damage for 2016 field efficacy trials.

| Event | FAW LDR | SWCB Tunnel Length (cm) | CEW Ear Damage (cm2) |
|---|---|---|---|
| MON 95379 | 1.56 | 0.37 | 2.86 |
| Event 2 | 1.28 | 1.84 | 4.41 |
| Event 3 | 1.33 | 0.14 | 3.28 |
| Event 4 | 2.01 | 0.11 | 3.00 |
| Event 5 | 1.83 | 0.89 | 4.09 |
| Event 6 | 1.46 | 1.09 | 2.89 |
| Event 7 | 1.67 | 0.39 | 3.40 |
| Event 8 | 1.44 | 0.72 | 3.19 |
| Event 9 | 1.59 | 0.00 | 3.98 |
| Event 10 | 2.85 | 0.35 | 2.96 |
| Event 11 | 1.50 | 2.59 | 2.84 |
| Event 12 | 1.39 | 0.42 | 3.04 |
| Event 13 | 1.74 | 0.00 | 3.34 |
| Event 14 | 2.52 | 1.22 | 3.01 |
| Event 15 | 1.53 | 0.22 | 3.09 |
| Event 16 | 1.50 | 1.61 | 3.24 |
| Event 17 | 2.31 | 1.72 | 2.80 |
| Event 18 | 1.70 | 0.13 | 4.02 |
| Event 19 | 1.28 | 1.00 | 3.96 |
| Event 20 | 1.28 | 0.52 | 2.79 |
| Event 21 | 1.39 | 0.39 | 3.55 |
| Event 22 | 1.72 | 0.94 | 4.34 |
| Event 23 | 1.86 | 0.22 | 3.04 |
| Event 24 | 1.93 | 0.00 | 3.60 |
| Event 25 | 1.57 | 0.06 | 2.28 |
| Event 26 | 1.65 | 0.00 | 2.28 |
| Event 27 | 1.65 | 0.28 | 2.73 |
| Event 28 | 1.63 | 2.72 | 3.60 |
| Event 29 | 2.62 | 0.78 | 3.42 |
| Event 30 | 4.78 | 12.59 | 5.25 |
| Event 31 | 1.78 | 1.81 | 3.79 |
| Event 32 | 1.63 | 0.00 | 3.08 |
| Event 33 | 1.37 | 0.00 | 3.40 |
| Event 34 | 1.80 | 0.19 | 3.20 |
| Event 35 | 2.20 | 0.84 | 3.99 |
| Event 36 | 1.96 | 0.22 | 3.78 |
| Event 37 | 1.35 | 0.06 | 3.07 |
| Event 38 | 1.22 | 0.27 | 3.94 |
| Event 39 | 1.46 | 0.14 | 2.87 |
| Negative Control | 7.15 | 7.21 | 32.25 |

As demonstrated in Table 9, corn event MON 95379 provided excellent control of FAW, SWCB, and CEW when compared to the negative control. The level of infestation in these assays was much higher than what would normally be encountered in the field under natural conditions, demonstrating the superior performance of event MON 95379 under high insect pressure.

During concurrent field trials and Cre-excision of the selection cassette and the production of Gold Standard Seed, further characterization of the events was performed. As a result of extensive molecular characterization, efficacy, expression, and agronomic studies, events were dropped from testing, leaving two (2) events: Event 1 and MON 95379. Event 1 was de-prioritized based on observed yield drag in agronomic studies, leaving event MON 95379 for advancement.

During the 2016 to 2017 growing season in Argentina, event MON 95379 was assayed for resistance to FAW, CEW, and SCB in temperate and subtropical regions under natural infestation conditions. FAW leaf damage ratings were determined for event MON 95379 grown in the subtropical region of Argentina using the scale provided in Table 6. SCB tunneling data was obtained for event MON 95379 from two (2) locations in the temperate region of Argentina. CEW ear damage data was obtained for event MON 95379 from two (2) locations in the temperate region and three (3) locations in the subtropical regions of Argentina. Table 11 shows the mean FAW leaf damage ratings, SCB tunnel length, and CEW ear damage under natural infestation conditions for event MON 95379 and a negative control during the 2016-2017 Argentina growing seasons.

TABLE 10

Mean FAW leaf damage ratings, SCB tunnel length, and CEW ear damage for 2016-2017 Argentina field efficacy trials.

| Event | FAW (LDR) | SCB Tunnel Length (cm) | CEW Ear Damage (cm2) |
|---|---|---|---|
| MON 95379 | 1.27 | 0.00 | 1.32 |
| Negative Control | 7.48 | 4.43 | 5.83 |

As can be seen in Table 10, event MON 95379 provided resistance to FAW, SCB, and CEW when compared to the negative control under natural infestation conditions in Argentina.

Event MON 95379 was also evaluated for resistance against FAW resistant to a commercially-available corn event (MON89034, which expresses Cry1a.105 and Cry2Ab2) over three (3) growing seasons in Puerto Rico (January 2016, July 2016, and January 2017). Table 11 shows the mean leaf damage ratings based upon the scale presented in Table 6 for each of the three (3) growing seasons compared with event MON89034 and the negative control.

TABLE 11

Mean leaf damage ratings for event MON 95379 and event MON89034 naturally-infested with event MON89034-resistant FAW.

| Event | January 2016 | July 2016 | January 2017 |
|---|---|---|---|
| MON 95379 | 2.30 | 2.22 | 1.40 |
| MON89034 | 5.68 | 4.54 | 7.36 |
| Negative Control | 8.73 | 6.84 | 9.00 |

As can be seen in Table 11, corn event MON 95379 demonstrated resistance to event MON89034-resistant FAW under high natural pressure relative to the negative control.

In the summer of 2017, event MON 95379 was evaluated for resistance against FAW, SWCB, and CEW in the United States using methods similar to that described for the summer of 2016. FAW resistance was assayed at three (3)

locations: Jerseyville, Ill.; Thomasboro, Ill.; and Monmouth, Ill. In each location, each event was assayed in three (3) field plots using one (1) row per plot and thirty (30) seeds per row. Forty (40) FAW neonates were used to infest each plant two times. The first infestation occurred around V5 stage. The second infestation for plants in Monmouth, Ill. and Jerseyville, Ill. occurred around V8 stage. Due to a low hatch rate and poor weather, a second infestation was not possible in Thomasboro, Ill. FAW leaf feeding damage ratings were assessed using the scale as provided in Table 6.

SWCB resistance was assayed at three (3) locations, one (1) in Jonesboro, Ark. and two (2) in Union City, Ill. In each location, each event was assayed in three (3) field plots using one (1) row per plot and thirty (30) seeds per row. Thirty (30) SWCB neonates were used to infest each plant two times. Under normal conditions, the first infest is performed at the mid-whorl stage (V7-V8) in half of the row, but infestation was delayed about a week. Regardless, strong insect pressure was established. At the time of fifty percent (50%) pollen shed the second half of the row of plants were infested with thirty (30) SWCB neonates per plant. Stalk tunneling damage was assessed as previously described.

CEW resistance was assayed at six (6) locations: Jerseyville, Ill., Jonesboro, Ark., Paragould, Ark., Monmouth, Ill., and two locations in Union City, Tenn. In each location, each event was assayed in three (3) field plots using one (1) row per plot and thirty (30) seeds per row. Due to a shortage of insects, infestations in Monmouth, Ill. and Jerseyville, Ill. were infested two (2) to three (3) weeks later than when silks are fresh and green. In Monmouth, approximately twenty-two (22) neonates were used to infest each plant. In Jerseyville, Ill., twenty-three (23) to twenty-four (24) neonates were used to infest partially opened corn ears. In Jonesboro, Ark., one (1) of the three (3) rows received approximately thirty (30) neonates per plant, and the other two (2) rows received sixteen (16) to eighteen (18) neonates per plant. In Paragould, Ark., all three (3) rows received approximately thirty (30) neonates per plant. Infestation was delayed in the two locations of Union City, Tenn. due to insect availability. Both locations received eighteen (18) neonates per plant. Evaluation of ear damage was determined twenty-one (21) to twenty-eight (28) days after infestations. Damage to the ears was expressed as previously described. Artificial infestations were conducted on both marker and marker-free event MON 95379 plants. In addition, assays were also conducted using the natural insect pressure at the locations for the marker-containing event MON 95379 plants. Tables 12 and 13 show the FAW leaf damage ratings, SWCB tunnel lengths, and the CEW ear damage for marker-containing and marker-free event MON 95379 plants.

TABLE 12

Mean FAW leaf damage ratings, SWCB tunnel length, and CEW ear damage for event MON 95379 plants before Cre-excision of the selection marker under conditions of artificial and natural infestation.

| | Before Cre-excision of CP4 Marker | | | | |
| --- | --- | --- | --- | --- | --- |
| Event | FAW Artificial Infestation (LDR) | FAW Natural Infestation (LDR) | CEW Artificial Infestation (cm2) | CEW Natural Infestation (cm2) | SWCB Artificial Infestation Tunnel Length (cm) |
| MON 95379 | 1.17 | 1.15 | 4.93 | 5.81 | 0.00 |
| Negative Control | 7.08 | 8.15 | 8.49 | 14.57 | 14.34 |

TABLE 13

Mean FAW leaf damage ratings, SWCB tunnel length, and CEW ear damage for marker-free event MON 95379 plants under artificial infestation.

| | After Cre-excision of CP4 Marker | | |
| --- | --- | --- | --- |
| Event | FAW Artificial Infestation (EDR) | CEW Artificial Infestation (cm2) | SWCB Artificial Infestation Tunnel Length (cm) |
| MON 95379 | 1.20 | 5.39 | 0.27 |
| Negative Control | 7.08 | 8.49 | 14.34 |

As can be seen in Tables 12 and 13, event MON 95379 provided resistance against FAW, SWCB, and CEW under artificial (marker and marker-free) and natural (marker-free) infestation conditions.

In 2018, a hybrid cross of event MON 95379 with event MON89034 was assayed for resistance to FAW in a Brazil field trial under natural infestation conditions. The field trial was conducted in Santa Helena de Goiás, State of Goiás. In this location there are FAW populations resistant to the transgenic corn event MON89034. Transgenic corn plants corresponding to the cross of events MON 95379×MON89034, event MON89034, and a conventional corn plant (negative control) were planted. At V6 stage, leaf damage rating scores were determined for sixty (60) plants corresponding to the cross of events MON 95379×MON89034, thirty (30) plants corresponding to event MON89034, and thirty (30) negative controls using the scale presented in Table 6. In addition, the number of FAW neonates, larvae greater than two millimeters (2 mm) and less than or equal to 1.5 centimeters, and larvae greater than 1.5 centimeters were recorded for each plant. Table 14 shows the mean leaf damage ratings for the cross of events MON 95379×MON89034, event MON89034, and the negative control, along with the numbers of neonates and larvae observed on the corn plants.

TABLE 14

Mean FAW leaf damage rating and number of neonates and larvae from Brazil, 2018 field trials for the cross of events MON 95379 × MON89034, event MON89034 and negative control.

| Event | FAW (LDR) | Neonates | Larvae >2 mm and ≤1.5 cm | Larvae >1.5 cm |
| --- | --- | --- | --- | --- |
| MON 95379 × MON89034 | 0.62 | 0 | 0 | 0 |
| MON 89034 | 1.47 | 6 | 16 | 0 |
| Negative Control | 5.20 | 0 | 22 | 9 |

As can be seen in Table 14, the cross of events MON 95379×MON89034 provided resistance to FAW under natural infestation conditions relative to the negative control. The cross of events MON 95379×MON89034 also performed better than event MON89034 under conditions where event MON89034-resistant FAW are within the population of FAW. With respect to neonates and larvae, none were observed on the plants corresponding to the cross of events MON 95379×MON89034. Neonates and larvae between two (2) millimeters and one and a half (1.5)

centimeters were observed on event MON89034 plants. The negative control plants were observed to have even more larvae than event MON89034 plants, and had larvae that had grown greater than 1.5 centimeters.

Example 5

Assay of Activity of Corn Event MON 95379 Against Lesser Cornstalk Borer

This Example describes the assay of activity of transgenic corn event MON 95379 against the Lepidopteran insect pest, Lesser Cornstalk Borer (LSCB, *Elasmopalpus lignosellus*).

Event MON 95379 was grown in a greenhouse along with negative control plants and infested with LSCB neonates. Ten (10) event MON 95379 plants and nine (9) negative control plants were grown in individual pots. Nine (9) days after planting, each plant was infested with ten (10) LSCB neonates per plant. Twenty-two (22) days after infestation, the plants were examined and rated for damage using a 0-4 damage rating scale as presented in Table 15.

TABLE 15

LSCB plant damage rating scale.

| LSCB Damage Rating | Severity of Injury | Description |
| --- | --- | --- |
| 0 | No damage | Plants without injury |
| 1 | Slight injury | Plants with scratches in leaves and/or stalk |
| 2 | Average damage | Plants with stalk parts damaged |
| 3 | Serious damage | Plants with stalk parts damage and dead hear symptoms |
| 4 | Dead plant | Dead plants |

The resulting LSCB damage ratings for each plant is presented in Table 16.

TABLE 16

LSCB plant damage for each infested plant.

| Plant | MON 95379 | Negative Control |
| --- | --- | --- |
| 1 | 0 | 4 |
| 2 | 0 | 2 |
| 3 | 0 | 3 |
| 4 | 0 | 3 |
| 5 | 0 | 4 |
| 6 | 0 | 3 |
| 7 | 0 | 3 |
| 8 | 0 | 4 |
| 9 | 0 | 4 |
| 10 | 0 | |

As can be seen in Table 16, LSCB produced extensive damage to the negative control plants, four (4) of which were rated as "Dead," four (4) of which were rated as "Serious damage," and only one (1) rated as "Average damage." In contrast, the event MON 95379 LSCB infested plants showed no damage.

Transgenic corn event MON 95379 provides resistance to Lesser Cornstalk Borer (LSCB, *Elasmopalpus lignosellus*).

Example 6

Corn Event MON 95379 Provides Consistent Yield and Similar Agronomics to Untransformed LH244 Corn Plants This Example demonstrates that transgenic corn event MON 95379 provides consistent yields and similar agronomics in the field to untransformed LH244 corn plants.

Field trials were conducted with plants corresponding to event MON 95379 prior to Cre-excision of the glyphosate selection cassette to determine various aspects of yield and agronomics in comparison to control plants. Measurements of yield were calculated and expressed as bushels per acre (bu/acre). Plant height and ear height were measured in inches (in). Fifty percent (50%) pollen shed and fifty percent (50%) silking were expressed as days after planting (DAP). Test weight, which is a measurement of bulk density, or the weight of a unit volume, of grain was expressed in pounds per bushel (lb/bu). The USDA established the standard test weight of a bushel of corn as fifty-six pounds per bushel (56 lb/bu) based upon a 15.5% moisture content. The percent moisture of the corn kernel was expressed on a wet weight basis. The moisture content is the amount of water in the seed and is usually expressed as a percentage. It can be expressed on either a wet weight basis (where it is expressed as a percentage of the fresh weight of the seed) or on a dry weight basis (where it is expressed as a percentage of the dry weight of the seed). Determination of percent moisture is destructive to the seed. Percent moisture (wet basis) can be calculated with the simple formula:

$$M_{wb} = (W_w / W_w + W_d) \times 100$$

Where $W_w$ is equal to the weight of the water and $W_d$ is equal to the weight of the dry matter.

In the growing season of 2016 in the United States, yield and agronomic measures were determined for event MON 95379 inbreds and hybrids pre-Cre-excision of the glyphosate maker cassette. Tables 17 and 18 show the yield and agronomic characteristics measured for event MON 95379 inbreds and hybrids, respectively. The negative control plants for the inbred comparisons was untransformed variety LH244. Hybrids containing event MON 95379 were created by cross pollinating the inbred event MON 95379 with corn variety 93IDI3, and the untransformed control was an LH244×93IDI3 cross.

TABLE 17

Yield and agronomics for event MON 95379 inbreds relative to non-transgenic controls.

| | Yield (bu/acre) | | Plant Height (in) | | Ear Height (in) | | 50% Pollen Shed (DAP) | | 50% Silking (DAP) | |
| --- | --- | --- | --- | --- | --- | --- | --- | --- | --- | --- |
| Event | Mean | SE | Mean | SE | Mean | SE | Mean | SE | Mean | SE |
| MON 95379 | 111.08 | 5.17 | 85.40 | 2.72 | 41.29 | 1.45 | 65.11 | 2.00 | 65.77 | 2.05 |
| LH244 | 114.18 | 5.02 | 82.05 | 2.32 | 38.73 | 1.33 | 62.60 | 1.79 | 63.54 | 1.82 |

TABLE 18

Yield and agronomic for event MON 95379 hybrids relative to non-transgenic controls.

| Event | Yield (bu/acre) | | Test Weight (lb/bu) | | Percent Moisture | |
|---|---|---|---|---|---|---|
| | Mean | SE | Mean | SE | Mean | SE |
| MON 95379 × 93IDI3 | 203.48 | 7.04 | 58.78 | 0.61 | 16.04 | 0.42 |
| LH244 × 93IDI3 | 196.45 | 6.81 | 58.31 | 0.61 | 15.89 | 0.43 |

As can be seen in Tables 17 and 18, the yield and other agronomic measures for event MON 95379 in the 2016 United States field trials were relatively the same for both inbreds and hybrids relative to the controls. The variability between the inbreds and hybrids and their respective controls was within acceptable limits and demonstrate there were no negative impacts on yield and other agronomic characteristics caused by insertion of the T-DNA into the corn genome of event MON 95379.

Yield and agronomics were also studied in Argentina during the 2016 to 2017 growing season for event MON 95379 inbreds and hybrids pre-Cre-excision of the glyphosate marker cassette. Tables 19 and 20 show the yield and agronomic characteristics measured for event MON 95379 inbreds. The negative control plants for the inbred comparisons was untransformed variety LH244. Hybrids containing event MON 95379 were created by cross-pollinating events MON89034×MON895379. The transgenic control was event MON88017×event MON89034. The non-transgenic control was a LH244×93IDI3 cross. Table 21 shows the yield and agronomic characteristics measured for event MON 95379 hybrids, wherein "NC" indicates not calculated.

TABLE 19

Yield and agronomics for event MON 95379 inbreds relative to non-transgenic controls.

| Event | Yield (bu/acre) | | Plant Height (in) | | Ear Height (in) | | 50% Pollen Shed (DAP) | | 50% Silking (DAP) | |
|---|---|---|---|---|---|---|---|---|---|---|
| | Mean | SE | Mean | SE | Mean | SE | Mean | SE | Mean | SE |
| MON 95379 | 113.39 | 4.57 | 73.89 | 1.05 | 38.38 | 0.95 | 64.32 | 0.60 | 64.68 | 0.62 |
| LH244 | 105.49 | NC | 71.69 | NC | 36.66 | NC | 64.86 | NC | 65.17 | NC |

TABLE 20

Yield and agronomics for event MON 95379 inbreds relative to non-transgenic controls.

| Event | Test Weight (lb/bu) | | Percent Moisture | |
|---|---|---|---|---|
| | Mean | SE | Mean | SE |
| MON 95379 | 59.28 | 0.10 | 16.54 | 0.26 |
| LH244 | 59.32 | NC | 16.01 | NC |

TABLE 21

Yield and agronomics for event MON 95379 hybrids relative to transgenic and non-transgenic controls.

| Event | Yield (bu/acre) | | Test Weight (lb/bu) | | Percent Moisture | |
|---|---|---|---|---|---|---|
| | Mean | SE | Mean | SE | Mean | SE |
| MON89034 × MON 95379 | 165.80 | 5.94 | 60.06 | 0.20 | 15.12 | 0.18 |
| MON88017 × MON89034 | 164.87 | 5.94 | 59.62 | 0.20 | 15.45 | 0.18 |
| LH244 × 93IDI3 | 166.82 | NC | 59.70 | NC | 15.38 | NC |

As can be seen in Tables 19 through 21, the measures of yield and other agronomic characteristics were relatively the same for event MON 95379 inbreds and hybrids relative to the controls.

In 2017, yield and agronomics were again measured in field trials in the United States for event MON 95379 inbreds and hybrids pre-Cre-excision of the glyphosate marker cassette. Inbred and hybrid controls were similar to those used in the 2016 United States field trials. Table 22 shows the yield and agronomic characteristics for event MON 95379 inbreds relative to non-transgenic controls, and Tables 23 and 24 show the yield and agronomic characteristics measured for event MON 95379 hybrids relative to non-transgenic controls in the 2017 United States field trials.

TABLE 22

Yield and agronomics for event MON 95379 inbreds relative to non-transgenic controls.

| Event | Yield (bu/acre) | | Test Weight (lb/bu) | | Percent Moisture | |
|---|---|---|---|---|---|---|
| | Mean | SE | Mean | SE | Mean | SE |
| MON 95379 | 116.49 | 5.45 | 57.86 | 0.59 | 21.16 | 0.76 |
| LH244 | 124.46 | 5.39 | 58.60 | 0.58 | 20.57 | 0.76 |

TABLE 23

Yield and agronomic for event MON 95379 hybrids relative to non-transgenic controls.

| Event | Yield (bu/acre) Mean | SE | Plant Height (in) Mean | SE | Ear Height (in) Mean | SE | 50% Pollen Shed (DAP) Mean | SE | 50% Silking (DAP) Mean | SE |
|---|---|---|---|---|---|---|---|---|---|---|
| MON 95379 × 93IDI3 | 213.15 | 4.84 | 99.14 | 2.50 | 45.27 | 1.77 | 56.65 | 0.93 | 57.17 | 1.06 |
| LH244 × 93IDI3 | 217.86 | 4.44 | 97.42 | 2.28 | 45.61 | 1.45 | 55.87 | 0.91 | 56.47 | 1.04 |

TABLE 24

Yield and agronomic for event MON 95379 hybrids relative to non-transgenic controls.

| Event | Test Weight (lb/bu) Mean | SE | Percent Moisture Mean | SE |
|---|---|---|---|---|
| MON 95379 × 93IDI3 | 57.98 | 0.37 | 19.73 | 0.51 |
| LH244 × 93IDI3 | 57.53 | 0.36 | 19.74 | 0.50 |

As can be seen in Tables 22 through 24, the yield and other agronomic properties event MON 95379 demonstrated in the 2017 United Stated field trials were similar to the untransformed controls for both inbred and hybrid lines.

During the 2018 to 2019 growing season in Argentina, agronomics and yield were measured in field trials for event MON 95379 inbreds and hybrids post-Cre-excision of the glyphosate marker cassette. Inbred controls were similar to those used in the 2017 United States field trials. The hybrids were produced through crosses with the elite variety 80IDM2. Tables 25 and 26 show the yield and agronomic characteristics for event MON 95379 inbreds relative to non-transgenic controls, and Table 27 shows the yield and agronomic characteristics measured for event MON 95379 hybrids relative to non-transgenic controls in the 2018 to 2019 Argentina field trials.

TABLE 25

Yield and agronomics for event MON 95379 inbreds relative to non-transgenic controls.

| Event | Yield (bu/acre) Mean | SE | Plant Height (in) Mean | SE | Ear Height (in) Mean | SE | 50% Pollen Shed (DAP) Mean | SE | 50% Silking (DAP) Mean | SE |
|---|---|---|---|---|---|---|---|---|---|---|
| MON 95379 | 92.81 | 7.30 | 85.14 | 2.45 | 40.57 | 2.06 | 62.74 | 0.61 | 63.77 | 0.65 |
| LH244 | 103.46 | 7.68 | 83.93 | 1.72 | 38.57 | 1.24 | 62.93 | 0.61 | 63.88 | 0.71 |

TABLE 26

Yield and agronomics for event MON 95379 inbreds relative to non-transgenic controls.

| Event | Test Weight (lb/bu) Mean | SE | Percent Moisture Mean | SE |
|---|---|---|---|---|
| MON 95379 | 59.59 | 1.52 | 17.49 | 0.96 |
| LH244 | 60.34 | 0.97 | 17.24 | 0.69 |

TABLE 27

Yield and agronomics for event MON 95379 hybrids relative to non-transgenic controls.

| Event | Yield (bu/acre) Mean | SE | Test Weight (lb/bu) Mean | SE | Percent Moisture Mean | SE |
|---|---|---|---|---|---|---|
| MON 95379 × 80IDM2 | 206.86 | 8.37 | 59.42 | 0.46 | 19.03 | 0.84 |
| LH244 × 80IDM2 | 207.81 | 8.11 | 59.22 | 0.45 | 19.12 | 0.83 |

As can be seen in Tables 25 through 27, the yield and other agronomic properties event MON 95379 demonstrated in the 2017 to 2018 Argentina field trials were similar to the untransformed controls for both inbred and hybrid lines.

Thus, in sum, corn event MON 95379 demonstrated similar yield and other agronomic properties over four (4) separate growing seasons in the United States and Argentina. Event MON 95379 does not negatively affect yield or cause a change in other agronomic properties measured compared to non-transgenic and transgenic controls.

Example 7

Corn Event MON 95379 Event-Specific Endpoint TAQMAN® Assays

The following Example describes methods useful in identifying the presence of event MON 95379 in a corn sample. A pair of PCR primers and a probe were designed for the purpose of identifying the unique junction formed between the corn genomic DNA and the inserted DNA of event MON 95379 in an event-specific endpoint TAQMAN® PCR. Examples of conditions utilized for identifying the presence of event MON 95379 in a corn sample in an event-specific endpoint TAQMAN® PCR are described in Table 28 and Table 29.

The sequence of the oligonucleotide forward primer SQ21529 (SEQ ID NO:15) is identical to the nucleotide sequence corresponding to positions 833-852 of SEQ ID NO:10. The sequence of the oligonucleotide reverse primer SQ21524 (SEQ ID NO:16) is identical to the reverse complement of the nucleotide sequence corresponding to positions 905-934 of SEQ ID NO:10. The sequence of the oligonucleotide probe PB10269 (SEQ ID NO:17) is identical to the reverse complement of the nucleotide sequence corresponding to positions 886-901 of SEQ ID NO:10. The primers SQ21529 (SEQ ID NO:15) and SQ21524 (SEQ ID NO:16) with probe PB10269 (SEQ ID NO:17), which may be fluorescently labeled (e.g., a 6-FAM™ fluorescent label), can be used in an endpoint TAQMAN® PCR assay to identify the presence of DNA derived from event MON 95379 in a sample.

In addition to SQ21529 (SEQ ID NO:15), SQ21524 (SEQ ID NO:16), and PB10269 (SEQ ID NO:17), it should be apparent to persons skilled in the art that other primers and/or probes can be designed to either amplify or hybridize to sequences within SEQ ID NO:10 which are unique to, and useful for, detecting the presence of DNA derived from event MON 95379 in a sample.

Following standard molecular biology laboratory practices, PCR assays for event identification were developed for detection of event MON 95379 in a sample. Parameters of either a standard PCR assay or a TAQMAN® PCR assay were optimized with each set of primer pairs and probes (e.g., probes labeled with a fluorescent tag such as 6-FAM™) used to detect the presence of DNA derived from event MON 95379 in a sample. A control for the PCR reaction includes internal control primers and an internal control probe (e.g., VIC®-labeled) specific to a region within the corn genome that is used as an internal control, and are primers SQ20222 (SEQ ID NO:18), SQ20221 (SEQ ID NO:19), and VIC® labeled probe PB50237 (SEQ ID NO:20).

Generally, the parameters which were optimized for detection of event MON 95379 in a sample included primer and probe concentration, amount of templated DNA, and PCR amplification cycling parameters. The controls for this analysis include a positive control from corn containing event MON 95379, a negative control from non-transgenic corn, and a negative control that contains no template DNA.

TABLE 28

MON 95379 event-specific endpoint TAQMAN® PCR reaction components.

| Step | Reagent | Stock Concentration (µM) | Volume (µl) | Final Concentration (µM) | Comments |
|---|---|---|---|---|---|
| 1 | Reaction volume 2× Master Mix | | 5 2.28 | | 1× final concentration |
| 2 | Event Specific Primer SQ51219 | 100 | 0.05 | 0.9 | |
| 3 | Event Specific Primer SQ21524 | 100 | 0.05 | 0.9 | |
| 4 | Event Specific 6FAM ™ probe PB10269 | 100 | 0.01 | 0.2 | Probe is light sensitive |
| 5 | Internal Control Primer SQ20222 | 100 | 0.05 | 0.9 | |
| 6 | Internal Control Primer SQ20221 | 100 | 0.05 | 0.9 | |
| 7 | Internal Control VIC ® probe PB50237 | 100 | 0.01 | 0.2 | Probe is light sensitive |
| 8 | Extracted DNA (template): Leaf Samples to be analyzed Negative control (non-transgenic DNA) Negative water control (No template control) Positive Qualitative control(s) MON 95379 DNA | | 2.5 | | Separate reactions are made for each template. |

TABLE 29

Endpoint TAQMAN ® thermocycler conditions.

| Step No. | Number of Cycles | Settings |
|---|---|---|
| 1 | 1 | 95° C. 20 seconds |
| 2 | 40 | 95° C. 3 seconds |
| | | 60° C. 20 seconds |
| 3 | 1 | 10° C. |

Example 8

Assays for Determining Zygosity for Event MON 95379 Using TAQMAN® and Detection of the Insect Toxin Transgenes The following Example describes methods useful in identifying the zygosity of event MON 95379 and detection of the insect toxin transgenes in event MON 95379 in a corn sample. Pairs of PCR primers and a probe are designed for the purpose of identifying specific properties of alleles positive and negative for the T-DNA insertion that gave rise to event MON 95379.

A zygosity assay is useful for determining if a plant comprising an event is homozygous for the event DNA (i.e., comprising the exogenous DNA in the same location on each chromosome of the chromosomal pair), heterozygous for the event DNA (i.e., comprising the exogenous DNA on only one chromosome of the chromosomal pair), or wild-type (i.e., null for the event DNA).

An endpoint TAQMAN® thermal amplification method was used to develop a zygosity assay for event MON 95379. The assay uses a primer pair and a probe to detect amplicons corresponding to one of the two insect toxin coding sequences encoding Cry1B.868 and Cry1Da_7 comprised within the T-DNA used to generate corn event MON 95379. In addition, a primer pair and probe are used to detect a single-copy internal control that is located within the corn genome and is known to be present as a homozygous allele.

For this assay two (2) primer pairs and two (2) probes were mixed together with the sample. The DNA primers used in the zygosity assay which detects the presence of the Cry1B.868 toxin coding sequence were primers SQ50998 (SEQ ID NO:21) and SQ50997 (SEQ ID NO:22). The VIC®-labeled DNA probe used in the zygosity assay which detects the presence of the Cry1B.868 toxin coding sequence was PB54340 (SEQ ID NO:23). The DNA primers used in the zygosity assay which detect the presence of the Cry1Da_7 toxin coding sequence were primers SQ50485 (SEQ ID NO:24) and SQ50484 (SEQ ID NO:25). The VIC®-labeled DNA probe used in the zygosity assay which detects the presence of the Cry1Da_7 toxin coding sequence was PB50138 (SEQ ID NO:26). Both zygosity detection assays use the same internal control. The primers for the internal control were SQ20222 (SEQ ID NO:18) and SQ20221 (SEQ ID NO:19), and the 6FAM™-labeled probe for the internal control was PB50237 (SEQ ID NO:20). The DNA primers and probe for either Cry1B.868 or Cry1Da_7 were mixed with the primers and probe for the internal control as shown in Tables 30 and 31.

TABLE 30

Corn event MON 95379 zygosity TAQMAN ® PCR for the detection of Cry1B.868.

| Step | Reagent | Stock Concentration (µl) | Volume (µl) | Final Concentration (µM) | Comments |
|---|---|---|---|---|---|
| | Reaction volume | | 5 | | |
| 1 | 2× Master Mix | | 2.4 | | 1× final concentration |
| 2 | Cry1B.868 specific primer SQ50998 | 100 | 0.0225 | 0.45 | |
| 3 | Cry1B.868 specific primer SQ50997 | 100 | 0.0225 | 0.45 | |
| 4 | Cry1B.868 6FAM ™ probe PB50340 | 100 | 0.005 | 0.1 | Probe is light sensitive |
| 5 | Internal Control Primer SQ20222 | 100 | 0.0225 | 0.45 | |
| 6 | Internal Control Primer SQ20221 | 100 | 0.0225 | 0.45 | |
| 7 | Internal Control VIC ® probe PB50237 | 100 | 0.005 | 0.1 | Probe is light sensitive |
| 8 | Extracted DNA (template): Leaf Samples to be analyzed Negative control (non-transgenic DNA) Negative water control (No template control) Positive copy number control(s) Cry1B.868 | | 2.5 | | Separate reactions are made for each template. |

TABLE 31

Corn event MON 95379 zygosity TAQMAN ® PCR for the detection of Cry1Da_7.

| Step | Reagent | Stock Concentration (µl) | Volume (µl) | Final Concentration (µM) | Comments |
|---|---|---|---|---|---|
| | Reaction volume | | 5 | | |
| 1 | 2× Master Mix | | 2.4 | | 1× final concentration |
| 2 | Cry1Da_7 specific Primer SQ50485 | 100 | 0.0225 | 0.45 | |
| 3 | Cry1Da_7 specific Primer SQ50484 | 100 | 0.0225 | 0.45 | |
| 4 | Cry1Da_7 specific 6FAM ™ probe PB50138 | 100 | 0.005 | 0.1 | Probe is light sensitive |
| 5 | Internal Control Primer SQ20222 | 100 | 0.0225 | 0.45 | |
| 6 | Internal Control Primer SQ20221 | 100 | 0.0225 | 0.45 | |
| 7 | Internal Control VIC ® probe PB50138 | 100 | 0.005 | 0.1 | Probe is light sensitive |
| 8 | Extracted DNA (template): Leaf Samples to be analyzed Negative control (non-transgenic DNA) Negative water control (No template control) Positive copy number control(s) Cry1Da_7 | | 2.5 | | Separate reactions are made for each template. |

Separate reactions are mixed using DNA derived from a leaf sample for which zygosity is not known, a negative control of DNA derived from an untransformed corn plant, a negative control lacking DNA, and a positive control using DNA derived from a transgenic plant homozygous for Cry1B.868 or Cry1Da_7, depending upon which toxin coding sequence is used for detection. The reactions are then subjected to the thermal cycles presented in Table 32.

TABLE 32

Zygosity TAQMAN ® Thermocycler conditions.

| Step No. | Number of Cycles | Settings |
|---|---|---|
| 1 | 1 | 95° C. 20 seconds |
| 2 | 40 | 95° C. 3 seconds |
| | | 60° C. 20 seconds |
| 3 | 1 | 10° C. |

After amplification, the cycle thresholds (Ct values) were determined for the amplicon corresponding to the toxin coding sequence and the single-copy, homozygous internal standard. The difference (ΔCt) between the Ct value of the single-copy, homozygous internal standard amplicon and the Ct value of the toxin coding sequence amplicon was determined. With respect to zygosity, a ΔCt of around zero (0) indicated homozygosity of the inserted event MON 95379 T-DNA and ΔCt of around one (1) indicated heterozygosity of the inserted event MON 95379 T-DNA. Lack of an amplicon corresponding to the insect toxin coding sequence indicated the sample is null for the inserted event MON 95379 T-DNA. The Ct values in the TAQMAN® thermal amplification method will have some variability due to multiple factors such as amplification efficiency and ideal annealing temperatures. Therefore, the range of "about one (1)" is defined as a ΔCt of 0.75 to 1.25.

For each progeny derived from a cross with event MON 95379, assays were performed for both toxin coding sequences to assure accuracy in the determination of zygosity of the progeny.

Example 9

Assays for Determining Zygosity for Corn Event MON 95379 Using TAQMAN®

The following Example describes a method useful in identifying the zygosity of event MON 95379 in a corn sample.

Pairs of PCR primers and a probe are designed for the purpose of identifying specific properties of alleles positive and negative for the T-DNA insertion that gave rise to event MON 95379. Examples of conditions that may be used in an event-specific zygosity TAQMAN® PCR are provide in Tables 33 and 34. For this assay, three primers and two probes were mixed together with the sample. The DNA primers used in the zygosity assay were primers SQ50219 (SEQ ID NO:15), SQ21524 (SEQ ID NO:16), and PWTDNA (SEQ ID NO:27). The probes used in the zygosity assay were 6FAM™-labeled probe PB10269 (SEQ ID NO:17) and VIC®-labeled probe PRWTDNA (SEQ ID NO:28). Primers SQ50219 (SEQ ID NO:15) and SQ21524 (SEQ ID NO:16) and the 6FAM™-labeled probe PB10269 (SEQ ID NO:17) are diagnostic for event MON 95379 DNA. SQ50219 (SEQ ID NO:15) and PWTDNA (SEQ ID NO:27) and the VIC®-labeled probe PRWTDNA (SEQ ID NO:28) are diagnostic when there is no copy of event MON 95379; i.e., they are diagnostic for the wild type allele.

When the three primers and two probes are mixed together in a PCR reaction with DNA extracted from a plant heterozygous for event MON 95379, there is a fluorescent signal from both the 6FAM™-labeled probe PB10269 (SEQ ID NO:17) and the VIC®-labeled probe PRWTDNA (SEQ ID NO:28) which is indicative of and diagnostic for a plant heterozygous for event MON 95379. When the three primers and two probes are mixed together in a PCR reaction with DNA extracted from a plant homozygous for event MON 95379, there is a fluorescent signal from only the 6FAM™-labeled probe PB10269 (SEQ ID NO:17) and not the VIC®-labeled probe PRWTDNA (SEQ ID NO:28). When the three primers and the two probes are mixed together in a PCR reaction with DNA extracted from a plant which is null for event MON 95379 (i.e., the wild-type), there is a fluorescent signal from only the VIC®-labeled probe PRWTDNA (SEQ ID NO:28). The template DNA samples and controls for this analysis were a positive control from corn containing event MON 95379 DNA (from both a known homozygous and a known heterozygous sample), a negative control from non-transgenic corn and a negative control that contains no template DNA.

TABLE 33

Event MON 95379 zygosity TAQMAN ® PCR

| Step | Reagent | Stock Concentration (μl) | Volume (μl) | Final Concentration (μM) | Comments |
|---|---|---|---|---|---|
| | Reaction volume | | 5 | | |
| 1 | 18 megohm water | | 0.33 | | Adjust for final volume |
| 2 | 2× Master Mix | | 2.5 | | 1× final concentration |
| 3 | Event Specific Primer SQ51219 | 100 | 0.05 | 0.9 | |
| 4 | Event Specific Primer SQ21524 | 100 | 0.05 | 0.9 | |
| 5 | Event Specific 6FAM ™ probe PB10269 | 100 | 0.01 | 0.2 | Probe is light sensitive |
| 6 | WT allele Primer PNEGDNA | 100 | 0.05 | 0.9 | |
| 7 | WT allele VIC ® probe PRBNEGDNA | 100 | 0.01 | 0.2 | Probe is light sensitive |
| 8 | Extracted DNA (template): Leaf Samples to be analyzed Negative control (non-transgenic DNA) Negative water control (No template control) Positive Qualitative control(s) MON 95379 DNA | | 2.5 | | Separate reactions are made for each template. |

TABLE 34

Zygosity TAQMAN ® thermocycler conditions

| Step No. | Number of Cycles | Settings |
|---|---|---|
| 1 | 1 | 95° C. 20 seconds |
| 2 | 40 | 95° C. 3 seconds<br>60° C. 20 seconds |
| 3 | 1 | 10° C. |

Example 10

Identification of Corn Event MON 95379 in any MON 95379 Breeding Event

The following Example describes how one may identify the MON 95379 event within progeny of any breeding activity using corn event MON 95379.

DNA primer pairs are used to produce an amplicon diagnostic for corn event MON 95379. An amplicon diagnostic for event MON 95379 comprises at least one junction sequence. The junction sequences for event MON 95379 are SEQ ID NO:1, SEQ ID NO:2, SEQ ID NO:3, SEQ ID NO:4, SEQ ID NO:5, SEQ ID NO:6, SEQ ID NO:7, and SEQ ID NO:8 ([1], [2], [3], [4], [5], [6], [7], and [8], respectively in FIG. 1). SEQ ID NO:1 is a fifty (50) nucleotide sequence representing the 5' junction region of corn genomic DNA and the integrated transgenic expression cassette. SEQ ID NO:1 is positioned in SEQ ID NO:10 at nucleotide position 838-887. SEQ ID NO:2 is a fifty (50) nucleotide sequence representing the 3' junction region of corn genomic DNA and the integrated transgenic expression cassette. SEQ ID NO:2 is positioned in SEQ ID NO:10 at nucleotide position 14156-14205. SEQ ID NO:3 is a one hundred (100) nucleotide sequence representing the 5' junction region of corn genomic DNA and the integrated transgenic expression cassette. SEQ ID NO:3 is positioned in SEQ ID NO:10 at nucleotide position 813-912. SEQ ID NO:4 is a one hundred (100) nucleotide sequence representing the 3' junction region of corn genomic DNA and the integrated transgenic expression cassette. SEQ ID NO:4 is positioned in SEQ ID NO:10 at nucleotide position 14,131-14,230. SEQ ID NO:5 is a two hundred (200) nucleotide sequence representing the 5' junction region of corn genomic DNA and the integrated transgenic expression cassette. SEQ ID NO:5 is positioned in SEQ ID NO:10 at nucleotide position 763-962. SEQ ID NO:6 is a two hundred (200) nucleotide sequence representing the 3' junction region of corn genomic DNA and the integrated transgenic expression cassette. SEQ ID NO:6 is positioned in SEQ ID NO:10 at nucleotide position 14,081-14,280. SEQ ID NO:7 is a one thousand one hundred sixty (1,160) nucleotide sequence representing the 5' junction region of corn genomic DNA and the integrated transgenic expression cassette. SEQ ID NO:7 is positioned in SEQ ID NO:10 at nucleotide positions 1-1,160. SEQ ID NO:8 is a one thousand one hundred seventy eight (1,178) nucleotide sequence representing the 3' junction region of the integrated transgenic expression cassette and the corn genomic DNA. SEQ ID NO:8 is positioned in SEQ ID NO:10 at nucleotide positions 14,039-15,216.

Primer pairs that will produce an amplicon diagnostic for event MON 95379 include primer pairs based upon the flanking sequences (SEQ ID NO:11 and SEQ ID NO:12) and the inserted T-DNA (SEQ ID NO:9). To acquire a diagnostic amplicon in which SEQ ID NO:1, or SEQ ID NO:3, or SEQ ID NO:5, or SEQ ID NO:7 is found, one would design a forward primer molecule based upon the 5' flanking corn genomic DNA (SEQ ID NO:11; from bases 1 to 862 of SEQ ID NO:10) and a reverse primer molecule based upon the inserted T-DNA (SEQ ID NO:9; from positions 863 through 14,180 of SEQ ID NO:10) in which the primer molecules are of sufficient length of contiguous nucleotides to specifically hybridize to SEQ ID NO:11 and SEQ ID NO:9. To acquire a diagnostic amplicon in which SEQ ID NO:2, or SEQ ID NO:4, or SEQ ID NO:6, or SEQ ID NO:8 is found, one would design a forward primer molecule based upon the inserted T-DNA (SEQ ID NO:9; from positions 863 through 14,180 of SEQ ID NO:10) and a reverse primer molecule based upon the 3' flanking corn genomic DNA (SEQ ID NO:12; from positions 14,181 through 15,216 of SEQ ID NO:10) in which the primer molecules are of sufficient length of contiguous nucleotides to specifically hybridize to SEQ ID NO:9 and SEQ ID NO:12.

For practical purposes, one should design primers which produce amplicons of a limited size range, preferably between 200 to 1000 bases. Smaller sized amplicons in general are more reliably produced in PCR reactions, allow for shorter cycle times, and can be easily separated and visualized on agarose gels or adapted for use in endpoint TAQMAN®-like assays. In addition, amplicons produced using said primer pairs can be cloned into vectors, propagated, isolated and sequenced, or can be sequenced directly with methods well established in the art. Any primer pair derived from the combinations of SEQ ID NO:11 and SEQ ID NO:9 or SEQ ID NO:12 and SEQ ID NO:9 that are useful in a DNA amplification method to produce an amplicon diagnostic for event MON 95379 or progeny thereof is an aspect of the present invention. Any single isolated DNA polynucleotide primer molecule comprising at least eleven (11) contiguous nucleotides of SEQ ID NO:11, SEQ ID NO:9 or SEQ ID NO:12 or their complements that is useful in a DNA amplification method to produce an amplicon diagnostic for event MON 95379 or progeny thereof is an aspect of the present invention.

An example of the amplification conditions for this analysis is illustrated in Tables 28 and 29. Any modification of these methods or the use of DNA primers homologous or complementary to SEQ ID NO:11 or SEQ ID NO:12, or DNA sequences of the genetic elements contained in the transgene insert (SEQ ID NO:9) of event MON 95379, that produce an amplicon diagnostic for event MON 95379 is within the art. A diagnostic amplicon comprises a DNA molecule homologous or complementary to at least one transgene/genomic junction DNA or a substantial portion thereof.

An analysis for an event MON 95379 containing plant tissue sample should include a positive tissue control from a plant that contains event MON 95379, a negative control from a corn plant that does not contain event MON 95379 (e.g., LH244), and a negative control that contains no corn genomic DNA. A primer pair will amplify an endogenous corn DNA molecule and will serve as an internal control for the DNA amplification conditions. Additional primer sequences can be selected from SEQ ID NO: 11, SEQ ID NO: 12, or SEQ ID NO: 9 by those skilled in the art of DNA amplification methods. Conditions selected for the production of an amplicon by the methods shown in Table 28 and Table 29 may differ, but result in an amplicon diagnostic for event MON 95379 DNA. The use of DNA primer sequences within or with modifications to the methods of Table 28 and Table 29 are within the scope of the invention. An amplicon produced by at least one DNA primer sequence derived from SEQ ID NO:11, SEQ ID NO:12, or SEQ ID NO:9 that is diagnostic for event MON 95379 is an aspect of the invention.

DNA detection kits that contain at least one DNA primer of sufficient length of contiguous nucleotides derived from SEQ ID NO:11, SEQ ID NO:12, or SEQ ID NO:9 that, when used in a DNA amplification method, produces a diagnostic amplicon for event MON 95379 or its progeny is an aspect of the invention. A corn plant or seed, wherein its genome will produce an amplicon diagnostic for event MON 95379, when tested in a DNA amplification method is an aspect of the invention. The assay for the event MON 95379 amplicon can be performed by using an Applied Biosystems GeneAmp™ PCR System 9700, Stratagene Robocycler®, Eppendorf® Mastercycler® Gradient thermocycler or any other amplification system that can be used to produce an amplicon diagnostic of event MON 95379 as shown in Table 29.

All publications and published patent documents cited in this specification, and which are material to the invention, are incorporated herein by reference to the same extent as if each individual publication or patent application was specifically and individually indicated to be incorporated by reference.

Having illustrated and described the principles of the present invention, it should be apparent to persons skilled in the art that the invention can be modified in arrangement and detail without departing from such principles. We claim all modifications that are within the spirit and scope of the appended claims.

SEQUENCE LISTING

```
<160> NUMBER OF SEQ ID NOS: 28

<210> SEQ ID NO 1
<211> LENGTH: 50
<212> TYPE: DNA
<213> ORGANISM: Artificial
<220> FEATURE:
<223> OTHER INFORMATION: 50 nucleotide sequence representing the 5'
      junction region of corn genomic DNA and the integrated transgenic
      expression cassette.

<400> SEQUENCE: 1
aagcaaatgt gtggtagtgg tccaattttt tttcaattca aaaatgtaga                50

<210> SEQ ID NO 2
<211> LENGTH: 50
<212> TYPE: DNA
<213> ORGANISM: Artificial
<220> FEATURE:
<223> OTHER INFORMATION: 50 nucleotide sequence representing the 3'
      junction region of the integrated transgenic expression cassette
      and the corn genomic DNA.

<400> SEQUENCE: 2
gctattatgg gtattatggg taggcacatg gaatatagt gggaggcaga                 50

<210> SEQ ID NO 3
<211> LENGTH: 100
<212> TYPE: DNA
<213> ORGANISM: Artificial
<220> FEATURE:
<223> OTHER INFORMATION: 100 nucleotide sequence representing the 5'
      junction region of corn genomic DNA and the integrated transgenic
      expression cassette.

<400> SEQUENCE: 3
cgtacgttcg aggtacctgt cctgcaagca aatgtgtggt agtggtccaa ttttttttca     60
attcaaaaat gtagatgtcc gcagcgttat tataaaatga                           100

<210> SEQ ID NO 4
<211> LENGTH: 100
<212> TYPE: DNA
<213> ORGANISM: Artificial
<220> FEATURE:
<223> OTHER INFORMATION: 100 nucleotide sequence representing the 3'
      junction region of the integrated transgenic expression cassette
      and the corn genomic DNA.

<400> SEQUENCE: 4
cgccaagaag aacgattggc aaacagctat tatgggtatt atgggtaggc acatgggaat     60
atagtgggag gcagaggcgt gcctgtgcct gctcttaatt                           100

<210> SEQ ID NO 5
<211> LENGTH: 200
<212> TYPE: DNA
<213> ORGANISM: Artificial
<220> FEATURE:
<223> OTHER INFORMATION: 200 nucleotide sequence representing the 5'
      junction region of corn genomic DNA and the integrated transgenic
      expression cassette.

<400> SEQUENCE: 5
tcgctagcta tagcttggta gtagtcacca acaacgacct agggagctag cgtacgttcg     60
aggtacctgt cctgcaagca aatgtgtggt agtggtccaa ttttttttca attcaaaaat    120
```

```
gtagatgtcc gcagcgttat tataaaatga aagtacattt tgataaaacg acaaattacg    180
atccgtcgta tttataggcg                                                200
```

<210> SEQ ID NO 6
<211> LENGTH: 200
<212> TYPE: DNA
<213> ORGANISM: Artificial
<220> FEATURE:
<223> OTHER INFORMATION: 200 nucleotide sequence representing the 3'
      junction region of the integrated transgenic expression cassette
      and the corn genomic DNA.

<400> SEQUENCE: 6

```
aggcgcgggt accgtcggtc cgggcctagt aggccaagca ggacgtggcg cgccaagaag     60
aacgattggc aaacagctat tatgggtatt atgggtaggc acatgggaat atagtgggag    120
gcagaggcgt gcctgtgcct gctcttaatt tgagctcctc ccctggccct gatagggcat    180
gtgcatgcgc acaataatca                                                200
```

<210> SEQ ID NO 7
<211> LENGTH: 1160
<212> TYPE: DNA
<213> ORGANISM: Artificial
<220> FEATURE:
<223> OTHER INFORMATION: 1160 nucleotide sequence representing the 5'
      junction region of corn genomic DNA and the integrated transgenic
      expression cassette.

<400> SEQUENCE: 7

```
cgcagcgcag gtccgtgtgg cctgtttgtt ttggcttctg gtagcttctg gccaccaaaa     60
gctgctgcgg actgccaaac gctcagcttt tcagccagct tctataaaat ttgttggggg    120
gcaaaaacca tccaaaatca acataaacac ataatcagtt gagtcgttgt aatagtagga    180
attcgtcact ttctagatcc tgagccctat gaacaatttt atcttcctcc acacgtaatc    240
gtaatgatat tcagattctc cccacagcca gattctcctc acagccagat tttcagaaaa    300
gctggtcaga aaaagctga accaaacagg ccctaggaca cataggaa tggatcaaaa      360 aacatagcgc cgtacccgta cgtacgtgca gtcacagtca gctgctagct agctagctgc    420
gccggcggcg gcgttgtcgg tcttgactca acgacgtccg cggctggcgc cgtcggccag    480
cggcttgttg ccgccggtcc catccggcgg agtccggctg ccagtggccg gcggcggctt    540
cttcttcgtc gtcgtcctgc cctttgccat ccccgctgcc acctggacga gggttctggc    600
tcccgtcgac gtcgacgaga gacgtggcgc gcatttggc tgccgccgta tcgtcgtcgt    660
cgtcgagatt gaaatcgaga gggagcgcgc gggatggctg ccgccggtgg cgcgacatgg    720
tctcgcccgg ccggcgcctg atcgacttct cttccgccgc cttcgctagc tatagcttgg    780
tagtagtcac caacaacgac ctagggagct agcgtacgtt cgaggtacct gtcctgcaag    840
caaatgtgtg gtagtggtcc aatttttttt caattcaaaa atgtagatgt ccgcagcgtt    900
attataaaat gaaagtacat tttgataaaa cgacaaatta cgatccgtcg tatttatagg    960
cgaaagcaat aaacaaatta ttctaattcg gaaatcttta tttcgacgtg tctacattca   1020
cgtccaaatg ggggcttaga tgagaaactt cacgatcgat gcggccacca cgagtcgaca   1080
taacttcgta tagcatacat tatacgaagt tatagcggcc gcaaatcaac ctcactctat   1140
ttaaatgagg tggtaggatt                                               1160
```

<210> SEQ ID NO 8
<211> LENGTH: 1178
<212> TYPE: DNA
<213> ORGANISM: Artificial
<220> FEATURE:
<223> OTHER INFORMATION: 1178 nucleotide sequence representing the 3'
      junction region of the integrated transgenic expression cassette
      and the corn genomic DNA.

<400> SEQUENCE: 8

```
taagggtccc aagtaaggcc ggccaagtaa cggtccgaag taaggcgcgg gtaccgtcgg      60
tccgggccta gtaggccaag caggacgtgg cgcgccaaga agaacgattg gcaaacagct     120
attatgggta ttatgggtag gcacatggga atatagtggg aggcagaggc gtgcctgtgc     180
ctgctcttaa tttgagctcc tccctggcc ctgatagggc atgtgcatgc gcacaataat      240
cattggagct gcctgaatga tttgcatgcg ctcgtgtaaa acgttcacgg tccatgccag     300
tccaagaccg tcggcaagag atgagggcca tgcgcagtac gtacatttgt atacatatac     360
atatttttt ggatgatgcg atgcgtgtgc atatctggct gcgccgctcc ctcgtccatc      420
gtcgtcgcgg tgtacaacga attttccgtg ggatgggctg aacttataat gggcctactg     480
ggcgggccgt atgaaatagc acacaattca ccctgctttt ctcaccagga atgcattttc     540
gcggagcca tcgtcctaac ttggcagaca gacacacaaa cacaggacag gagttcgcca      600
accccagcat gagagaaacc tatccggaca gctcctccag cctatgggcc gttgggcctt     660
cagcctcagc gccccggccc cgtgggcggg caaaacactc cacagtccac acggctgctg     720
ctgctgccct tgttccgtcg gacctggggt aactttatag ctatgatgtt cgcccttccc     780
aaccaatgtg cgagcgttaa ggatgttaag taacactagt taggattatg tggccaaata     840
cctactttgc taggaacttg tacacccctc ataatataga gaaagaaag atgccagtgg      900
tccaactcta taccatgtgt ctcgtgtgtt tgttatgtcg tgcttatgtg aagggagacg     960
agtcttctac agcttctcac gcctaatctg ttgacgggag agaagagagc ggatctggtg    1020
atccgtggta acgtagttct caacaaatga cacattgagc acaccgttgt catctcctca    1080
gctaaacatt gaggggggatt ttttttaag aaaggctgag attcccttac gctcccttg     1140
gcagggctcg tccaacagct tcttgaaaaa ttctataa                            1178
```

<210> SEQ ID NO 9
<211> LENGTH: 13318
<212> TYPE: DNA
<213> ORGANISM: Artificial
<220> FEATURE:
<223> OTHER INFORMATION: Sequence corresponding to the transgenic
      inserted T-DNA of corn event MON 95379.

<400> SEQUENCE: 9

```
ttttttttca attcaaaaat gtagatgtcc gcagcgttat tataaaatga aagtacattt      60
tgataaaacg acaaattacg atccgtcgta tttataggcg aaagcaataa acaaattatt     120
ctaattcgga aatctttatt tcgacgtgtc tacattcacg tccaaatggg ggcttagatg     180
agaaacttca cgatcgatgc ggccaccacg agtcgacata acttcgtata gcatacatta     240
tacgaagtta tagcggccgc aaatcaacct cactctattt aaatgaggtg gtaggatttg     300
ccgcgtgaga cctattaccc tgttatccct agtttaaaca cctgcaggaa aagattaatt     360
aacatcgatc atcatgttca attgacagca aattaaacta gttatatata gggttcatga     420
gatgagagta gctaattatt aacacaagtg gaagaaactt ttatttgacg gtatacaaat     480
```

```
aacaagatac agagatcagg ctgatggatc aatcatatca tatcagtgat agatcgatcg    540
ttcgacacat atatatgtat gacaaaacat agtataagta cgtgcgaaag ggtttatata    600
tatatggata ttgatgcatg gtgtaatggt atggtaatta agggatcgga ggatcgatta    660
atgggtccct atcactcctc catcagtagc agctcgaccg agtccacgat gaaagtgccc    720
tccgtctcgc cgatctcgat ccagactttg tcggtctccg ggaagtactc cagctccttg    780
gtgacgtacc cggcgggcag cggagtgtag tcaccgtagc cacggttgga ctcgcaaggg    840
ttgtccctcc gtccgtcggt gtacgccttc tcctcgtaag cggacgcata atccgcaggc    900
acgctgctgt tggactcgta cgcgccatca tagccgcgat tccgggaagt gtaagtgccc    960
tcgtactcct cttgcgtggc agtgtagtcg ttgcaagtaa cggtgttgtt cgggtacacc   1020
tcctcctcca cacagttcga gaacttgagc tcgtcggtgt tgttctcgat ctcgtggata   1080
gtcacgcagc cttcaccgta gccttccttg tacgcagtca cacggaggat gtagccgcga   1140
ccagggcaga cgcggacctc ctggctcacc tctgcctccc actccggcac gaccagcacg   1200
gaccggtggt tgttctgctc ctcgacgtcc acatggccct tgacgttcca gcaactcagc   1260
ccgttgttga agtcaccgtt cttaataaca ttcctggcat cgtacaggct gaatgctgtg   1320
aagatgcggc cctccagttc ctcgaagatc gccgcgttca caccagggat cactgacagc   1380
tcgggcaggt acgcctcacg gatgctgtgg acccgcttgt cagccgcgtg gatcatggcg   1440
atgttggtgt cagcctggag gcggtcgtac tggctgttga cgaagagtgc gtccactgac   1500
tccttggcct ccttgtacac gatgttggtc tcccactcca gcttctcccg cttgtctcgc   1560
catttcttct cggcgcgctt cacacgagcg agggcctcgc ccacgagagg cttctcctca   1620
aggaactcca ggttgccgag gcgggcatgt ccgtcctggg tcttaatctt gaagataacc   1680
cagacaccca ggtcctcgtt gaggtcggtg cagcccacgt cgatgtccag agagaagtgg   1740
tgcgagtggt gagcgcactt tccgattgga gagggagcgc tcaatggcca aagtgagccc   1800
gtgcctggca cgttcactgt ctcgtgcttg gcgttgtatc ggatcaggta gatttccagg   1860
tcctgactat cctcgatgta cccgcgaagc tggtagcggg tgtacgcctt caatttactc   1920
tcgtctatct tctggtagag atacgtcggg tagcattcgt cgaaagtccc gagcagcgtc   1980
acatagttct ccttgaacac atcgtcgcct ccctggatgg tgatgtctgt actcccgcgc   2040
caaccacggt cgagctggcg gttgatgcca cggaagttcg ggtcctggag caaattccgc   2100
tcgtcactca gacgcttcgc gtgtttgacc ttctcggaca gctccttctt ctcgtcgagg   2160
cagaactcgt cggacaggca ctccacaagg ttggacactt ggtcaatgtg atagtccgtg   2220
acgtcggtct tgagcccaat ctggttgctg ctggtgaaca gttcgttgac agccttctga   2280
gcccgctcca ggtcagactc ggcctcgaac gtcgcatccg ccaggatgat ctcaatcttg   2340
tcgatgtaca gttcgccaga gctgatggag ccagcaccga acagcggttg ctcggagatc   2400
ccaatgatgt cagggttcgc tctgaatgag aaagggttcg agaaatcagt gtaccggaag   2460
gttcggctag tcaagttctc gcctatctcc atcgtcttct ggagaggcat gttgactgag   2520
acttggcctc ccacgcctgt ggacgcggct ccggtcagga caatgaccct cgcgtcgcgg   2580
cttgaagcgt agcggaacct cagacggtaa cgctgggtga tcggcgagtt gatgttcact   2640
tgcaacgaaa cgaagtcgcc gaaagtgttg cgccgcagta tgtctccacc ggtgaagccc   2700
ggaccggtga tgacgctcgt gccacccac acacggaagc ccttcacgag cgggatctgg   2760
ttaatggagt cggaagagat cgtgttggtc cggtcggcgc tgcggtgtgt ccaggagtac   2820
```

```
accggcgcac gcagcgtgtt gccagagatg agccggatgt tggacaggcg gtggctgtag    2880
gactcgtagt tcgggcgttc cgtggtctcg ggcggcagct cagtttcact gtcgaagagc    2940
tgggtgccga cgcccgtgta cccgatggtg tagagcaatg acccgcgcag ggagttcaac    3000
gggttacgcc agttgaaccg ggcccacggg acgccgttga cgggcgttgt cagaaggatg    3060
ttaatgcccg cgaacgactc agtccggtaa acgtcgcggc tcgtgaactg tagcgtaact    3120
gggttgatgg aggtgttggt gttgccgtgg gtactggtgc tcaagctgcc acggatcgtc    3180
ctactctcca atcggtgccc gacccagtag ttcatgtact gtgtgttgga ccagcgtgag    3240
agcacggaga agatcgtgag ctgctcggga aagtcgagca ggtgaggagg gcggatgacg    3300
gcggcctcga ttgccgagaa ggagggtgcg ttgttgttga accaattcgt ggatgcgaaa    3360
ccggagggtg cgttcgtccg gccgattggg tctgtgtaga tctcccgcgt gagttgcgcg    3420
ctagtgttca ttgggtacac ccgtgtgtcg taagacggga atagcgccac caggtctagg    3480
acacccaaag tcaagtcgcg gcggaactgg ttgtaacgga gccatgactc agcgttggtg    3540
ccgcgcaggt tgttgagccc tgtgttgtac catcgagcgc agtagtcact gtactcacgg    3600
gtcttctcca cttggcgctc gtagtaacgc tggatttctt gagatgtgag tccgaactcg    3660
gagccgaaca ggctggcgtc ccgcagcagg agcagatgta agttggcggc ctgggcgtac    3720
accataagga gtggaacttc ctggttcctg atggcgaaca gcggcatagc gttcaggaag    3780
tcgagttcga gagcgatgta ctgggtgtag agtaccgagc gtgttcgcgc gtcatccctg    3840
ttctccaacc agtcctccag tgactgctgg tatgcccgaa aggagtttcc caggccctgt    3900
agcctggcca gagcagtatc gcgggtgttc tccgtgactt gctgccggat caactgctcc    3960
acatgctcca ggaagatctc ccacgggtca cgaccgcgag gccacagctc gcccacaagg    4020
aacgagtaga aggacgcgat ctgaccggcg aatgggacac cgaggacgcc gaggatacgg    4080
cccgcgatgt tgatgccggt ctgaaccgtg ctggccgaca cgaatgggtc gatgttgttg    4140
ccctcggcta tgcagaggga gtcctcgatg cgcgcgtcgg tggacaggtt catctgcgcg    4200
gagtggtttg aaacagcagg gatcgagagg gcgttgatga tctcgttctc gttcttccgg    4260
ttgctcgtca tggtggtggc cggccaagta acggtccgac ctgcagaagt atcaccaaac    4320
aacagggtga gcatcggaca aaagaaacag taccaagcaa ataaatagcg tatgaaggca    4380
gggctaaaaa atccacatat agctgctgca tatgccatca tccaagtata tcaagatcaa    4440
aataattata aaacatactt gtttattata atagataggt actcaaggtt agagcatatg    4500
aatagatgcc gcatatgcca tcatgtatat gcatcagtaa acccacatc aacatgtata    4560 cctatcctag atcaatattt ccatccatca tcttaaactc gtaactatga agatgtatgg    4620
cacacacata aagatacaaa attaataaat ccaccaggta gtttgaaaca gtattctact    4680
ccgatctaga acgaccgccc aaccagacca catcatcaca accaagcgaa aaaaagcatc    4740
tctgtatatg catcagtaaa acccgcatca acatgtatac ctatcctaga tcgatatttc    4800
catccatcat cttaaactcg taactatgaa gatgtaggca catacataca gatcctttaa    4860
taaatccacc aggtagtttg aaacagtatt ctactccgat ctagaacgac cctttatcct    4920
ttaataaatc caccaggtag tttgaaacag tattctactc cgatctagaa cgaccgccca    4980
accagaccat atcatcacaa ccaagcgaga aaaaagcat ctctgtatat gcatcagtaa    5040
aacccgcatc aacatgtata cctatcctag atcgatattt ccatccatca tcttaaactc    5100
gtaactatga agatgtatgg cacacacata cagatacaaa attaataaat ccaccaggta    5160
gcttgaaaca gtatcctact ccgatctaga acgaccgccc aaccagacca catcatcaca    5220
```

| | |
|---|---|
| aacatgaaca tgaacatgtt tgctctaaca caaacatgaa cagaagtaga actaccgggc | 5280 |
| cctaaccatg gaccggatcg ccgatctaga gaaggtagag agagggggggg ggggaggatg | 5340 |
| agcggcgtac cttgaagcgg aggtgccgac ggctggattt gggggagatc tggttgcgtg | 5400 |
| tgtgtgcgct ccgaacgaac acgaggttgg ggaaagaggg tgtggagggg gtgtctattt | 5460 |
| attacggcgg gcgaggaagg gaaagcgaag gagcggtggg aaaggaatcc cccgtagctg | 5520 |
| ccggtgccgt gagaggagga agaggccgcc tgccgtgccg cctcacgtct gccgctccgc | 5580 |
| cacgcaattt ctggatgccg acagcggagc aagtccaacg gtggagcgga actctcgaga | 5640 |
| ggggtccaga ggcagctaca gagatgccgt gccgtctgct tcgcttggcc cgacgcgacg | 5700 |
| ctgctggttc gctggttggt gtccgttaga ctcgtcgacg gcgttgaaca gcctgtcatt | 5760 |
| atctactcga acaagaaaaa atgtttgctt agtttttta tttcttaaag ggtatttgtt | 5820 |
| ttatttgtag tcaatttatt ttatttcatt ttatatctaa attattaaat aaaaaactaa | 5880 |
| aatagagttt tagttttaaa aaatttagag actaaaaaga ataaaatgga tgtactaaaa | 5940 |
| attagtctat agaaaccatc aaccctaaat cctaaatgga tgtactaata aaatggatga | 6000 |
| agtattatat aggtcaagct atttgcaaaa aaaacagaga gatcacatgc acactaaaaa | 6060 |
| gataaaactg tagattgtca aaatattcaa ttatcctta gaccatgtct agcagtttat | 6120 |
| ttatatgatc ctctaaaaca ctaatattat tttagtatta tagactatat tatttgtaga | 6180 |
| gtgaagttta aatatatgta tagagataga taaactacac ttcaaataag tgtgacaaaa | 6240 |
| aaatatgtgg taatttttta tactttagac atgcaatgct ctttatctct agagaggggc | 6300 |
| acgacgcatg caagcttgtt aacgcggccg ctaattctca gtccaaagcc tcaacaaggt | 6360 |
| cagggtacag agtctccaaa ccattagcca aaagctacag gagatcaatg aagaatcttc | 6420 |
| aatcaaagta aactactgtt ccagcacatg catcatggtc agtaagtttc agaaaaagac | 6480 |
| atccaccgaa gacttaaagt tagtgggcat cttttgaaagt aatcttgtca acatcgagca | 6540 |
| gctggcttgt ggggaccaga caaaaaagga atggtgcaga attgttaggc gcacctacca | 6600 |
| aaagcatctt tgcctttatt gcaaagataa agcagattcc tctagtacaa gtggggaaca | 6660 |
| aaataacgtg gaaaagagct gtcctgacag cccactcact aatgcgtatg acgaacgcag | 6720 |
| tgacgaccac aaaagaatta gcttgagctc aggatttagc agcattccag attgggttca | 6780 |
| atcaacaagg tacgagccat atcactttat tcaaattggt atcgccaaaa ccaagaagga | 6840 |
| actcccatcc tcaaaggttt gtaaggaagg tcgaggccgc tgtactgtca tattgtcgtg | 6900 |
| gttttttcaat tgctgtacct gatgcaaacg taatgggttt actaatcttg cacccgccgg | 6960 |
| cttcaaaatg aagagtgcta atttggtcca cgtcaccatc accggttcga actgtctaga | 7020 |
| atggcaggca aagatgattg gacaggcatg cagggaaaaa gagcaccgtt gacgatgtat | 7080 |
| gcgagttccc accattgcga gcaatgatta tcagccacac gacttactct tcagagctaa | 7140 |
| ccactgccat gcagagaaaa agtgaatcat attgtcatga tctacaacga agtgaaacaa | 7200 |
| tcaggcatgc taaagtgctg aaactttact gatctctcat gttggacaac aaagaatacg | 7260 |
| ggaatacatc agcaacgcaa ctcttgagct ttgcttgccg aatgaccagc tagaatttcc | 7320 |
| aagcatttac agaaacatga ctttaagttt cagaaaaaca aatacaaggc cactaaataa | 7380 |
| gcgtggggat aacatatcct ccagatgaca ggcaatctgc aacttgcagc cattcaaatg | 7440 |
| tacgattaac aaaatattta agcgccacat gagataaat atcctccaat tagggccttt | 7500 |
| agtattgtca ttagctcata accatggtgc atcctcacat ggacgctgca taagaagttc | 7560 |

```
ataatagcaa cagacatatg aacaaagcat ggtgcgcctg cccggccgga ctagctagta    7620
ctaccaatca tggaataagc tagtacccta aatgaaatta aaatggtttt tagcgattat    7680
ccacgccgtc cagaatactc taatccacaa gttgaggccg cccatgaagc cgcgagaggg    7740
cgacgccatg tgtataaaag gggcctaagc tgagtggact tgctgcatca gattagtaag    7800
caatctcaag cgcagagagc caaagctttc ggtgtagctc gaagagcaaa gcgaaggcaa    7860
ggcgcgcctg taacctacct accaacctcg ccattcctct ccaaactgtt gtgctgctgt    7920
ctagatctcc cacactacac tagttactcc tcgtagatct cggctacctg gctcaagatc    7980
cggggtcaga tccgggtccg gggattttct tgtgcccta tggctgtatt ttggcgtctg    8040
tggctgatga cagcgtgtgt tctcgagtgc ggatgcaatc tgagttatat aggcaaatgg    8100
ccttgtcaac tcgggcagcg gcattgcttt gctcagtgtg tttgaatgtg ctgaaattca    8160
tgtagtaggc tgtaggctgt gcatttcttg atttgcgtct tgcataattc actggtggat    8220
tttctaaacc taacaagttt aaaattagac cattcaacca agacaggag gaataagtga    8280 agctgttgta gtcacagctt atggccgatc caaaatttgt taggaatgtg aatatgtgat    8340
gctacaaaca tatccttgta agctaccatg ctatttatca tgttccatca tggtgattgg    8400
tgagcactca tgaaaatttc agatccaaac ctagtgttac atgtggattt gtgctctgca    8460
atctatcgcc agtaataaaa tggttgagtg atccagctac tacaaaatca cattgcatac    8520
tttttttttt tgtagattat gcatcctggt tttgggtggt gggttcctga tgtcaggaat    8580
ataaatttag cctgctgatt taggtagcac tgccggtgca cactttggtt tttgaatact    8640
tgtagtcttc cagcttcttg tagaactggt acaatgtggg ccatatataa gaagggctgt    8700
caactagcac atgctcacta attagtctaa acatttatgt ttttattcat tcaggtcagg    8760
tgcaatcata gaagtagtta atgacaatac tttagttgtt ctaatattat ttatgtatgg    8820
actcaaatta acatgcaaaa catatgagat tagtggcatg cattctttt cttaatagtg    8880 gaaaatacga gataatgata actgtgaagc tctgttagta ctcttcatta ctctatttga    8940
gtggcagcat atctcatgct agccataaag caagttctag acgtattctg ttgttaatta    9000
cttgtagcta tataacccaa cctagtcatt ccagcttatg tctcttagag atcatgttta    9060
ttagcacctc aagatttcct ctgcacagta tagtaactat cgaaaagat attatttctt    9120 tgttttaat tgacaacctt cacgtgctac ttattttgc agcttggccg gccaccaacc    9180
atggctgaga tcaacaacca gaaccagtgc gtcccgtaca actgcctgag caaccctaag    9240
gagatcatcc tgggtgagga acgcctggag accggcaaca ccgtagccga cattagcctg    9300
ggcctcatca acttcctcta cagcaacttc gtgccggcg gtggcttcat cgtgggcctc    9360
ctggagctta tctggggctt catcggcccg tcccagtggg acatcttcct cgcccagatc    9420
gagcaactga tcagccagcg gatcgaggag ttcgctagga accaggccat ctcccgcctg    9480
gagggactct ccaacctcta caaggtgtac gtgcgcgcgt tcagcgactg ggagaaggac    9540
ccgaccaacc cggccctccg cgaggaaatg cgtatccagt tcaacgatat gaactcggcc    9600
ctcatcaccg ccatcccgct cttccgcgtg cagaactacg aggtggccct cctgtccgtg    9660
tacgttcaag ccgccaacct ccactctcc atcctccgcg acgtgagcgt gttcggcgag    9720
cgctggggct acgacaccgc caccatcaac aaccgctact ccgacctcac ctccctcatc    9780
cacgtttaca ccaaccactg cgtggacacg tacaaccagg gcctccgcgc cctggagggc    9840
cgcttcctct ccgactggat cgtgtacaac cgcttccgcc gccagctcac catctccgtc    9900
ctggacatcg tcgccttctt tcccaactac gacatccgca cctaccctat ccagaccgcc    9960
```

```
acccagctca cccgcgaggt ctacctcgac ctcccgttca tcaacgagaa cctcagcccg    10020
gccgccgtct acccgacctt ctccgccgct gagtccgcca tcattcgcag cccgcacctc    10080
gtggacttcc tcaactcctt caccatctac accgactccc tcgcccgcag cgcctactgg    10140
ggcggtcacc tcgtgaactc cttccgcacc ggcaccacta ccaacctcat ccgcagcccg    10200
ctctacggcc gcgagggcaa caccgagcgc ccggtgacca tcaccgccag cccgagcgtg    10260
cccatcttcc gcaccctcag ctaccccacc ggcctggaca cagcaaccc tgtggcgggc     10320 atcgagggcg tggagttcca gaacaccatc tccaggagca tctaccgcaa gagcggccct    10380
atcgacagct tcagcgagct gcctcctcag gacgccagcg tgagccctgc catcggctac    10440
agccacaggc tgtgccacgc caccttcctg gagcgcatca gcggccctcg catcgcgggc    10500
accgtgttct cgtggaccca ccgcagcgcc tctcctacga acgaggtgtc tcctagtcgc    10560
atcacccaga tcccttgggt caaggcccac accctggcta gtggcgctag tgtcatcaag    10620
ggccctggct tcaccggtgg tgacatcctg accaggaact ctatgggcga gctgggcact    10680
ctgagggtca ctttcactgg ccgcctgcct cagtcttact acatccgctt ccgctacgct    10740
agtgtcgcta accgctctgg tactttccgc tactctcagc ctccgtctta cggtatctct    10800
ttccctaaga ctatggacgc tggtgagcct ctgaccagta ggagcttcgc tcacactact    10860
ctgttcactc ctatcacttt tctctagggct caggaggagt tcgacctgta catccagtct    10920
ggtgtgtaca tcgacaggat cgagttcatc cccgtgaccg ccacgttcga ggccgagtac    10980
gaccttgagc gcgcccagaa ggtggtgaac gccctcttca ctagcactaa ccagctaggc    11040
ctgaagactg acgtgaccga ctaccacatc gaccaagtga gcaacctagt ggcctgcctc    11100
tccgacgagt tctgcctcga cgagaagcgc gagctgtccg agaaggtgaa gcacgccaag    11160
cgcctctccg acgagcgcaa cctgctccag gaccccaact tcaggggcat caacaggcag    11220
cccgaccgcg gctggcgcgg ctccaccgac atcaccatcc agggcggtga cgacgtattc    11280
aaggagaact acgttaccct ccccggcacc ttcgacgagt gttaccccac ctacctctac    11340
cagaagatcg acgagtccaa gctgaaggcc tacacccgct accagctccg cggctacatc    11400
gaggactccc aggacctgga aatctacctc atccgctaca acgccaagca cgagatcgtg    11460
aacgtgcctg gcaccggcag cctctggcct ctcagcgtgg agaaccagat cggcccttgc    11520
ggcgagccta accgctgcgc ccctcacctc gagtggaacc ctgacctcca ctgctcgtgc    11580
agggacggcg agaagtgcgc ccaccatagc caccacttct ctctggacat cgacgtgggc    11640
tgcaccgacc tgaacgagga cctgggcgtg tgggttatct tcaagatcaa gacccaggac    11700
ggtcacgcca ggctgggtaa cctggagttc cttgaggaaa agcctctgct gggtgaggcc    11760
ctggccaggg tcaagagggc tgagaagaaa tggagggata gaggagac cctgcagctg       11820 gagaccacta tcgtctacaa ggaggctaag gagtctgtcg atgctctgtt cgtcaactct    11880
cagtacgata gactgcaagc tgataccaac atcgctatga tccacgctgc ggataagcgg    11940
gtccaccgga tccggaggc ttaccttccg gagctttctg tcatcccggg tgtcaacgct     12000
gcgatcttcg aggaacttga ggaacggatc ttcactgcgt ttagtctttta cgatgcgcgg    12060 aacatcatca gaacgggga cttcaacaat ggtctgctgt gctggaacgt caagggtcat     12120
gtcgaggtcg aggaacaaaa caatcatcgt agtgtccttg tcattcctga gtgggaggcg    12180
gaggtctctc aagaggtccg tgtttgcccg gggcgtgggg acattcttcg tgttactgcg    12240
tacaaggagg ggtacgggga ggggtgcgtt actattcatg agattgagaa caatactgat    12300
```

```
gagcttaagt tcaacaattg tgttgaggag gaggtttacc cgaacaatac tgttacgtgc    12360
atcaactaca cggcaacgca agaggaatac gaggggacgt acacctcgcg taatagaggg    12420
tatgatgagg cgtacggaaa caacccgtcg gttccagcag attatgcctc ggtttatgag    12480
gagaagtcgt acacggatag acgacgcgag aatccatgtg agtcaaatcg aggatacgga    12540
gattacacac cattaccagc aggatacgtt acaaaggagt tggaatactt cccggaaaca    12600
gataaagttt ggattgaaat cggagaaaca gaaggaacat tcatcgtcga ctcagtagaa    12660
ttgttgttga tggaagaatg atagggaccc cggacccgcc aaaaccattg caaagactat    12720
agtttggggt ggagtatact tggttgtgta catgcctgcg tgttccattg tacacacaaa    12780
acctagccac ctcttgactc ttgagtgtat gcttgttatc cgtgtgttga agtttgtaag    12840
aggcaccatc actatagatg atggcttgtg tccctctttc atcaagattg aataatatat    12900
gctactttga gagcgctatc ctgcttgcct gattgtgtta atacttacat ccgtcccaca    12960
ctcccacaat ataaggaaat aaggtatttt ggcagtttag agcaaaattc ccttatattt    13020
ttgggacgga tgtcctcttt tctgcatttt tttatgttca tatgttcctg aagagtaagg    13080
tggatcttga tcaacctgtc ggtttatggt gattgatttg agtggaatag aatgggccaa    13140
cgtccggcat acagttatgc ttcagttaat taaaagtaag ggtcccaagt aaggccggcc    13200
aagtaacggt ccgaagtaag gcgcgggtac cgtcggtccg ggcctagtag gccaagcagg    13260
acgtggcgcg ccaagaagaa cgattggcaa acagctatta tgggtattat gggtaggc     13318
```

<210> SEQ ID NO 10
<211> LENGTH: 15216
<212> TYPE: DNA
<213> ORGANISM: Artificial
<220> FEATURE:
<223> OTHER INFORMATION: Sequence corresponding to the contig nucleotide sequence of the 5' genomic flanking DNA nucleotide sequence, the inserted T-DNA sequence in event MON 95379, and the 3' genomic flanking DNA nucleotide sequence.

<400> SEQUENCE: 10

```
cgcagcgcag gtccgtgtgg cctgtttgtt ttggcttctg gtagcttctg gccaccaaaa      60
gctgctgcgg actgccaaac gctcagcttt tcagccagct tctataaaat ttgttggggg     120
gcaaaaacca tccaaaatca acataaacac ataatcagtt gagtcgttgt aatagtagga    180
attcgtcact ttctagatcc tgagcccctat gaacaatttt atcttcctcc acacgtaatc    240
gtaatgatat tcagattctc cccacagcca gattctcctc acagccagat tttcagaaaa    300
gctggtcaga aaaagctga accaaacagg ccctaggaca cataggaa tggatcaaaa    360 aacatagcgc cgtacccgta cgtacgtgca gtcacagtca gctgctagct agctagctgc    420
gccggcggcg gcgttgtcgg tcttgactca acgacgtccg cggctggcgc cgtcggccag    480
cggcttgttg ccgccggtcc catccggcgg agtccggctg ccagtggccg gcggcggctt    540
cttcttcgtc gtcgtcctgc cctttgccat ccccgctgcc acctggacga gggttctggc    600
tcccgtcgac gtcgacgaga acgtggcgc cgcatttggc tgccgccgta tcgtcgtcgt    660
cgtcgagatt gaaatcgaga gggagcgcgc gggatggctg ccgccggtgg cgcgacatgg    720
tctcgcccgg ccggcgcctg atcgacttct cttccgccgc cttcgctagc tatagcttgg    780
tagtagtcac caacaacgac ctagggagct agcgtacgtt cgaggtacct gtcctgcaag    840
caaatgtgtg gtagtggtcc aattttttt caattcaaaa atgtagatgt ccgcagcgtt    900
attataaaat gaaagtacat tttgataaaa cgacaaatta cgatccgtcg tatttatagg    960
```

```
cgaaagcaat aaacaaatta ttctaattcg gaaatctttta tttcgacgtg tctacattca    1020
cgtccaaatg ggggcttaga tgagaaactt cacgatcgat gcggccacca cgagtcgaca    1080
taacttcgta tagcatacat tatacgaagt tatagcggcc gcaaatcaac ctcactctat    1140
ttaaatgagg tggtaggatt tgccgcgtga gacctattac cctgttatcc ctagtttaaa    1200
cacctgcagg aaaagattaa ttaacatcga tcatcatgtt caattgacag caaattaaac    1260
tagttatata tagggttcat gagatgagag tagctaatta ttaacacaag tggaagaaac    1320
ttttatttga cggtatacaa ataacaagat acagagatca ggctgatgga tcaatcatat    1380
catatcagtg atagatcgat cgttcgacac atatatatgt atgacaaaac atagtataag    1440
tacgtgcgaa agggtttata tatatatgga tattgatgca tggtgtaatg gtatggtaat    1500
taagggatcg gaggatcgat taatgggtcc ctatcactcc tccatcagta gcagctcgac    1560
cgagtccacg atgaaagtgc cctccgtctc gccgatctcg atccagactt tgtcggtctc    1620
cgggaagtac tccagctcct tggtgacgta cccggcgggc agcggagtgt agtcaccgta    1680
gccacggttg gactcgcaag ggttgtccct ccgtccgtcg gtgtacgcct tctcctcgta    1740
agcggacgca taatccgcag gcacgctgct gttggactcg tacgcgccat catagccgcg    1800
attccgggaa gtgtaagtgc cctcgtactc ctcttgcgtg gcagtgtagt cgttgcaagt    1860
aacggtgttg ttcgggtaca cctcctcctc cacacagttc gagaacttga gctcgtcggt    1920
gttgttctcg atctcgtgga tagtcacgca gccttcaccg tagccttcct tgtacgcagt    1980
cacacggagg atgtagccgc gaccagggca gacgcggacc tcctggctca cctctgcctc    2040
ccactccggc acgaccagca cggaccggtg gttgttctgc cctcgacgt ccacatggcc    2100 cttgacgttc cagcaactca gcccgttgtt gaagtcaccg ttcttaataa cattcctggc    2160
atcgtacagg ctgaatgctg tgaagatgcg gccctccagt tcctcgaaga tcgccgcgtt    2220
cacaccaggg atcactgaca gctcgggcag gtacgcctca cggatgctgt ggacccgctt    2280
gtcagccgcg tggatcatgg cgatgttggt gtcagcctgg aggcggtcgt actggctgtt    2340
gacgaagagt gcgtccactg actccttggc ctccttgtac acgatgttgg tctcccactc    2400
cagcttctcc cgcttgtctc gccatttctt ctcggcgcgc ttcacacgag cgagggcctc    2460
gcccacgaga ggcttctcct caaggaactc caggttgccg aggcgggcat gtccgtcctg    2520
ggtcttaatc ttgaagataa cccagacacc caggtcctcg ttgaggtcgg tgcagcccac    2580
gtcgatgtcc agagagaagt ggtgcgagtg gtgagcgcac tttccgattg gagagggagc    2640
gctcaatggc caaagtgagc ccgtgcctgg cacgttcact gtctcgtgct ggcgttgta    2700 tcggatcagg tagatttcca ggtcctgact atcctcgatg tacccgcgaa gctggtagcg    2760
ggtgtacgcc ttcaatttac tctcgtctat cttctggtag agatacgtcg ggtagcattc    2820
gtcgaaagtc ccgagcagcg tcacatagtt ctccttgaac acatcgtcgc ctccctggat    2880
ggtgatgtct gtactcccgc gccaaccacg gtcgagctgg cggttgatgc cacgaaagtt    2940
cgggtcctgg agcaaattcc gctcgtcact cagacgcttc gcgtgtttga ccttctcgga    3000
cagctccttc ttctcgtcga ggcagaactc gtcggacagg cactccacaa ggttggacac    3060
ttggtcaatg tgatagtccg tgacgtcggt cttgagccca atctggttgc tgctggtgaa    3120
cagttcgttg acagccttct gagcccgctc caggtcagac tcggcctcga acgtcgcatc    3180
cgccaggatg atctcaatct tgtcgatgta cagttcgcca gagctgatgg agccagcacc    3240
gaacagcggt tgctcggaga tcccaatgat gtcagggttc gctctgaatg agaaagggtt    3300
cgagaaatca gtgtaccgga aggttcggct agtcaagttc tcgcctatct ccatcgtctt    3360
```

```
ctggagaggc atgttgactg agacttggcc tcccacgcct gtggacgcgg ctccggtcag    3420
gacaatgacc ctcgcgtcgc ggcttgaagc gtagcggaac ctcagacggt aacgctgggt    3480
gatcggcgag ttgatgttca cttgcaacga aacgaagtcg ccgaaagtgt tgcgccgcag    3540
tatgtctcca ccggtgaagc ccggaccggt gatgacgctc gtgccacccc acacacggaa    3600
gcccttcacg agcgggatct ggttaatgga gtcggaagag atcgtgttgg tccggtcggc    3660
gctgcggtgt gtccaggagt acaccggcgc acgcagcgtg ttgccagaga tgagccggat    3720
gttggacagg cggtggctgt aggactcgta gttcgggcgt tccgtggtct cgggcggcag    3780
ctcagtttca ctgtcgaaga gctgggtgcc gacgcccgtg tacccgatgg tgtagagcaa    3840
tgacccgcgc agggagttca acgggttacg ccagttgaac cgggcccacg ggacgccgtt    3900
gacgggcgtt gtcagaagga tgttaatgcc cgcgaacgac tcagtccggt aaacgtcgcg    3960
gctcgtgaac tgtagcgtaa ctgggttgat ggaggtgttg gtgttgccgt gggtactggt    4020
gctcaagctg ccacggatcg tcctactctc aatcggtgc ccgacccagt agttcatgta     4080
ctgtgtgttg gaccagcgtg agagcacgga gaagatcgtg agctgctcgg gaaagtcgag    4140
caggtgagga gggcggatga cggcggcctc gattgccgag aaggagggtg cgttgttgtt    4200
gaaccaattc gtggatgcga aaccggaggg tgcgttcgtc cggccgattg ggtctgtgta    4260
gatctcccgc gtgagttgcg cgctagtgtt cattgggtac acccgtgtgt cgtaagacgg    4320
gaatagcgcc accaggtcta ggacacccaa agtcaagtcg cggcggaact ggttgtaacg    4380
gagccatgac tcagcgttgg tgccgcgcag gttgttgagc cctgtgttgt accatcgagc    4440
gcagtagtca ctgtactcac gggtcttctc cacttggcgc tcgtagtaac gctggatttc    4500
ttgagatgtg agtccgaact cggagccgaa caggctggcg tcccgcagca ggagcagatg    4560
taagttggcg gcctgggcgt acaccataag gagtggaact tcctggttcc tgatggcgaa    4620
cagcggcata gcgttcagga agtcgagttc gagagcgatg tactgggtgt agagtaccga    4680
gcgtgttcgc gcgtcatccc tgttctccaa ccagtcctcc agtgactgct ggtatgcccg    4740
aaaggagttt cccaggccct gtagcctggc cagagcagta tcgcgggtgt tctccgtgac    4800
ttgctgccgg atcaactgct ccacatgctc caggaagatc tcccacgggt cacgaccgcg    4860
aggccacagc tcgcccacaa ggaacgagta gaaggacgcg atctgaccgg cgaatgggac    4920
accgaggacc ccgaggatac ggcccgcgat gttgatgccg gtctgaaccg tgctggccga    4980
cacgaatggg tcgatgttgt tgccctcggc tatgcagagg gagtcctcga tgcgcgcgtc    5040
ggtggacagg ttcatctgcg cggagtggtt tgaaacagca gggatcgaga gggcgttgat    5100
gatctcgttc tcgttcttcc ggttgctcgt catggtggtg gccggccaag taacggtccg    5160
acctgcagaa gtatcaccaa acaacagggt gagcatcgga caaagaaac agtaccaagc     5220 aaataaatag cgtatgaagg cagggctaaa aaatccacat atagctgctg catatgccat    5280
catccaagta tatcaagatc aaaataatta taaaacatac ttgtttatta taatagatag    5340
gtactcaagg ttagagcata tgaatagatg ccgcatatgc catcatgtat atgcatcagt    5400
aaaacccaca tcaacatgta tacctatcct agatcaatat ttccatccat catcttaaac    5460
tcgtaactat gaagatgtat ggcacacaca taaagataca aaattaataa atccaccagg    5520
tagtttgaaa cagtattcta ctccgatcta gaacgaccgc ccaaccagac cacatcatca    5580
caaccaagcg aaaaaaagca tctctgtata tgcatcagta aaacccgcat caacatgtat    5640
acctatccta gatcgatatt tccatccatc atcttaaact cgtaactatg aagatgtagg    5700
```

```
cacatacata cagatcctttt aataaatcca ccaggtagtt tgaaacagta ttctactccg   5760
atctagaacg acccttatc ctttaataaa tccaccaggt agtttgaaac agtattctac   5820
tccgatctag aacgaccgcc caaccagacc atatcatcac aaccaagcga gaaaaaaagc   5880
atctctgtat atgcatcagt aaaacccgca tcaacatgta tacctatcct agatcgatat   5940
ttccatccat catcttaaac tcgtaactat gaagatgtat ggcacacaca tacagataca   6000
aaattaataa atccaccagg tagcttgaaa cagtatccta ctccgatcta aacgaccgc   6060 ccaaccagac cacatcatca caaacatgaa catgaacatg tttgctctaa cacaaacatg   6120
aacagaagta gaactaccgg gccctaacca tggaccggat cgccgatcta gagaaggtag   6180 agagagggg ggggggagga tgagcggcgt accttgaagc ggaggtgccg acggctggat   6240
ttgggggaga tctggttgcg tgtgtgtgcg ctccgaacga acacgaggtt ggggaaagag   6300
ggtgtggagg gggtgtctat ttattacggc gggcgaggaa gggaaagcga aggagcggtg   6360
ggaaaggaat cccccgtagc tgccggtgcc gtgagaggag gaagaggccg cctgccgtgc   6420
cgcctcacgt ctgccgctcc gccacgcaat ttctggatgc cgacagcgga gcaagtccaa   6480
cggtggagcg gaactctcga gaggggtcca gaggcagcta cagagatgcc gtgccgtctg   6540
cttcgcttgg cccgacgcga cgctgctggt tcgctggttg gtgtccgtta gactcgtcga   6600
cggcgttgaa cagcctgtca ttatctactc gaaacaagaa aaatgtttgc ttagttttt   6660 tatttcttaa agggtatttg tttatttgt agtcaattta ttttatttca ttttatatct   6720
aaattattaa ataaaaaact aaaatagagt tttagtttta aaaatttag agactaaaaa   6780 gaataaaatg gatgtactaa aaattagtct atagaaacca tcaaccctaa atcctaaatg   6840
gatgtactaa taaatggat gaagtattat ataggtcaag ctatttgcaa aaaaaacaga   6900
gagatcacat gcacactaaa aagataaaac tgtagattgt caaatattc aattatcctt   6960 tagaccatgt ctagcagttt atttatatga tcctctaaaa cactaatatt attttagtat   7020
tatagactat attatttgta gagtgaagtt taaatatatg tatagagata gataaactac   7080
acttcaaata agtgtgacaa aaaaatatgt ggtaattttt tatactttag acatgcaatg   7140
ctctttatct ctagagaggg gcacgacgca tgcaagcttg ttaacgcggc cgctaattct   7200
cagtccaaag cctcaacaag gtcagggtac agagtctcca aaccattagc caaaagctac   7260
aggagatcaa tgaagaatct tcaatcaaag taaactactg ttccagcaca tgcatcatgg   7320
tcagtaagtt tcagaaaaag acatccaccg aagacttaaa gttagtgggc atcttttgaaa   7380 gtaatcttgt caacatcgag cagctggctt gtggggacca gacaaaaaag gaatggtgca   7440
gaattgttag gcgcacctac caaaagcatc tttgccttta ttgcaaagat aaagcagatt   7500
cctctagtac aagtggggaa caaaataacg tggaaaagag ctgtcctgac agcccactca   7560
ctaatgcgta tgacgaacgc agtgacgacc acaaaagaat tagcttgagc tcaggattta   7620
gcagcattcc agattgggtt caatcaacaa ggtacgagcc atatcacttt attcaaattg   7680
gtatcgccaa aaccaagaag gaactcccat cctcaaaggt ttgtaaggaa ggtcgaggcc   7740
gctgtactgt catattgtcg tggtttttca attgctgtac ctgatgcaaa cgtaatgggt   7800
ttactaatct tgcacccgcc ggcttcaaaa tgaagagtgc taatttggtc cacgtcacca   7860
tcaccggttc gaactgtcta gaatggcagg caaagatgat tggacaggca tgcagggaaa   7920
aagagcaccg ttgacgatgt atgcgagttc ccaccattgc gagcaatgat tatcagccac   7980
acgacttact cttcagagct aaccactgcc atgcagagaa aaagtgaatc atattgtcat   8040
gatctacaac gaagtgaaac aatcaggcat gctaaagtgc tgaaacttta ctgatctctc   8100
```

```
atgttggaca acaaagaata cgggaataca tcagcaacgc aactcttgag ctttgcttgc    8160
cgaatgacca gctagaattt ccaagcattt acagaaacat gactttaagt ttcagaaaaa    8220
caaatacaag gccactaaat aagcgtgggg ataacatatc ctccagatga caggcaatct    8280
gcaacttgca gccattcaaa tgtacgatta acaaaatatt taagcgccac atgagataat    8340
atatcctcca attagggcct ttagtattgt cattagctca taaccatggt gcatcctcac    8400
atggacgctg cataagaagt tcataatagc aacagacata tgaacaaagc atggtgcgcc    8460
tgcccggccg gactagctag tactaccaat catggaataa gctagtaccc taaatgaaat    8520
taaaatggtt tttagcgatt atccacgccg tccagaatac tctaatccac aagttgaggc    8580
cgcccatgaa gccgcgagag ggcgacgcca tgtgtataaa aggggcctaa gctgagtgga    8640
cttgctgcat cagattagta agcaatctca agcgcagaga gccaaagctt tcggtgtagc    8700
tcgaagagca aagcgaaggc aaggcgcgcc tgtaacctac ctaccaacct cgccattcct    8760
ctccaaactg ttgtgctgct gtctagatct cccacactac actagttact cctcgtagat    8820
ctcggctacc tggctcaaga tccggggtca gatccgggtc cggggatttt ctttgtgccc    8880
tatgctgta ttttggcgtc tgtggctgat gacagcgtgt gttctcgagt gcggatgcaa    8940
tctgagttat ataggcaaat ggccttgtca actcgggcag cggcattgct ttgctcagtg    9000
tgtttgaatg tgctgaaatt catgtagtag gctgtaggct gtgcatttct tgatttgcgt    9060
cttgcataat tcactggtgg attttctaaa cctaacaagt ttaaaattag accattcaac    9120
caaagacagg aggaataagt gaagctgttg tagtcacagc ttatggccga tccaaaattt    9180
gttaggaatg tgaatatgtg atgctacaaa catatccttg taagctacca tgctatttat    9240
catgttccat catggtgatt ggtgagcact catgaaaatt tcagatccaa acctagtgtt    9300
acatgtggat ttgtgctctg caatctatcg ccagtaataa aatggttgag tgatccagct    9360
actacaaaat cacattgcat actttttttt tttgtagatt atgcatcctg gttttgggtg    9420
gtgggttcct gatgtcagga atataaattt agcctgctga tttaggtagc actgccggtg    9480
cacactttgg tttttgaata cttgtagtct tccagcttct tgtagaactg gtacaatgtg    9540
ggccatatat aagaagggct gtcaactagc acatgctcac taattagtct aaacatttat    9600
gtttttattc attcaggtca ggtgcaatca tagaagtagt taatgacaat actttagttg    9660
ttctaatatt atttatgtat ggactcaaat taacatgcaa aacatatgag attagtggca    9720
tgcattcttt ttcttaatag tggaaaatac gagataatga taactgtgaa gctctgttag    9780
tactcttcat tactctattt gagtggcagc atatctcatg ctagccataa agcaagttct    9840
agacgtattc tgttgttaat tacttgtagc tatataaccc aacctagtca ttccagctta    9900
tgtctcttag agatcatgtt tattagcacc tcaagatttc ctctgcacag tatagtaact    9960
atcgaaaaag atattatttc tttgttttta attgacaacc ttcacgtgct acttattttt   10020
gcagcttggc cggccaccaa ccatggctga atcaacaac cagaaccagt gcgtcccgta   10080
caactgcctg agcaacccta aggagatcat cctgggtgag gaacgcctgg agaccggcaa   10140
caccgtagcc gacattagcc tgggcctcat caacttcctc tacagcaact tcgtgcccgg   10200
cggtggcttc atcgtgggcc tcctggagct tatctggggc ttcatcggcc cgtcccagtg   10260
ggacatcttc ctcgcccaga tcgagcaact gatcagccag cggatcgagg agttcgctag   10320
gaaccaggcc atctcccgcc tggagggact ctccaacctc tacaaggtgt acgtgcgcgc   10380
gttcagcgac tgggagaagg acccgaccaa cccggccctc cgcgaggaaa tgcgtatcca   10440
```

```
gttcaacgat atgaactcgg ccctcatcac cgccatcccg ctcttccgcg tgcagaacta    10500
cgaggtggcc ctcctgtccg tgtacgttca agccgccaac ctccacctct ccatcctccg    10560
cgacgtgagc gtgttcggcg agcgctgggg ctacgacacc gccaccatca caaccgcta    10620 ctccgacctc acctccctca tccacgttta caccaaccac tgcgtggaca cgtacaacca    10680
gggcctccgc cgcctggagg gccgcttcct ctccgactgg atcgtgtaca accgcttccg    10740 ccgcagctc accatctccg tcctggacat cgtcgccttc tttcccaact acgacatccg    10800
cacctaccct atccagaccg ccacccagct cacccgcgag gtctacctcg acctcccgtt    10860
catcaacgag aacctcagcc cggccgccgt ctacccgacc ttctccgccg ctgagtccgc    10920
catcattcgc agcccgcacc tcgtggactt cctcaactcc ttcaccatct acaccgactc    10980
cctcgcccgc agcgcctact ggggcggtca cctcgtgaac tccttccgca ccggcaccac    11040
taccaacctc atccgcagcc cgctctacgg ccgcgagggc aacaccgagc gcccggtgac    11100
catcaccgcc agcccgagcg tgcccatctt ccgcaccctc agctacccca ccggcctgga    11160
caacagcaac cctgtggcgg gcatcgaggg cgtggagttc cagaacacca tctccaggag    11220
catctaccgc aagagcggcc ctatcgacag cttcagcgag ctgcctcctc aggacgccag    11280
cgtgagccct gccatcggct acagccacag gctgtgccac gccaccttcc tggagcgcat    11340
cagcggccct cgcatcgcgg gcaccgtgtt ctcgtggacc caccgcagcg cctctcctac    11400
gaacgaggtg tctcctagtc gcatcaccca gatcccttgg gtcaaggccc acaccctggc    11460
tagtggcgct agtgtcatca agggccctgg cttcaccggt ggtgacatcc tgaccaggaa    11520
ctctatgggc gagctgggca ctctgagggt cactttcact ggccgcctgc ctcagtctta    11580
ctacatccgc ttccgctacg ctagtgtcgc taaccgctct ggtactttcc gctactctca    11640
gcctccgtct tacggtatct cttcccctaa gactatggac gctggtgagc ctctgaccag    11700
taggagcttc gctcacacta ctctgttcac tcctatcact ttctctaggg ctcaggagga    11760
gttcgacctg tacatccagt ctggtgtgta catcgacagg atcgagttca tccccgtgac    11820
cgccacgttc gaggccgagt acgaccttga gcgcgcccag aaggtggtga acgccctctt    11880
cactagcact aaccagctag gcctgaagac tgacgtgacc gactaccaca tcgaccaagt    11940
gagcaaccta gtggcctgcc tctccgacga gttctgcctc gacgagaagc gcgagctgtc    12000
cgagaaggtg aagcacgcca agcgcctctc cgacagcgcg aacctgctcc aggaccccaa    12060
cttcaggggc atcaacaggc agcccgaccg cggctggcgc ggctccaccg acatcaccat    12120
ccagggcggt gacgacgtat tcaaggagaa ctacgttacc ctccccggca ccttcgacga    12180
gtgttacccc acctacctct accagaagat cgacgagtcc aagctgaagg cctacacccg    12240
ctaccagctc cgcggctaca tcgaggactc ccaggacctg gaaatctacc tcatccgcta    12300
caacgccaag cacgagatcg tgaacgtgcc tggcaccggc agcctctggc ctctcagcgt    12360
ggagaaccag atcggccctt gcggcgagcc taaccgctgc gcccctcacc tcgagtggaa    12420
ccctgacctc cactgctcgt gcaggacgg cgagaagtgc gcccaccata gccaccactt    12480
ctctctggac atcgacgtgg gctgcaccga cctgaacgag gacctgggcg tgtgggttat    12540
cttcaagatc aagacccagg acggtcacgc caggctgggt aacctggagt tccttgagga    12600
aaagcctctg ctgggtgagg ccctggccag ggtcaagagg gctgagaaga aatggaggga    12660
taagagggag accctgcagc tggagaccac tatcgtctac aaggaggcta aggagtctgt    12720
cgatgctctg ttcgtcaact ctcagtacga tagactgcaa gctgatacca acatcgctat    12780
gatccacgct gcggataagc gggtccaccg gatccgggag gcttaccttc cggagctttc    12840
```

```
tgtcatcccg ggtgtcaacg ctgcgatctt cgaggaactt gaggaacgga tcttcactgc    12900
gtttagtctt tacgatgcgc ggaacatcat caagaacggg gacttcaaca atggtctgct    12960
gtgctggaac gtcaagggtc atgtcgaggt cgaggaacaa acaatcatc gtagtgtcct     13020 tgtcattcct gagtgggagg cggaggtctc tcaagaggtc cgtgtttgcc cggggcgtgg    13080
gtacattctt cgtgttactg cgtacaagga ggggtacggg gaggggtgcg ttactattca    13140
tgagattgag aacaatactg atgagcttaa gttcaacaat tgtgttgagg aggaggttta    13200
cccgaacaat actgttacgt gcatcaacta cacggcaacg caagaggaat acgaggggac    13260
gtacacctcg cgtaatagag ggtatgatga ggcgtacgga aacaacccgt cggttccagc    13320
agattatgcc tcggtttatg aggagaagtc gtacacggat agacgacgcg agaatccatg    13380
tgagtcaaat cgaggatacg gagattacac accattacca gcaggatacg ttacaaagga    13440
gttggaatac ttcccggaaa cagataaagt ttggattgaa atcggagaaa cagaaggaac    13500
attcatcgtc gactcagtag aattgttgtt gatggaagaa tgataggac cccggacccg     13560 ccaaaaccat tgcaaagact atagtttggg gtggagtata cttggttgtg tacatgcctg    13620
cgtgttccat tgtacacaca aaacctagcc acctcttgac tcttgagtgt atgcttgtta    13680
tccgtgtgtt gaagtttgta agaggcacca tcactataga tgatggcttg tgtccctctt    13740
tcatcaagat tgaataatat atgctacttt gagagcgcta tcctgcttgc ctgattgtgt    13800
taatacttac atccgtccca cactcccaca atataaggaa ataaggtatt ttggcagttt    13860
agagcaaaat tcccttatat ttttgggacg gatgtcctct tttctgcatt tttttatgtt    13920
catatgttcc tgaagagtaa ggtggatctt gatcaacctg tcggtttatg gtgattgatt    13980
tgagtggaat agaatgggcc aacgtccggc atacagttat gcttcagtta attaaaagta    14040
agggtcccaa gtaaggccgg ccaagtaacg gtccgaagta aggcgcgggt accgtcggtc    14100
cgggcctagt aggccaagca ggacgtggcg cgccaagaag aacgattggc aaacagctat    14160
tatgggtatt atgggtaggc acatgggaat atagtgggag gcagaggcgt gcctgtgcct    14220
gctcttaatt tgagctcctc ccctggccct gataggggcat gtgcatgcgc acaataatca    14280
ttggagctgc ctgaatgatt tgcatgcgct cgtgtaaaac gttcacggtc catgccagtc    14340
caagaccgtc ggcaagagat gagggccatg cgcagtacgt acatttgtat acatatacat    14400
atttttttgg atgatgcgat gcgtgtgcat atctggctgc gccgctccct cgtccatcgt    14460
cgtcgcggtg tacaacgaat tttccgtggg atgggctgaa cttataatgg gcctactggg    14520
cgggccgtat gaaatagcac acaattcacc ctgcttttct caccaggaat gcattttcgc    14580
gggagccatc gtcctaactt ggcagacaga cacacaaaca caggacagga gttcgccaac    14640
cccagcatga gagaaaccta tccggacagc tcctccagcc tatgggccgt tgggccttca    14700
gcctcagcgc cccggccccg tgggcgggca aaacactcca cagtccacac ggctgctgct    14760
gctgcccttg ttccgtcgga cctggggtaa ctttatagct atgatgttcg cccttcccaa    14820
ccaatgtgcg agcgttaagg atgttaagta acactagtta ggattatgtg ccaaatacc     14880 tactttgcta ggaacttgta caccccctcat aatatagaga aaagaaagat gccagtggtc    14940
caactctata ccatgtgtct cgtgtgtttg ttatgtcgtg cttatgtgaa gggagacgag    15000
tcttctacag cttctcacgc ctaatctgtt gacgggagag aagagagcgg atctggtgat    15060
ccgtggtaac gtagttctca acaaatgaca cattgagcac accgttgtca tctcctcagc    15120
```

```
taaacattga gggggatttt tttttaagaa aggctgagat tcccttacgc tccctttggc    15180
agggctcgtc caacagcttc ttgaaaaatt ctataa                              15216

<210> SEQ ID NO 11
<211> LENGTH: 862
<212> TYPE: DNA
<213> ORGANISM: Zea mays
<220> FEATURE:
<221> NAME/KEY: misc_feature
<222> LOCATION: (1)..(862)
<223> OTHER INFORMATION: 862 nucleotide sequence representing the 5'
      flanking corn genomic DNA.

<400> SEQUENCE: 11
cgcagcgcag gtccgtgtgg cctgtttgtt ttggcttctg gtagcttctg gccaccaaaa    60
gctgctgcgg actgccaaac gctcagcttt tcagccagct tctataaaat ttgttggggg    120
gcaaaaacca tccaaaatca acataaacac ataatcagtt gagtcgttgt aatagtagga    180
attcgtcact ttctagatcc tgagccctat gaacaatttt atcttcctcc acacgtaatc    240
gtaatgatat tcagattctc cccacagcca gattctcctc acagccagat tttcagaaaa    300
gctggtcaga aaaagctga accaaacagg ccctaggaca cataggaa tggatcaaaa      360 aacatagcgc cgtacccgta cgtacgtgca gtcacagtca gctgctagct agctagctgc    420
gccggcggcg gcgttgtcgg tcttgactca acgacgtccg cggctggcgc cgtcggccag    480
cggcttgttg ccgccggtcc catccggcgg agtccggctg ccagtggccg gcggcggctt    540
cttcttcgtc gtcgtcctgc cctttgccat ccccgctgcc acctggacga gggttctggc    600
tcccgtcgac gtcgacgaga gacgtggcgc cgcatttggc tgccgccgta tcgtcgtcgt    660
cgtcgagatt gaaatcgaga gggagcgcgc gggatggctg ccgccggtgg cgcgacatgg    720
tctcgcccgg ccggcgcctg atcgacttct cttccgccgc cttcgctagc tatagcttgg    780
tagtagtcac caacaacgac ctagggagct agcgtacgtt cgaggtacct gtcctgcaag    840
caaatgtgtg gtagtggtcc aa                                            862

<210> SEQ ID NO 12
<211> LENGTH: 1036
<212> TYPE: DNA
<213> ORGANISM: Zea mays
<220> FEATURE:
<221> NAME/KEY: misc_feature
<222> LOCATION: (1)..(1036)
<223> OTHER INFORMATION: 1036 nucleotide sequence representing the 3'
      flanking corn genomic DNA.

<400> SEQUENCE: 12
acatgggaat atagtgggag gcagaggcgt gcctgtgcct gctcttaatt tgagctcctc    60
ccctggccct gatagggcat gtgcatgcgc acaataatca ttggagctgc ctgaatgatt    120
tgcatgcgct cgtgtaaaac gttcacggtc catgccagtc caagaccgtc ggcaagagat    180
gagggccatg cgcagtacgt acatttgtat acatatacat attttttttgg atgatgcgat    240 gcgtgtgcat atctggctgc gccgctccct cgtccatcgt cgtcgcggtg tacaacgaat    300
tttccgtggg atgggctgaa cttataatgg gcctactggg cgggccgtat gaaatagcac    360
acaattcacc ctgctttttct caccaggaat gcattttcgc gggagccatc gtcctaactt    420
ggcagacaga cacacaaaca caggacagga gttcgccaac cccagcatga gagaaaccta    480
tccggacagc tcctccagcc tatgggccgt tgggccttca gcctcagcgc cccggccccg    540
```

```
tgggcgggca aaacactcca cagtccacac ggctgctgct gctgcccttg ttccgtcgga    600
cctggggtaa ctttatagct atgatgttcg cccttcccaa ccaatgtgcg agcgttaagg    660
atgttaagta acactagtta ggattatgtg gccaaatacc tactttgcta ggaacttgta    720 caccoctcat aatatagaga aaagaaagat gccagtggtc caactctata ccatgtgtct    780
cgtgtgtttg ttatgtcgtg cttatgtgaa gggagacgag tcttctacag cttctcacgc    840
ctaatctgtt gacgggagag aagagagcgg atctggtgat ccgtggtaac gtagttctca    900
acaaatgaca cattgagcac accgttgtca tctcctcagc taaacattga gggggatttt    960
tttttaagaa aggctgagat tcccttacgc tcccttggc agggctcgtc caacagcttc    1020
ttgaaaaatt ctataa                                                    1036
```

<210> SEQ ID NO 13
<211> LENGTH: 18376
<212> TYPE: DNA
<213> ORGANISM: Artificial
<220> FEATURE:
<223> OTHER INFORMATION: Sequence representing the transgene cassette
      comprised within the binary plasmid transformation vector used to
      transform corn to produce corn event MON 95379.

<400> SEQUENCE: 13

```
aaaagtccca tgtggatcac tccgttgccc cgtcgctcac cgtgttgggg ggaaggtgca     60
catggctcag ttctcaatgg aaattatctg cctaaccggc tcagttctgc gtagaaacca    120
acatgcaagc tccaccgggt gcaaagcggg agcggcggca ggatatattc aattgtaaat    180
ggcttcatgt ccgggaaatc tacatggatc agcaatgagt atgatggtca atatggagaa    240
aaagaaagag taattaccaa ttttttttca attcaaaaat gtagatgtcc gcagcgttat    300
tataaaatga aagtacattt tgataaaacg acaaattacg atccgtcgta tttataggcg    360
aaagcaataa acaaattatt ctaattcgga aatctttatt tcgacgtgtc tacattcacg    420
tccaaatggg ggcttagatg agaaacttca cgatcgatgc ggccaccacg agtcgacata    480
acttcgtata gcatacatta tacgaagtta tactagttgg tgttttctgt tacagagcaa    540 cttttatcata gttaggaact tgggtgtggc tctagccgct cccagtcgaa tgtttctaaa    600
ttaaaaatcc aaacaaaaat cactgaggtt tacttgggac acaatcttta cacagctacg    660
tattcacgcg ttctcttttc acacagctac gtattctggt gaggagcatt tacttaggaa    720
catcacttag ctcacctaag cagcgacgat ctcaagattg cgaaccagag aatcagatat    780
ccaaaactag tttcacgcca actaaaggtc acaattattc tcgagcaaaa aaacgatttc    840
aatgctatag acacaacttt acgaagtaga ggcttcgttt tacgacaaac cacgaacttg    900
gatattaaag atgccacaaa gaaggttcac ataaacaaca caggtcacag cagcgaaagc    960
tacaagcaaa ccctacataa tcgaaaagca aatgttttc aaaaccagac acacaaactg    1020
atagatagaa gcccacacgg acagatcata ggatagcagc agtaatcaag cattgccaag    1080
gcaccaggca agaaccctgg agctcatcag gcagccttcg tatcggagag ttcgatcttc    1140
gcgcccagcc cggccatcag gtccatgaac tccgggaagc tcgtggcgat catcgtggca    1200
tcgtccaccg tgacagggtt ttccgacacg aggcccatga cgaggaagct catggcgatg    1260
cggtgatcga gatgggtggc gacggcggcg cccgaggcgt tgccgagccc cttgccgtca    1320
gggcggccac gcacgacgag cgacgtctcg ccctcatcgc aatccacgcc attgagcttg    1380
aggccattgg cgacggccga gaggcggtcg ctttccttga cgcggagttc ttccagaccg    1440
ttcatcacgg tcgcccctc cgcgaaggcg gcggcgacag cgagaatcgg atattcgtcg    1500
```

```
atcatcgaag gcgcgcggtc ttccggcacc gtgacgccct tcagcgtgga ggagcgaacg    1560
cgcaggtccg ccacgtcttc gccgccggca aggcgcgggt tgatgacttc gatgtcggcg    1620
cccatttcct gcagcgtcag gatgaggccg gtgcgggtgg ggttcatcag cacgttgagg    1680
atggtgacgt cggagcccgg aacaagcagg gccgcaacca gcgggaaggc cgtcgaggac    1740
gggtcgcccg gcacgtcgat gacttggccg gtgagcttgc cgcggccttc caggcggatg    1800
gtgcgcacgc cgtccgcatc cgtctcgacg gtaaggttgg cgccaaagcc ctgcagcatc    1860
ttttccgtat gatcgcgcgt catgatcggc tcgatgaccg tcgtgatgcc gggcgtgttg    1920
aggccggcga gcagcacggc ggacttcacc tgtgcgagg ccatcggcac gcggtaggtg    1980
atcggcgtcg gcgtcttcgg cccgcgcaag gtaacgggaa gacggtcacc gtcttccgat    2040
ttcacctgca cgcccatttc gcgcagcggg ttcaacacgc ggcccatcgg gcgctttgtg    2100
agcgaggcgt cgccgatgaa ggtgctgtcg aaatcgtaga ccccgacgag gcccatcgtc    2160
aggcggcagc ccgtggcggc attgccgaaa tcgagcggcg cctcaggcgc caggaggccg    2220
ccattgccga cgccatcgat gatccaggtg tcgccttcct tacggatgcg ggcgcccatc    2280
gcctgcatgg ccttgcccgt attgatgacg tcctcgcctt ccagaaggcc ggtgatgcgc    2340
gtttcaccgc tcgcgagacc gccgaacatg aaggaccggt gggagatcga cttgtcgccg    2400
ggaatgcgga cggttccgga aaggccgag gatttgcggg cggttgcggg ccggctgctt    2460
gcaccgtgaa gcatgcacgc cgtggaaaca gaagacatga ccttaagagg acgaagctca    2520
gagccaatta acgtcatccc actcttcttc aatccccacg acgacgaaat cggataagct    2580
cgtggatgct gctgcgtctt cagagaaacc gataagggag atttgcgttg actggatttc    2640
gagagattgg agataagaga tgggttctgc acaccattgc agattctgct aacttgcgcc    2700
atggatcagg ctgcatagga caaaacaaga tttcaacaaa ttacgcctta agaattttt    2760 ttatcacagg atttatcaag acaagacgaa cagggagtca caggtgaacc aatccacata    2820
atacagcctt tcagatagcg ttctaatgac ctttaagaat ataatagcac ctatcttcag    2880
atcagatcaa aagattacta cgcagaaacg agcactacaa agcatgatac caaagaccat    2940
caaatagttg cccaatctgt ctaaatattt ttttctgtgc ttgctctgaa atagttctta    3000
gctcgcagca atgtacatac tacagatcca catactccgt ccatacatgt gcctaagtta    3060
cagatctatt cataataagc aacaaattaa gtataaacgg gagtacaaat ctaggtgaac    3120
agcagtaaaa tatcaagatc catcaaccaa aggggcattt cagcacggat catggcaatc    3180
caaccagatc cgcatgccat tcctatacaa cctaggtaga aaatttgaaa aaacaaacaa    3240
gcattgatca gatctatccg aaacaaacat acactaacca gatctaccaa aaaggaacag    3300
attatcagca gggagacaga ctaattcagt ggatccccat ccgaaacccc cctaatattg    3360
catcatttcc cgattcttag cgtctcactg ccagatccaa acatttcgc cagatccacg    3420 aactaccact gatcaaaacg cagatccgga catcgacaac cacagaaggc cagatccacc    3480
gacagatcta tcaaacagaa cgaaccacac cccaggatca cccagatcca cccacagatc    3540
gaagcgcgct actacgagaa acggaggaat ggaagcatca gatccgtttt tgtttgtttt    3600
acctggatgg ctagccggtg gcggcggaga cgaacggcgc cgagcggcgg cggaggaggg    3660
cgcggagaga ggcgagtacg aagacgcctt tctctgcggt gtggtagggt ttccacctcc    3720
cactcctccc ctttctatag agcgggaggc gcctcggcgt ttttgcgttt aaccccctcg    3780
attaagtttc ccaattttac actccgctcc actttggctc ctccaacggt caggaactgt    3840
```

-continued

```
actggtttgg aatatcggaa tttttctgag ggttttagtg caaaatattc atgccgtttt    3900
gtttagtgtg ggtgggtaag agtccagatc tacccgccgc tcactgggag gtgggcccac    3960
tggttgctgc gagcgactga cgtctcgctt gtaggtgggc ccacaagggt gggaccggat    4020
tgtcagtggc gtgtggggttg gtgggcgtag ttggggtaga attcgagggg ttgttccgtc    4080
attttccgcc cgctccgtcg gcggccagtc gtgccgatat ttttggattt tgaaattcaa    4140
gagcgggagc caggaggggg agggtggtgg caggcctggc ccatgatcta ttgtttgctc    4200
ggatgggcct tgggcctaac tgttagtttt gattctgttt gtaattaact cttttttgaaa   4260 ggaataaaaa gaaccatgct acctgacggg ttgatgtttt accattgaga tttcaaaggg    4320
gttaaagtga aattgaaact caattcgaac atgatttaaa ttgttttgaa ctcccttcga    4380
attgagggca gttttagtgg ttataaatct tcatcgagag aatttttctg atgttttat     4440 ggaatttgat gtcctaagag cacctctaac aggcaacatc ctctccaaat ggctctcaaa    4500 ctatttttt ttgacaattc tagtaaaaag atactacccc aataacctt ccaaccggat      4560 ggccaaatcc ctcccttat tggcctaact tggcaaccca aaataacttg ccaaacggta     4620
ggccccatgt actattcctc ctccccacat ggctactctc ctcttctctc tctctcttat    4680
gttgacggag aggaggcgtt gacggtggct gttgggcgaa gctagggtag tgcggtggtg    4740
gaggtgaagc ggtggctgtg ctaaagctcg cccctggcat tggtggtgtg ggagagctgg    4800
ccagtggcta gtgtgacaat ggaggtgacc aggcgacact ttctccctcc ctcttccctc    4860
catgttgatg agaagcatgt tgttgtccct aggataactt cgtatagcat acattatacg    4920
aagttatagc ggccgcaaat caacctcact ctatttaaat gaggtggtag datttgccgc    4980
gtgagaccta ttaccctgtt atccctagtt taaacacctg caggaaaaga ttaattaaca    5040
tcgatcatca tgttcaattg acagcaaatt aaactagtta tatatagggt tcatgagatg    5100
agagtagcta attattaaca caagtggaag aaactttat ttgacggtat acaaataaca     5160
agatacagag atcaggctga tgatcaatc atatcatatc agtgatagat cgatcgttcg     5220
acacatatat atgtatgaca aaacatagta taagtacgtg cgaaagggtt tatatatata    5280
tggatattga tgcatggtgt aatggtatgg taattaaggg atcggaggat cgattaatgg    5340
gtccctatca ctcctccatc agtagcagct cgaccgagtc cacgatgaaa gtgccctccg    5400
tctcgccgat ctcgatccag actttgtcgg tctccgggaa gtactccagc tccttggtga    5460
cgtacccggc gggcagcgga gtgtagtcac cgtagccacg gttggactcg caagggttgt    5520
ccctccgtcc gtcggtgtac gccttctcct cgtaagcgga cgcataatcc gcaggcacgc    5580
tgctgttgga ctcgtacgcg ccatcatagc cgcgattccg ggaagtgtaa gtgccctcgt    5640
actcctcttg cgtggcagtg tagtcgttgc aagtaacggt gttgttcggg tacacctcct    5700
cctccacaca gttcgagaac ttgagctcgt cggtgttgtt ctcgatctcg tggatagtca    5760
cgcagccttc accgtagcct tccttgtacg cagtcacacg gaggatgtag ccgcgaccag    5820
ggcagacgcg gacctcctgg ctcacctctg cctcccactc cggcacgacc agcacggacc    5880
ggtggttgtt ctgctcctcg acgtccacat ggcccttgac gttccagcaa ctcagcccgt    5940
tgttgaagtc accgttctta ataacattcc tggcatcgta caggctgaat gctgtgaaga    6000
tgcggccctc cagttcctcg aagatcgccg cgttcacacc agggatcact gacagctcgg    6060
gcaggtacgc ctcacggatg ctgtggaccc gcttgtcagc cgcgtggatc atggcgatgt    6120
tggtgtcagc ctggaggcgg tcgtactggc tgttgacgaa gagtgcgtcc actgactcct    6180
tggcctcctt gtacacgatg ttggtctccc actccagctt ctcccgcttg tctcgccatt    6240
```

```
tcttctcggc gcgcttcaca cgagcgaggg cctcgcccac gagaggcttc tcctcaagga   6300
actccaggtt gccgaggcgg gcatgtccgt cctgggtctt aatcttgaag ataacccaga   6360
cacccaggtc ctcgttgagg tcggtgcagc ccacgtcgat gtccagagag aagtggtgcg   6420
agtggtgagc gcactttccg attggagagg gagcgctcaa tggccaaagt gagcccgtgc   6480
ctggcacgtt cactgtctcg tgcttggcgt tgtatcggat caggtagatt ccaggtcct    6540 gactatcctc gatgtacccg cgaagctggt agcgggtgta cgccttcaat ttactctcgt   6600
ctatcttctg gtagagatac gtcgggtagc attcgtcgaa agtcccgagc agcgtcacat   6660
agttctcctt gaacacatcg tcgcctccct ggatggtgat gtctgtactc ccgcgccaac   6720
cacggtcgag ctggcggttg atgccacgga agttcgggtc ctggagcaaa ttccgctcgt   6780
cactcagacg cttcgcgtgt ttgaccttct cggacagctc cttcttctcg tcgaggcaga   6840
actcgtcgga caggcactcc acaaggttgg acacttggtc aatgtgatag tccgtgacgt   6900
cggtcttgag cccaatctgg ttgctgctgg tgaacagttc gttgacagcc ttctgagccc   6960
gctccaggtc agactcggcc tcgaacgtcg catccgccag gatgatctca atcttgtcga   7020
tgtacagttc gccagagctg atggagccag caccgaacag cggttgctcg agatcccaa    7080 tgatgtcagg gttcgctctg aatgagaaag ggttcgagaa atcagtgtac cggaaggttc   7140
ggctagtcaa gttctcgcct atctccatcg tcttctggag aggcatgttg actgagactt   7200
ggcctcccac gcctgtggac gcggctccgg tcaggacaat gaccctcgcg tcgcggcttg   7260
aagcgtagcg gaacctcaga cggtaacgct gggtgatcgg cgagttgatg ttcacttgca   7320
acgaaacgaa gtcgccgaaa gtgttgcgcc gcagtatgtc tccaccggtg aagcccggac   7380
cggtgatgac gctcgtgcca ccccacacac ggaagcccct cacgagcggg atctggttaa   7440
tggagtcgga agagatcgtg ttggtccggt cggcgctgcg gtgtgtccag gagtacaccg   7500
gcgcacgcag cgtgttgcca gagatgagcg ggatgttgga caggcggtgg ctgtaggact   7560
cgtagttcgg gcgttccgtg gtctcgggcg gcagctcagt ttcactgtcg aagagctggg   7620
tgccgacgcc cgtgtacccg atggtgtaga gcaatgaccc gcgcaggag ttcaacgggt    7680 tacgccagtt gaaccgggcc cacgggacgc cgttgacggg cgttgtcaga aggatgttaa   7740
tgcccgcgaa cgactcagtc cggtaaacgt cgcggctcgt gaactgtagc gtaactgggt   7800
tgatggaggt gttggtgttg ccgtgggtac tggtgctcaa gctgccacgg atcgtcctac   7860
tctccaatcg gtgcccgacc cagtagttca tgtactgtgt gttggaccag cgtgagagca   7920
cggagaagat cgtgagctgc tcgggaaagt cgagcaggtg aggagggcgg atgacggcgg   7980
cctcgattgc cgagaaggag ggtgcgttgt tgttgaacca attcgtggat gcgaaaccgg   8040
agggtgcgtt cgtccggccg attgggtctg tgtagatctc ccgcgtgagt tgcgcgctag   8100
tgttcattgg gtacacccgt gtgtcgtaag acgggaatag cgccaccagg tctaggacac   8160
ccaaagtcaa gtcgcggcgg aactggttgt aacggagcca tgactcagcg ttggtgccgc   8220
gcaggttgtt gagccctgtg ttgtaccatc gagcgcagta gtcactgtac tcacgggtct   8280
tctccacttg gcgctcgtag taacgctgga tttcttgaga tgtgagtccg aactcggagc   8340
cgaacaggct ggcgtcccgc agcaggagca gatgtaagtt ggcggcctgg gcgtacacca   8400
taaggagtgg aacttcctgg ttcctgatgg cgaacagcgg catagcgttc aggaagtcga   8460
gttcgagagc gatgtactgg gtgtagagta ccgagcgtgt tcgcgcgtca tccctgttct   8520
ccaaccagtc ctccagtgac tgctggtatg cccgaaagga gtttcccagg ccctgtagcc   8580
```

```
tggccagagc agtatcgcgg gtgttctccg tgacttgctg ccggatcaac tgctccacat   8640
gctccaggaa gatctcccac gggtcacgac cgcgaggcca cagctcgccc acaaggaacg   8700
agtagaagga cgcgatctga ccggcgaatg ggacaccgag gacgccgagg atacggcccg   8760
cgatgttgat gccggtctga accgtgctgg ccgacacgaa tgggtcgatg ttgttgccct   8820
cggctatgca gagggagtcc tcgatgcgcg cgtcggtgga caggttcatc tgcgcggagt   8880
ggtttgaaac agcagggatc gagagggcgt tgatgatctc gttctcgttc ttccggttgc   8940
tcgtcatggt ggtggccggc caagtaacgg tccgacctgc agaagtatca ccaaacaaca   9000
gggtgagcat cggacaaaag aaacagtacc aagcaaataa atagcgtatg aaggcagggc   9060
taaaaaatcc acatatagct gctgcatatg ccatcatcca agtatatcaa gatcaaaata   9120
attataaaac atacttgttt attataatag ataggtactc aaggttagag catatgaata   9180
gatgccgcat atgccatcat gtatatgcat cagtaaaacc cacatcaaca tgtataccta   9240
tcctagatca atatttccat ccatcatctt aaactcgtaa ctatgaagat gtatggcaca   9300
cacataaaga tacaaaatta ataaatccac caggtagttt gaaacagtat tctactccga   9360
tctagaacga ccgcccaacc agaccacatc atcacaacca agcgaaaaaa agcatctctg   9420
tatatgcatc agtaaaaccc gcatcaacat gtatacctat cctagatcga tatttccatc   9480
catcatctta aactcgtaac tatgaagatg taggcacata catacagatc ctttaataaa   9540
tccaccaggt agtttgaaac agtattctac tccgatctag aacgaccctt tatcctttaa   9600
taaatccacc aggtagtttg aaacagtatt ctactccgat ctagaacgac cgcccaacca   9660
gaccatatca tcacaaccaa gcgagaaaaa agcatctct gtatatgcat cagtaaaaccс   9720
cgcatcaaca tgtataccta tcctagatcg atatttccat ccatcatctt aaactcgtaa   9780
ctatgaagat gtatggcaca cacatacaga tacaaaatta ataaatccac caggtagctt   9840
gaaacagtat cctactccga tctagaacga ccgcccaacc agaccacatc atcacaaaca   9900
tgaacatgaa catgtttgct ctaacacaaa catgaacaga agtagaacta ccgggcccta   9960
accatggacc ggatcgccga tctagagaag gtagagagag ggggggggggg aggatgagcg  10020
gcgtaccttg aagcggaggt gccgacggct ggatttgggg gagatctggt tgcgtgtgtg  10080
tgcgctccga acgaacacga ggttggggaa agagggtgtg gaggggtgt ctatttatta   10140
cggcgggcga ggaagggaaa gcgaaggagc ggtgggaaag gaatccccccg tagctgccgg  10200
tgccgtgaga ggaggaagag gccgcctgcc gtgccgcctc acgtctgccg ctccgccacg  10260
caatttctgg atgccgacag cggagcaagt ccaacggtgg agcggaactc tcgagagggg  10320
tccagaggca gctacagaga tgccgtgccg tctgcttcgc ttggcccgac gcgacgctgc  10380
tggttcgctg gttggtgtcc gttagactcg tcgacggcgt tgaacagcct gtcattatct  10440
actcgaaaca agaaaaatgt tgcttagtt ttttatttc ttaagggta tttgtttat    10500
ttgtagtcaa tttatttat ttcattttat atctaaatta ttaaataaaa aactaaaata   10560
gagttttagt tttaaaaaat ttagagacta aaaagaataa aatggatgta ctaaaaatta   10620
gtctatagaa accatcaacc ctaaatccta aatggatgta ctaataaaat ggatgaagta   10680
ttatataggt caagctattt gcaaaaaaaa cagagagatc acatgcacac taaaagata   10740
aaactgtaga ttgtcaaaat attcaattat cctttagacc atgtctagca gtttatttat   10800
atgatcctct aaaacactaa tattatttta gtattataga ctatattatt tgtagagtga  10860
agtttaaata tatgtataga gatagataaa ctacacttca aataagtgtg acaaaaaaat   10920
atgtggtaat ttttatact ttagacatgc aatgctcttt atctctagag aggggcacga    10980
```

```
cgcatgcaag cttgttaacg cggccgctaa ttctcagtcc aaagcctcaa caaggtcagg   11040
gtacagagtc tccaaaccat tagccaaaag ctacaggaga tcaatgaaga atcttcaatc   11100
aaagtaaact actgttccag cacatgcatc atggtcagta agtttcagaa aaagacatcc   11160
accgaagact taaagttagt gggcatcttt gaaagtaatc ttgtcaacat cgagcagctg   11220
gcttgtgggg accagacaaa aaaggaatgg tgcagaattg ttaggcgcac ctaccaaaag   11280
catctttgcc tttattgcaa agataaagca gattcctcta gtacaagtgg ggaacaaaat   11340
aacgtggaaa agagctgtcc tgacagccca ctcactaatg cgtatgacga acgcagtgac   11400
gaccacaaaa gaattagctt gagctcagga tttagcagca ttccagattg ggttcaatca   11460
acaaggtacg agccatatca ctttattcaa attggtatcg ccaaaaccaa gaaggaactc   11520
ccatcctcaa aggtttgtaa ggaaggtcga ggccgctgta ctgtcatatt gtcgtggttt   11580
ttcaattgct gtacctgatg caaacgtaat gggtttacta atcttgcacc cgccggcttc   11640
aaaatgaaga gtgctaattt ggtccacgtc accatcaccg gttcgaactg tctagaatgg   11700
caggcaaaga tgattggaca ggcatgcagg gaaaagagc accgttgacg atgtatgcga   11760
gttcccacca ttgcgagcaa tgattatcag ccacacgact tactcttcag agctaaccac   11820
tgccatgcag agaaaaagtg aatcatattg tcatgatcta caacgaagtg aaacaatcag   11880
gcatgctaaa gtgctgaaac tttactgatc tctcatgttg acaacaaag aatacgggaa   11940 tacatcagca acgcaactct tgagctttgc ttgccgaatg accagctaga atttccaagc   12000
atttacagaa acatgacttt aagtttcaga aaaacaaata caaggccact aaataagcgt   12060
ggggataaca tatcctccag atgacaggca atctgcaact tgcagccatt caaatgtacg   12120
attaacaaaa tatttaagcg ccacatgaga taatatatcc tccaattagg gcctttagta   12180
ttgtcattag ctcataacca tggtgcatcc tcacatggac gctgcataag aagttcataa   12240
tagcaacaga catatgaaca aagcatggtg cgcctgcccg gccggactag ctagtactac   12300
caatcatgga ataagctagt accctaaatg aaattaaaat ggttttagc gattatccac   12360 gccgtccaga atactctaat ccacaagttg aggccgccca tgaagccgcg agagggcgac   12420
gccatgtgta taaaggggc ctaagctgag tggacttgct gcatcagatt agtaagcaat   12480
ctcaagcgca gagagccaaa gctttcggtg tagctcgaag agcaaagcga aggcaaggcg   12540
cgcctgtaac ctacctacca acctcgccat tcctctccaa actgttgtgc tgctgtctag   12600
atctcccaca ctacactagt tactcctcgt agatctcggc tacctggctc aagatccggg   12660
gtcagatccg ggtccgggga ttttctttgt gccctatggc tgtattttgg cgtctgtggc   12720
tgatgacagc gtgtgttctc gagtgcggat gcaatctgag ttatataggc aaatggcctt   12780
gtcaactcgg gcagcggcat tgctttgctc agtgtgtttg aatgtgctga aattcatgta   12840
gtaggctgta ggctgtgcat ttcttgattt gcgtcttgca taattcactg gtggattttc   12900
taaacctaac aagtttaaaa ttagaccatt caaccaaaga caggaggaat aagtgaagct   12960
gttgtagtca cagcttatgg ccgatccaaa atttgttagg aatgtgaata tgtgatgcta   13020
caaacatatc cttgtaagct accatgctat ttatcatgtt ccatcatggt gattggtgag   13080
cactcatgaa aatttcagat ccaaacctag tgttacatgt ggatttgtgc tctgcaatct   13140
atcgccagta ataaaatggt tgagtgatcc agctactaca aaatcacatt gcatactttt   13200 ttttttgta gattatgcat cctggttttg ggtggtgggt tcctgatgtc aggaatataa   13260
atttagcctg ctgatttagg tagcactgcc ggtgcacact ttggttttg aatacttgta   13320
```

-continued

```
gtcttccagc ttcttgtaga actggtacaa tgtgggccat atataagaag ggctgtcaac    13380
tagcacatgc tcactaatta gtctaaacat ttatgttttt attcattcag gtcaggtgca    13440
atcatagaag tagttaatga caatacttta gttgttctaa tattatttat gtatggactc    13500
aaattaacat gcaaaacata tgagattagt ggcatgcatt cttttcctta atagtggaaa    13560
atacgagata atgataactg tgaagctctg ttagtactct tcattactct atttgagtgg    13620
cagcatatct catgctagcc ataaagcaag ttctagacgt attctgttgt taattacttg    13680
tagctatata acccaaccta gtcattccag cttatgtctc ttagagatca tgtttattag    13740
cacctcaaga tttcctctgc acagtatagt aactatcgaa aaagatatta tttctttgtt    13800
tttaattgac aaccttcacg tgctacttat ttttgcagct tggccggcca ccaaccatgg    13860
ctgagatcaa caaccagaac cagtgcgtcc cgtacaactg cctgagcaac cctaaggaga    13920
tcatcctggg tgaggaacgc ctggagaccg gcaacaccgt agccgacatt agcctgggcc    13980
tcatcaactt cctctacagc aacttcgtgc ccggcggtgg cttcatcgtg ggcctcctgg    14040
agcttatctg gggcttcatc ggcccgtccc agtgggacat cttcctcgcc cagatcgagc    14100
aactgatcag ccagcggatc gaggagttcg ctaggaacca ggccatctcc cgcctggagg    14160
gactctccaa cctctacaag gtgtacgtgc gcgcgttcag cgactgggag aaggacccga    14220
ccaacccggc cctccgcgag gaaatgcgta tccagttcaa cgatatgaac tcggccctca    14280
tcaccgccat cccgctcttc cgcgtgcaga actacgaggt ggccctcctg tccgtgtacg    14340
ttcaagccgc caacctccac ctctccatcc tccgcgacgt gagcgtgttc ggcgagcgct    14400
ggggctacga caccgccacc atcaacaacc gctactccga cctcacctcc ctcatccacg    14460
tttacaccaa ccactgcgtg gacacgtaca accagggcct ccgccgcctg agggccgct    14520
tcctctccga ctggatcgtg tacaaccgct tccgccgcca gctcaccatc tccgtcctgg    14580
acatcgtcgc cttctttccc aactacgaca tccgcaccta ccctatccag accgccaccc    14640
agctcacccg cgaggtctac ctcgacctcc cgttcatcaa cgagaacctc agcccggccg    14700
ccgtctaccc gaccttctcc gccgctgagt ccgccatcat tcgcagcccg cacctcgtgg    14760
acttcctcaa ctccttcacc atctacaccg actccctcgc ccgcagcgcc tactggggcg    14820
gtcacctcgt gaactccttc cgcaccggca ccactaccaa cctcatccgc agcccgctct    14880
acggccgcga gggcaacacc gagcgccggg tgaccatcac cgccagcccg agcgtgccca    14940
tcttccgcac cctcagctac cccaccggcc tggacaacag caaccctgtg gcgggcatcg    15000
agggcgtgga gttccagaac accatctcca ggagcatcta ccgcaagagc ggccctatcg    15060
acagcttcag cgagctgcct cctcaggacg ccagcgtgag cctgccatc ggctacagcc    15120
acaggctgtg ccacgccacc ttcctggagc gcatcagcgg ccctcgcatc gcgggcaccg    15180
tgttctcgtg gacccaccgc agcgcctctc ctacgaacga ggtgtctcct agtcgcatca    15240
cccagatccc ttgggtcaag gcccacaccc tggctagtgg cgctagtgtc atcaagggcc    15300
ctggcttcac cggtggtgac atcctgacca ggaactctat gggcgagctg gcactctga    15360
gggtcacttt cactggccgc ctgcctcagt cttactacat ccgcttccgc tacgctagtg    15420
tcgctaaccg ctctggtact ttccgctact ctcagcctcc gtcttacggt atctcttttcc    15480
ctaagactat ggacgctggt gagcctctga ccagtaggag cttcgctcac actactctgt    15540
tcactcctat cactttctct agggctcagg aggagttcga cctgtacatc agtctggtg    15600
tgtacatcga caggatcgag ttcatccccg tgaccgccac gttcgaggcc gagtacgacc    15660
ttgagcgcgc ccagaaggtg gtgaacgccc tcttcactag cactaaccag ctaggcctga    15720
```

-continued

```
agactgacgt gaccgactac cacatcgacc aagtgagcaa cctagtggcc tgcctctccg   15780
acgagttctg cctcgacgag aagcgcgagc tgtccgagaa ggtgaagcac gccaagcgcc   15840
tctccgacga gcgcaacctg ctccaggacc ccaacttcag gggcatcaac aggcagcccg   15900
accgcggctg gcgcggctcc accgacatca ccatccaggg cggtgacgac gtattcaagg   15960
agaactacgt taccctcccc ggcaccttcg acgagtgtta ccccacctac ctctaccaga   16020
agatcgacga gtccaagctg aaggcctaca cccgctacca gctccgcggc tacatcgagg   16080
actcccagga cctggaaatc tacctcatcc gctacaacgc caagcacgag atcgtgaacg   16140
tgcctggcac cggcagcctc tggcctctca gcgtggagaa ccagatcggc ccttgcggcg   16200
agcctaaccg ctgcgcccct cacctcgagt ggaaccctga cctccactgc tcgtgcaggg   16260
acggcgagaa gtgcgcccac catagccacc acttctctct ggacatcgac gtgggctgca   16320
ccgacctgaa cgaggacctg ggcgtgtggg ttatcttcaa gatcaagacc caggacggtc   16380
acgccaggct gggtaacctg gagttccttg aggaaaagcc tctgctgggt gaggccctgg   16440
ccagggtcaa gagggctgag aagaaatgga gggataagag ggagaccctg cagctggaga   16500
ccactatcgt ctacaaggag gctaaggagt ctgtcgatgc tctgttcgtc aactctcagt   16560
acgatagact gcaagctgat accaacatcg ctatgatcca cgctgcggat aagcgggtcc   16620
accggatccg ggaggcttac cttccggagc tttctgtcat cccgggtgtc aacgctgcga   16680
tcttcgagga acttgaggaa cggatcttca ctgcgtttag tctttacgat gcgcggaaca   16740
tcatcaagaa cggggacttc aacaatggtc tgctgtgctg gaacgtcaag ggtcatgtcg   16800
aggtcgagga acaaaacaat catcgtagtg tccttgtcat tcctgagtgg gaggcggagg   16860
tctctcaaga ggtccgtgtt tgcccggggc gtgggtacat tcttcgtgtt actgcgtaca   16920
aggaggggta cgggagggg tgcgttacta ttcatgagat tgagaacaat actgatgagc   16980
ttaagttcaa caattgtgtt gaggaggagg tttacccgaa caatactgtt acgtgcatca   17040
actacacggc aacgcaagag gaatacgagg ggacgtacac ctcgcgtaat agagggtatg   17100
atgaggcgta cggaaacaac ccgtcggttc cagcagatta tgcctcggtt tatgaggaga   17160
agtcgtacac ggatagacga cgcgagaatc catgtgagtc aaatcgagga tacgagatt   17220
acacaccatt accagcagga tacgttacaa aggagttgga atacttcccg gaaacagata   17280
aagtttggat tgaaatcgga gaaacagaag gaacattcat cgtcgactca gtagaattgt   17340
tgttgatgga agaatgatag ggaccccgga cccgccaaaa ccattgcaaa gactatagtt   17400
tggggtggag tatacttggt tgtgtacatg cctgcgtgtt ccattgtaca cacaaaacct   17460
agccacctct tgactcttga gtgtatgctt gttatccgtg tgttgaagtt tgtaagaggc   17520
accatcacta tagatgatgg cttgtgtccc tctttcatca agattgaata atatatgcta   17580
ctttgagagc gctatcctgc ttgcctgatt gtgttaatac ttacatccgt cccacactcc   17640
cacaatataa ggaaataagg tattttggca gtttagagca aaattcccttatatttttgg   17700
gacggatgtc ctcttttctg cattttttta tgttcatatg ttcctgaaga gtaaggtgga   17760
tcttgatcaa cctgtcggtt tatggtgatt gatttgagtg gaatagaatg gccaacgtc   17820
cggcatacag ttatgcttca gttaattaaa agtaagggtc ccaagtaagg ccggccaagt   17880
aacggtccga agtaaggcgc gggtaccgtc ggtccgggcc tagtaggcca agcaggacgt   17940
ggcgcgccaa gaagaacgat tggcaaacag ctattatggg tattatgggt aggcctgccc   18000
gggctcagcc taagtcgcta ccttaggacc gttatagtta ccgggaaact atcagtgttt   18060
```

```
gacaggatat attggcgggt aaacctaaga gaaaagagcg tttattagaa taatcggata    18120
tttaaaaggg cgtgaaaagg tttatccgtt cgtccatttg tatgtgcatg ccaaccacag    18180
ggttcccctc gggagtgctt ggcattccgt gcgataatga cttctgttca accacccaaa    18240
cgtcggaaag cctgacgacg gagcagcatt ccaaaaagat cccttggctc gtctgggtcg    18300
gctagaaggt cgagtgggct gctgtggctt gatccctcaa cgcggtcgcg gacgtagcgc    18360
agcgccgaaa aatcct                                                    18376

<210> SEQ ID NO 14
<211> LENGTH: 35
<212> TYPE: DNA
<213> ORGANISM: Enterobacteria phage P1
<220> FEATURE:
<221> NAME/KEY: misc_feature
<222> LOCATION: (1)..(35)
<223> OTHER INFORMATION: 35 nucleotide sequence representing the LoxP
      sites used for Cre-mediated excision and recombination.

<400> SEQUENCE: 14
ataacttcgt atagcataca ttatacgaag ttata                                35

<210> SEQ ID NO 15
<211> LENGTH: 20
<212> TYPE: DNA
<213> ORGANISM: Artificial
<220> FEATURE:
<223> OTHER INFORMATION: 20 nucleotide sequence corresponding to a
      thermal amplification primer referred to as SQ51219 used to
      identify corn event MON 95379 DNA in a sample.

<400> SEQUENCE: 15
cctgcaagca aatgtgtggt                                                 20

<210> SEQ ID NO 16
<211> LENGTH: 30
<212> TYPE: DNA
<213> ORGANISM: Artificial
<220> FEATURE:
<223> OTHER INFORMATION: 30 nucleotide sequence corresponding to a
      thermal amplification primer referred to as SQ21524 used to
      identify corn event MON 95379 DNA in a sample.

<400> SEQUENCE: 16
gtcgttttat caaaatgtac tttcatttta                                      30

<210> SEQ ID NO 17
<211> LENGTH: 16
<212> TYPE: DNA
<213> ORGANISM: Artificial
<220> FEATURE:
<223> OTHER INFORMATION: 16 nucleotide sequence corresponding to a probe
      referred to as PB10269 used to identify corn event MON 95379 DNA
      in a sample.

<400> SEQUENCE: 17
taacgctgcg gacatc                                                     16

<210> SEQ ID NO 18
<211> LENGTH: 24
<212> TYPE: DNA
<213> ORGANISM: Artificial
<220> FEATURE:
<223> OTHER INFORMATION: 24 nucleotide sequence corresponding to a
      thermal amplification primer referred to as SQ20222 used as an
      internal control for the event and zygosity assay for MON 95379
      and hybridizes to a region of the corn genome.
```

-continued

<400> SEQUENCE: 18
gccctatgac ttaccgagag ttca                                          24

<210> SEQ ID NO 19
<211> LENGTH: 28
<212> TYPE: DNA
<213> ORGANISM: Artificial
<220> FEATURE:
<223> OTHER INFORMATION: 28 nucleotide sequence corresponding to a
      thermal amplification primer referred to as SQ20221 used as an
      internal control for the event and zygosity assay for MON 95379
      and hybridizes to a region of the corn genome.

<400> SEQUENCE: 19
gttgctatgt actaacagaa ctgcatgt                                      28

<210> SEQ ID NO 20
<211> LENGTH: 29
<212> TYPE: DNA
<213> ORGANISM: Artificial
<220> FEATURE:
<223> OTHER INFORMATION: 29 nucleotide sequence corresponding to a probe
      referred to as PB50237 used as an internal control for the event
      and zygosity assay for MON 95379 and hybridizes to a region of the
      corn genome.

<400> SEQUENCE: 20
ttgttgtgtg gctccattct gacttgtga                                     29

<210> SEQ ID NO 21
<211> LENGTH: 20
<212> TYPE: DNA
<213> ORGANISM: Artificial
<220> FEATURE:
<223> OTHER INFORMATION: 20 nucleotide sequence corresponding to a
      thermal amplification primer referred to as SQ50998 used in the
      zygosity assay for event MON 95379 and hybridizes to the coding
      sequence of Cry1B.868.

<400> SEQUENCE: 21
cgggtagcat tcgtcgaaag                                               20

<210> SEQ ID NO 22
<211> LENGTH: 20
<212> TYPE: DNA
<213> ORGANISM: Artificial
<220> FEATURE:
<223> OTHER INFORMATION: 20 nucleotide sequence corresponding to a
      thermal amplification primer referred to as SQ50997 used in the
      zygosity assay for event MON 95379 and hybridizes to the coding
      sequence of Cry1B.868.

<400> SEQUENCE: 22
ggcgacgatg tgttcaagga                                               20

<210> SEQ ID NO 23
<211> LENGTH: 18
<212> TYPE: DNA
<213> ORGANISM: Artificial
<220> FEATURE:
<223> OTHER INFORMATION: 18 nucleotide sequence corresponding to a probe
      referred to as PB50340 used in the zygosity assay for event MON
      95379 and hybridizes to the coding sequence of Cry1B.868.

<400> SEQUENCE: 23
aactatgtga cgctgctc                                               18

<210> SEQ ID NO 24
<211> LENGTH: 19
<212> TYPE: DNA
<213> ORGANISM: Artificial
<220> FEATURE:
<223> OTHER INFORMATION: 19 nucleotide sequence corresponding to a
      thermal amplification primer referred to as SQ50485 used in the
      zygosity assay for event MON 95379 and hybridizes to the coding
      sequence of Cry1Da_7.

<400> SEQUENCE: 24
ggcttacctt ccggagctt                                              19

<210> SEQ ID NO 25
<211> LENGTH: 18
<212> TYPE: DNA
<213> ORGANISM: Artificial
<220> FEATURE:
<223> OTHER INFORMATION: 18 nucleotide sequence corresponding to a
      thermal amplification primer referred to as SQ50484 used in the
      zygosity assay for event MON 95379 and hybridizes to the coding
      sequence of Cry1Da_7.

<400> SEQUENCE: 25
cgaagatcgc agcgttga                                               18

<210> SEQ ID NO 26
<211> LENGTH: 14
<212> TYPE: DNA
<213> ORGANISM: Artificial
<220> FEATURE:
<223> OTHER INFORMATION: 14 nucleotide sequence corresponding to a probe
      referred to as PB50138 used in the zygosity assay for event MON
      95379 and hybridizes to the coding sequence of Cry1Da_7.

<400> SEQUENCE: 26
acccgggatg acag                                                   14

<210> SEQ ID NO 27
<211> LENGTH: 21
<212> TYPE: DNA
<213> ORGANISM: Artificial
<220> FEATURE:
<223> OTHER INFORMATION: 21 nucleotide sequence corresponding to a
      thermal amplification primer referred to as PNEGDNA used in the
      zygosity assay for event MON 95379.

<400> SEQUENCE: 27
ccactgcgcg cgcgccatgg t                                           21

<210> SEQ ID NO 28
<211> LENGTH: 14
<212> TYPE: DNA
<213> ORGANISM: Artificial
<220> FEATURE:
<223> OTHER INFORMATION: 14 nucleotide sequence corresponding to a probe
      referred to as PRBNEGDNA used in the zygosity assay for event MON
      95379.

<400> SEQUENCE: 28
cgtcctccga tcca                                                   14

What is claimed is:

1. A recombinant DNA molecule comprising a nucleotide sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10 and a complete complement thereof.

2. A corn plant, corn plant part, or corn cell comprising a recombinant polynucleotide molecule comprising SEQ ID NO:9 or SEQ ID NO:10.

3. The corn plant, corn plant part, or corn cell, or part thereof of claim 2, wherein:
   a) the corn plant, corn plant part, or corn cell, or part thereof comprises corn event MON 95379; or
   b) the corn plant is a progeny of any generation of a corn plant comprising corn event MON 95379;
   wherein a representative sample of seed of a corn plant comprising corn event MON 95379 has been deposited under ATCC Accession No. PTA-125027.

4. A method for protecting a corn plant from insect infestation, wherein said method comprises providing in the diet of a Lepidopteran insect pest an insecticidally effective amount of cells or tissue of a corn plant comprising a recombinant DNA molecule comprising SEQ ID NO:9 or SEQ ID NO:10.

5. The method of claim 4, wherein said Lepidopteran insect pest is selected from the group consisting of Fall Armyworm (*Spodoptera frugiperda*), Corn Earworm (*Helicoverpa zea*), Southwestern Corn Borer (*Diatraea grandiosella*), Surgarcane Borer (*Diatraea saccharalis*), and Lesser Cornstalk Borer (*Elasmopalpus lignosellus*).

6. A method of producing an insect resistant corn plant, said method comprising:
   a) sexually crossing two different corn plants, wherein at least one of the two different corn plants comprises SEQ ID NO:9 or SEQ ID NO:10;
   b) sampling seed or tissue from progeny of said crossing;
   c) detecting the presence of a DNA segment diagnostic for corn event MON 95379 DNA in said sample from step b) to identify progeny comprising corn event MON 95379 DNA; and
   d) selecting said progeny comprising corn event MON 95379 DNA;
   wherein a representative sample of seed of a corn plant comprising corn event MON 95379 has been deposited under ATCC Accession No. PTA-125027.

7. A corn seed comprising a detectable amount of SEQ ID NO:9 or SEQ ID NO:10.

8. A nonliving corn plant material comprising a detectable amount of SEQ ID NO:9 or SEQ ID NO:10.

9. A microorganism comprising a detectable amount of SEQ ID NO:9 or SEQ ID NO:10.

10. The microorganism of claim 9, wherein the microorganism is a plant cell.

11. A commodity product comprising SEQ ID NO:9 or SEQ ID NO:10.

12. The commodity product of claim 11, further selected from the group consisting of whole or processed corn seed, animal feed comprising corn, corn oil, corn meal, corn flour, corn flakes, corn bran, corn biomass, and fuel products produced using corn and corn parts.

13. The corn plant, corn plant part, or corn cell of claim 2, comprising SEQ ID NO:10.

14. A method of determining the zygosity of a corn plant or corn seed comprising event MON 95379, said method comprising:
   a) contacting a sample comprising DNA from said corn plant or corn seed comprising event MON 95379, wherein a representative sample of seed of a corn plant comprising corn event MON 95379 has been deposited under ATCC Accession No. PTA-125027, with a primer pair that is capable of producing an amplicon of the toxin coding sequence encoding Cry1B.868 or an amplicon of the toxin coding sequence encoding Cry1Da_7;
   b) contacting said sample comprising corn DNA with a primer pair that is capable of producing an amplicon of an internal standard known to be single-copy and homozygous in the corn plant;
   c) contacting the DNA sample with a probe set which contains at least a first probe that specifically hybridizes to the toxin coding sequence encoding Cry1B.868 or specifically hybridizes to the toxin coding sequence encoding Cry1 Da_7, and a second probe that specifically hybridizes to the internal standard genomic DNA known to be single-copy and homozygous in the corn plant;
   d) performing a DNA amplification reaction using real-time PCR and determining the cycle thresholds (Ct values) of the amplicon corresponding to the toxin coding sequence and the single-copy, homozygous internal standard;
   e) calculating the difference (ΔCt) between the Ct value of the single-copy, homozygous internal standard amplicon and the Ct value of the toxin coding sequence amplicon; and
   f) determining zygosity, wherein a ΔCt of zero (0) indicates homozygosity of the inserted T-DNA of event MON 95379 and a ΔCt of about one (1) indicates heterozygosity of the inserted T-DNA of event MON 95379.

15. The method of claim 14, wherein:
   a) the primer pairs are selected from the group consisting of SEQ ID NO:18 combined with SEQ ID NO:19, and SEQ ID NO:21 combined with SEQ ID NO:22; and the probes are SEQ ID NO:20 and SEQ ID NO:23; or
   b) the primer pairs are selected from the group consisting of SEQ ID NO:18 combined with SEQ ID NO:19, and SEQ ID NO:24 combined with SEQ ID NO:25; and the probes are SEQ ID NO:20 and SEQ ID NO:26.

16. A method of determining the zygosity of a corn plant or corn seed comprising event MON 95379, wherein a representative sample of seed of a corn plant comprising corn event MON 95379 has been deposited under ATCC Accession No. PTA-125027, said method comprising:
   a) contacting a sample comprising DNA from said corn plant or corn seed comprising event MON 95379 with a set of primer pairs comprising at least two different primer pairs capable of producing a first amplicon diagnostic for event MON 95379 and a second amplicon diagnostic for native corn genomic DNA not comprising event MON 95379;
   b) performing a nucleic acid amplification reaction with the sample and the set of primer pairs; and
   c) detecting in the nucleic acid amplification reaction the first amplicon diagnostic for event MON 95379, or the second amplicon diagnostic for native corn genomic DNA not comprising event MON 95379, wherein the presence of only the first amplicon is diagnostic of a corn plant or corn seed homozygous for event MON 95379, and the presence of both the first amplicon and the second amplicon is diagnostic of a corn plant or corn seed heterozygous for event MON 95379;

or said method comprising:

i) contacting a sample comprising corn DNA comprising event MON 95379 with a probe set which contains at least a first probe that specifically hybridizes to event MON 95379 DNA and at least a second probe that specifically hybridizes to corn genomic DNA that was disrupted by insertion of the heterologous DNA of event MON 95379 and does not hybridize to event MON 95379 DNA; and ii) hybridizing the probe set with the sample under stringent hybridization conditions, wherein detecting hybridization of only the first probe under the hybridization conditions is diagnostic for a corn plant or corn seed homozygous for event MON 95379, and wherein detecting hybridization of both the first probe and the second probe under the hybridization conditions is diagnostic for a corn plant or corn seed heterozygous for event MON 95379.

17. The method of claim 16, wherein:

a) the set of primer pairs comprises SEQ ID NO:15 combined with SEQ ID NO:16, and SEQ ID NO:15 combined with SEQ ID NO:27; or b) the probe set comprises SEQ ID NO:17 and SEQ ID NO:28.

* * * * *